(12) United States Patent
Ma et al.

(10) Patent No.: US 12,577,577 B2
(45) Date of Patent: *Mar. 17, 2026

(54) COMPOSITIONS AND METHODS TO INCREASE RESISTANCE TO PHYTOPHTHORA SOJAE IN SOYBEAN

(71) Applicants:CORTEVA AGRISCIENCE LLC, Indianapolis, IN (US); PURDUE RESEARCH FOUNDATION, West Lafayette, IN (US)

(72) Inventors: Jianxin Ma, West Lafayette, IN (US); Rajat Aggarwal, Indianapolis, IN (US); Liyang Chen, West Lafayette, IN (US); Weidong Wang, West Lafayette, IN (US); Oswald Crasta, Banford, CT (US); Jonathan Myrvold, Indianapolis, IN (US)

(73) Assignees: CORTEVA AGRISCIENCE LLC, Indianapolis, IN (US); PURDUE RESEARCH FOUNDATION, West Lafayette, IN (US)

( * ) Notice: Subject to any disclaimer, the term of this patent is extended or adjusted under 35 U.S.C. 154(b) by 146 days.

This patent is subject to a terminal disclaimer.

(21) Appl. No.: 18/266,871

(22) PCT Filed: Dec. 15, 2021

(86) PCT No.: PCT/US2021/063556
§ 371 (c)(1),
(2) Date: Jun. 13, 2023

(87) PCT Pub. No.: WO2022/132927
PCT Pub. Date: Jun. 23, 2022

(65) Prior Publication Data
US 2024/0052361 A1 Feb. 15, 2024

Related U.S. Application Data

(60) Provisional application No. 63/126,283, filed on Dec. 16, 2020, provisional application No. 63/154,913, filed on Mar. 1, 2021.

(51) Int. Cl.
*C07K 14/415* (2006.01)
*C12N 9/22* (2006.01)
(Continued)

(52) U.S. Cl.
CPC ........... *C12N 15/8279* (2013.01); *C12N 9/22* (2013.01); *C12N 15/11* (2013.01);
(Continued)

(58) Field of Classification Search
CPC ...... C12N 15/8279; C12N 9/22; C12N 15/11; C12N 15/8213; C12N 15/8282;
(Continued)

(56) References Cited

U.S. PATENT DOCUMENTS

| | | | |
|---|---|---|---|
| 10,760,088 B2 * | 9/2020 | Matarasso | C12N 15/8246 |
| 11,466,287 B2 * | 10/2022 | Ma | C07K 14/415 |
| 2013/0198912 A1 * | 8/2013 | Hudson | C12Q 1/6895 |
| | | | 536/23.6 |

OTHER PUBLICATIONS

Nickell et al (1998) Registration of 'Dwight' Soybean. Crop science 38:1398. (Year: 1998).*

(Continued)

*Primary Examiner* — Anne Kubelik
*Assistant Examiner* — Victoria L Deleo
(74) *Attorney, Agent, or Firm* — Barnes & Thornburg LLP

(57) ABSTRACT

Provided are compositions comprising polynucleotides encoding Rps genes, and soybean plants or soybean seeds comprising the compositions and exhibiting resistance to *Phytophthora*. Additionally, various methods for employing the polynucleotides to increase resistance to *Phytophthora* are also provided herein.

9 Claims, 14 Drawing Sheets

Figure 1:
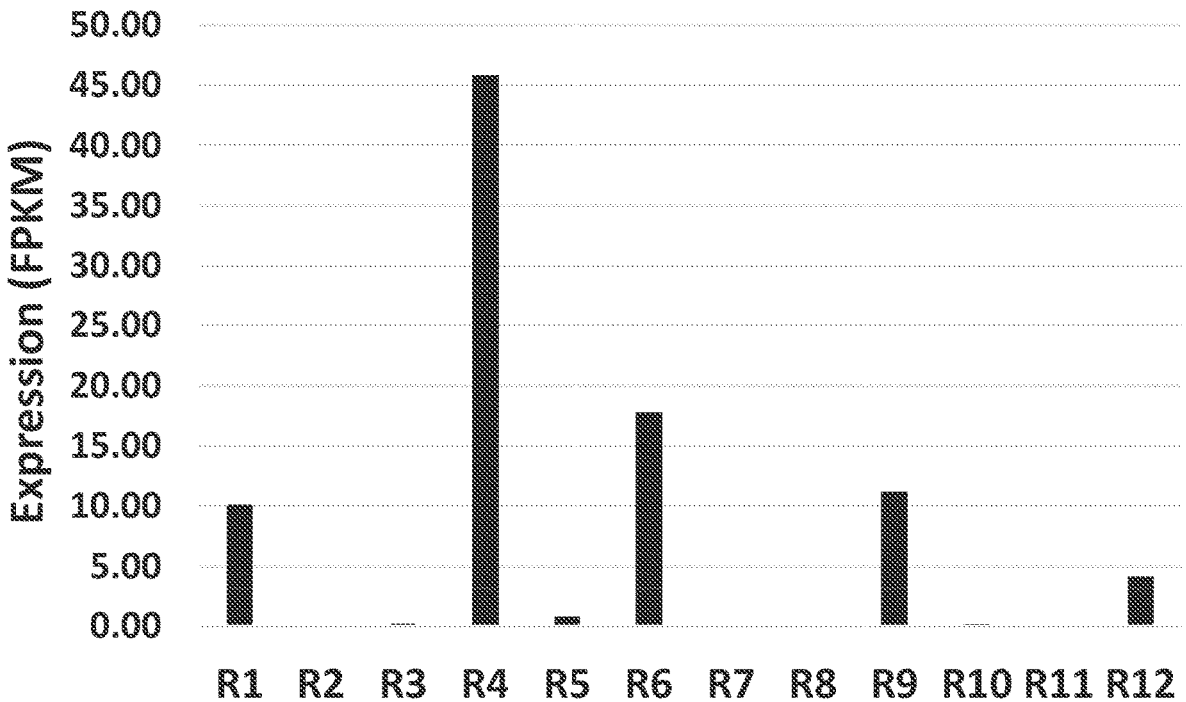

Specification includes a Sequence Listing.

(51) Int. Cl.
    *C12N 15/11*      (2006.01)
    *C12N 15/82*      (2006.01)
    *C12Q 1/6869*      (2018.01)
    *C12Q 1/6895*      (2018.01)

(52) U.S. Cl.
    CPC ..... *C12N 15/8213* (2013.01); *C12N 15/8282* (2013.01); *C12Q 1/6869* (2013.01); *C12Q 1/6895* (2013.01); *C12N 2310/20* (2017.05); *C12N 2800/80* (2013.01); *C12Q 2600/13* (2013.01); *C12Q 2600/156* (2013.01)

(58) Field of Classification Search
    CPC ............ C12N 2310/20; C12N 2800/80; C12Q 1/6869; C12Q 1/6895; C12Q 2600/13; C12Q 2600/156
    See application file for complete search history.

(56)            References Cited

OTHER PUBLICATIONS

Wang et al (2021) Nature Communications. 12:6263. (Year: 2021).*
Ping et al (2016) Theor Appl Genet . 129:445-451. (Year: 2016).*
PCT Intl. Search Report and Written Opinion completed by the ISA/US on Mar. 12, 2022 and issued in connection with PCT/US2021/063556, 15 pages.
UniProtKB Accession No. I1KI39_SOYBN, Glycine max (Soybean) (Glycine hispida) AAA domain—1-5, 31-33 containing protein, Jun. 13, 2012 [online]. [Retrieved on Mar. 3, 2022]. Retrieved from the internet: < URL: https://www.uniprot.org/uniprot/I1K139> Entire document.

* cited by examiner

Fig. 2

SEQUENCE LISTING

```
<160> NUMBER OF SEQ ID NOS: 123

<210> SEQ ID NO 1
<211> LENGTH: 14034
<212> TYPE: DNA
<213> ORGANISM: Glycine max

<400> SEQUENCE: 1
atggacgctg tgtcatccgc actactagag ccagtaacta attctgtgtt ggatctgctt      60
aaaaagcaag tggattacat ccgttacagg cgaaactttg atgaactaga cgagtgtgtt     120
aagcagctta aacataaaaa ggagatagta gatcatcaat gtgaggaagc tgtcaaaaat     180
ggacacgaaa ttgaaggtaa ggttagagaa tggttaggga aagtgggtaa atttgagaca     240
gaagtggaga agtattggaa cgatgatggc cacaaaaaga cacggttttc caactattta     300
tttccttact ttaggcatag actaggcaga ctagcaaaga agatggcagt tgagggtaaa     360
aagataaccg atgattgccc aaagtctgat gaaattgcct atagggtata cgtaacatct     420
aattatgcca ttttgtctaa taatgacctt atggattttg gttctagaaa atccataatg     480
gaacaaataa tggcaacact tgttgaagat cccactgtga aaatgattgg agtgtatgga     540
cgaagtgggg tgggtaagag cactttaatc aaagcaattg ctaaaattgc tcgagacaag     600
aagttgttta atgtggtggc tttttcagaa ataacagaca accccaatct aaaacaagtc     660
caggaagata ttgcttaccc tttgggattg aaattggaag gagaaggtga gaatgtaaga     720
gctgatcatc tacgaaggag gttaaagaaa gagaaagaga acacccttat aatcttggat     780
gacctttggg acagattaga cttgaatagg ttgggaattc cacttgatgg tgatgttgat     840
gataaacagg gtcccaaagg gccgacaaaa gaaaaatctc ttgctgatta taagggttgc     900 aaaatttgc taacttcaag gaaacgaaat gtattaacga ataaaatgga agttaaatta     960
actttctgtg tagaggaatt agatgaaaaa gatgctctga agttgtttcg gaaggaggct    1020
gcaatacaag gtgaaatgtc caagtctaaa aaagaaattg ttaagaagta ttgtgctggg    1080
ttacctatgg caatagttac agttggaagg gcattaagag acaagagcga ctcagagtgg    1140
gaaaaactta aaaaccaaga actggtggga gttcagaatc cgatggagat ttctgtaaaa    1200
atgagttatg accatctaga aaatgaggag ctcaagtcca ttttctttct ttgtgctcaa    1260
atgggtcatc aacccctaat tatggacttg gtgaagtatt gctttggttt gggaatactt    1320 gaagggggtct actcgcttgg ggaagctcgg gacagaatat ctacatcaat caaaaagctg    1380
aaagactcag gtttggtgtt ggatggaagt tctagtattc atttcaatat gcacgatctg    1440
gttcgagatg ctgctttatc tatagcacag aacgagcaaa atgtatttac tttgagaaat    1500
gggaaactta atgattggcc tgaactcaag aggtgcactt ctatttctat atgcaatagt    1560
```

```
gatatcattg atgagcttcc taatgttatg aactgtcctc aacttaaatt tttccaaatt    1620
gacaatgatg atccatcttt aaaaatacct gagagttttt ttaagagaat gaaaaaactc    1680
agagtgttaa tattgactgg ctttcatcta tcaagcttac catcatcaat taagtgccta    1740
tcagacctca gattgctttg tttggagcga tgcactttag atcacaactt atccatcata    1800
gggaagctga aaaaattaag aattctcagc ttttctggat ctcgaattga aaatttgcca    1860
gctgagttga aggacttgga taaactacaa ttactagaca tcagcaattg ttcaatagtc    1920
accatgattc cacctaatct tatatcaagg ttgacttcgt tggaagagct gtatgtaaga    1980
aagtgtttca tggaagtgtc ggaggaagga gagagaaacc aaagtcaaaa ttcatttatt    2040
tctgaactaa agcatttgca tcaattgcaa gtggtggact taagcattcc atgtgctgaa    2100 tttttttgcaa aggaattgtt ctttgacaac ttaagtgatt acaagattga gattgggaac    2160
ttcaaaactc tttcagctgg agatttcaga atgcctaata agtatgaaaa tttcaaatct    2220
ttggcattgg agctgaagga tgacactgac aatattcact ctcagacagg aataaagttg    2280
ttgtttgaaa cagttgaaaa tttgttgttg ggagagctga atggtgttca agatgttgtt    2340
aatgagttga atttgaatgg atttccacat ctgaaacact tttccatcgt aaacaaccct    2400
agcatcaaat atatcatcaa ctcaaaggat ttgtttttatc ctcaggatgt ttttcccaag    2460
ttggaatctc tatgcctcta caaactaaaa gagatagaga tgatatactt tagttcaggt    2520
acagagatga tatgctttag tccatttaca gattgctcat tcaccaaatt aaaaaccatc    2580
aaggtcgaga agtgtgatca attgaagaat cttttctcct tttgcatggt taaattgctt    2640
gcgagtcttg aaacaattgg tgtttccaat tgtggttctt tagaggagat cattaaaata    2700
ccagacaatt ctgataagat tgagtttctt aagttgatgt ctttgtcact tgaatcatta    2760
tcatcattca ctagtttta taccacagta gagggtctt ctacaaacag agatcagata    2820
caaattactg ttatgactcc tcctcttttt ggtgaactgg tatgatagtg catatttttc    2880
ctttaaaaat tttaattagt ctgtgactac ttattttca gttgcaaata tgttaattgt    2940
gtatgtgctt gcaggttgaa ataccaaact tagagaactt gaatttaatc tcaatgaaca    3000
agatccagaa gatatggagc gaccagcccc cgtcaaactt ctgctttcag aacttaataa    3060
aattagttgt gaaagattgt caaaatttga gatatttgtg ttcattgtcc gtggccagca    3120
gtttgaggaa actgaaaggc ctctttgtaa gcaactgtaa aatgatggag aagattttta    3180
gcacagaagg aaatagtgca gacaaggtgt gtataggtgt aaataagtaa atttttatag    3240
ttgactgaat gttatgcatt tctgtttagt ttcattacca aataatggct tgttttcatc    3300
gaagtgcagg tttgcgtctt tcctaagttg gaggaaattc acctcgacca aatggatgag    3360
ttaacagaca tatggcaagc tgaagtgagt gctgattcct tttctagtct cacttctgtg    3420
aacattcgta gttgtcataa actagacaaa attttttccga gtcacatgga aggatggttt    3480
gcgagtttga acagcttgaa ggtttctttt tgtgagtcag tggaagtgat ttttgaaatc    3540
aaagattctc agcaagtaga tgcatctggt gggatagaca caaatttgca ggttgtttat    3600
gtaagtgaac tcccaaagtt ggagcaggtg tggagcaggg atccaggagg aattcttaac    3660
ttcaaaaaac tgcagagtat agagatggat gattgtgaaa gactgaggaa tgtatttcca    3720
gcttctgtgg gcaaagatgt tccaaagctt gaatacatgt cggtcataga gtgtgatgga    3780
attgtggaaa ttgttgcctg tgaagatgga tccgaaacaa acactgaaca attagtgttt    3840
cctgaactaa ccgacatgga attatgttac ctatcaagca tccagcattt ctacaggggg    3900
```

-continued

```
agacatccta tagagtgtcc aaaattgaag aagttgtcag tagggaaatg taacgagaag      3960
ctaaaaacat tcggaaccgg agaaaggagc aatgaagaag atgaagcagt tatgtcagct      4020
gaaaaggtaa gtcatatagt gagacataaa tggagagtga tattgtaaga tgtgtggcat      4080
acttaaaaaa gatatagccc tgctaaatat aaatatggatt attaatttaa cgtctctcgt     4140
cccctaatcc ctctaaatcc aaattcctca ttgtgcctta aaattttatt tagaatttag      4200
aattgaaggg aatgtttgat taattattat aatttaagag cattttttag ttttgatggg      4260
acccgagagt aaccaatgtg caggcaaggc gtaaaataat ggaaaggggc gctccatcag      4320
ggataagctt ccttcttcat agtttactat ttacttttat tttatttttc tgtagatatt      4380
ccccaacttg gagtatttgg atattcactt tgacgaagca cagaagtggt tattgagcaa      4440
cactgtgaag catcgaatgc accgtttaaa aaagcttagg ttaagcgaag ttaatgatgg      4500
tgaacgtctc tgtcaaattc tgtacagaat gccaaatcta gaaaagttat acttgccgat      4560
ggctaaacat ttgcttaaag agtcgtcgga gtcccgtttg ggaaccctat tacagctgaa      4620
ggaattggat ttgtggaggt cggagataaa ggatatagga tttgaacgag aaccagttct      4680
acagagacta gagcttttga gcttatttaa gtgccataaa ttgaggaatt tgggtcctcc      4740
ctcggtatca ttggcttact tgacaaattt gaaagtagag tattgttatg gattaaggaa      4800
tttaatggca tcctcaacgg caaaaagctt ggttcaactt aagtccatga agataagaaa      4860
atgttgtaaa ttagaggaaa tagtaagcga tgagggaaat gaagaagaag agcaaatagt      4920
gtttggcaaa ttgattacta tagaacttga ggggctaaaa aagctgaaaa gtttttgcag      4980
ttccaagaac tatgaattca aattcccgtc attggaagga ttgattgtga gaaaatgccc      5040
aatgatgcat acattcacgg agggtgacgc aagagcacca aagttagaaa acacagttac      5100
tgctaaagaa gaaggaaaag aggaagccaa atggcagtgg gaaggagact tgaattccac      5160
catacaaaaa ggtttcaaca aggtacttat tcatttattt atgatttaaa tatattttta      5220
tttatcttgt tagtattttt ttattcttcc tttttttattt ttgttcttca aagttattat     5280
ttttgttaat tttagtcttt ttaggttatt tcattcattt ttaatacgtt aatttttttt      5340
aaaattttag tctctttaat attttaaaat attcatttat aatcctccgc acgaaattaa      5400
aattaaaaaa tataaactta taaaataaaa aatgagtaaa acatattacg gagatcaaaa      5460
ttaaaaaagc ataaactttc aacgactaaa attaaaaaaa aaaaacttac cagagacaaa      5520
aattaaaaaa tattaactta catttatcaa atacatattt aaacttatat ttattacaaa      5580
ttctcctagt tttattaact tttcttcttt ccttacaaaa acaaactttt cttctttcat      5640
gagataaaaa aaattacttg ccatgaatgg aaattataaa tccttgtttt tcccataaaa      5700
agccttaacc agcaagtatg ttaaatttct taagatataa atatgttagc tcaaaaaacc      5760
agcatttata taaatttatt aatcattttt gttttaaaaa aattcattca taaaatttaa      5820
aataatacga atgtgactgc ttcatgtagc cagcgtagtc ataaagaaaa cattccctca      5880
tcttacaact tttttttttta attataataa ataaacttca attcatattt gattatcatc     5940
cattaatttt ttgttaacat ttttagtcct tttagaaatt tttgctcatt attaatccta      6000
ttgtttatgt tatatttaag aaaaaaaaac gactaaaaat ggatcgatga acacattttt      6060
agagggatta aaactttaaa gaaagattga aatttgtaaa aaaattgagg gggaaaaatt      6120
agaatataaa aaaatgagga gttaaaaaact taattacatt tgactttaca tatataaaat     6180
aacatataaa cgtgataata aattaacaaa cttatccata taatttgtga ctatttatat      6240
atctataaaa taaaagtcac atgagacgtt attataactt acaaggttga ttttgtagtt      6300
```

-continued

```
ggaaaaaaga atttgaaggg aaaaggatga aagaggtttt aagttacgat actttcacta   6360
atattttaat aaaaaactaa aactaacaag taatattaat tgatgaaaaa aatgtctttt   6420
atacatacgg aaaaataagg atgaaatgta tttttttttc tttttttgtt aaaatataaa   6480
atatcgtgaa aataaaatga cattattaca cctaagagta aatgataaaa tatttcttaa   6540
tcgaataatc cataatttca tcattgataa aaataaatta tcatgttatt tacttatata   6600
ttttttgttt aatcttttgt gcagctatcc atatttagta ttttagcaca tgaatggcag   6660
aaagtaaata tttatttata caacaagatt gtaatttata ataaataaat attttaagta   6720
tataaattat attataatta aattttctaa tatataattt ttaacatata aattacattt   6780
taaatttatg aaaaataatt tatgttagga tgtattatta ttttaaataa ttgatgtttt   6840
cttttaaaaa tatttaaatt aagttagaaa caaggatgcc gtcaagtttt cttacagcct   6900
acatttatcg tgatgaagga aggaaggtgt tttaatggtc ccctgatgat gaaacttgga   6960
atgtaatttt ataataaaca acggacataa ttgctccctc catattaata tctgtttgcc   7020
acacaactca gtcccatcat tatttggcgt tgacttcttc atcttatacc aagatagcaa   7080
gagtccatgg attcattttt tattattaat tattaattat ataaaaattt atttatattt   7140
attatccatt tgactattga gttttaagat attaggtttt tttcattaaa atataataaa   7200
tatattttta attaatatga taatctcaaa gtaaaaaaat tattatattt attattaaga   7260
atttttcatt gaaagtttaa aatattgtta acaactaaaa attttcactt caattaattt   7320
aattaattta ataatgtcat ccacatgtga attatttata tatataattt aataaataag   7380
attaattatt tttcttcaat aaagacggtt atggatacat taatctgtct ccattattat   7440
tatcttattt cattataatc ttatgattaa aaataaaata gattaaaatt ataaaagaat   7500
tgattagtat tattattata atttctatca tatagcaagt gtttaatttt aatccagatc   7560
tatcaagtta acaatttaat aataaataaa taataatatt tttatcaaaa ttaataatat   7620
gatggattag atctttaaca tacatattta attctagcaa tacacacata tatatatata   7680
tatatatata tatatatata tatatatata tatatatata tataaatttt tacatttttta   7740 cttatggttt atctaaaaat aataaaataa atctatgatc ttatagttta tattataaat   7800
agctttcttt attaattaat aatatttttt ataatataga gctattttt catttgttaa   7860 acccatgttt gtttgaattt ttattcaaat ttttctatga ttttttttcta caaattgtta   7920 taattttgat agagaaaaat atgattatct tctttaagtt cattaaaaaa tccatagatt   7980
ttttcccctg tatcctcaca caaatatttt gtatataaac aaacaaacta aatgtttcag   8040 gttcatttttt tcacacaaaa aaatggaaat gaaattttta attttttcaga caaaagtaaa   8100 aaaaaaaatt atactatata aaaaatattt tggttcctcc aatatttttt ttctcaaagt   8160
tccgccactg atttcatgcg tctctatgtc taatatcaag ttcctctctt tttctttgtc   8220
tttttattaa ctaaattcag tattaagaca gtaactgatt tatgactaat ctatctattt   8280
gttataatgt aatcgccagc tatgaaactg acatattagc cttttgtatg caatatccta   8340
ttttgcatgc acagcttttg gagtctgcaa gtactgaatc atctcttagt ctcatagata   8400
gcccactaca agtgatatgg cttgactcac ggcggatccc aaagtcgtgc ttcagtaact   8460
tgacggaatt gactgtgcac ggatgccaat ttttaacaga tgttgtcata cccttctatt   8520
tacttccttt cttaactaat ttgcaacaat tacaagtctc ggactgtcgt tctgtgaaaa   8580
gcatatttga cgtgaaaaca gctatgggat tgggagcagc agccttccct agacctctcc   8640
```

-continued

```
cttttttccct caagaaattg actttagagt ggctgccaaa actggagaat gtctggaatg    8700
aagatcctca tggaattcta accatgcaac ttctacaaca tgtaaaggtt aaaaattgta    8760
aatgccttac aagtgtgttt ccggcatcat tagccaaaga tcttgaaaaa ctagttgtca    8820
aagactgtga gggattgata gaaattgttg cagaggataa tgcagatcca agagaagcaa    8880
atctggagct tacgttccct tgtccctgtg tgagctcatt gaaactacaa ggtttgccca    8940
agttcaagta tttttactac tgctcactgc agtgtgacat gttccagaca cctaccaagg    9000
atgaaatggt actattgtgt tactactttg tccttactgc ataatctcat gcctgcaaat    9060
taaatataat tgcactactt catttttatt gttcaacatg agtgatatga acattctctt    9120
caaattaaaa tgtgagaatt tcacgtacat tgctatatat atatgccgtg ttctatcttc    9180
tatacctatt aactcccatt tttcatgttt tacataaata agtaaaagaa tacacttaag    9240
ggtacatgtt gcattcatga cacaacaatg acattttagg tttgagcttt attcttatta    9300
atacagacaa ttacatagaa tcttacacat gccattttac tttatcaaat acaatgtatg    9360
gatggttttc aaatctttat aaacaatctc cctaccatat aaaggatcga attttcatc    9420 attttcttct ccgttggaac cactactacc tcccttaagg tctcctttat caccttttcc    9480
atctaaaatt ttaaactaca aataaataaa tttgtttagg cacaaaccgt atcaaaatcc    9540
cttccacctt attaatagct agctagccag gttcatctct tttataacct cactaacctg    9600
cttttgcttg gttatcggtt tctcttggta gcctacatcc aacttacagt gcctgtcact    9660
cggtgaaaaa ggactggaga tgatcaagcg tgcagaattt cagagaaact tcttacacaa    9720
gttacaagtt cttactctgt gctttcatat tgggtcgaat gtatttccat atgaaattct    9780
acaactggcg cccaatatag agaagcttgt ggtgtgtgat ggttccttca aggagatttt    9840
ctgctttgat agtcttaatg tggatgaggc tggactccta ttacagctca aagtcttatg    9900
cttggagtcc cttccagagc ttgtttccat tgggttagag aactcttgga ttcagccctt    9960
actgggaaat ctagaaacct tggaagtaat aggttgttct agtttaaaag acttggtacc   10020
atctacagtg tctttttcca atctgacata tttggaagta gaaagatgcc attgcctgct   10080
atatttgttc acatcctcca cagcaagaag tttgggtcaa ctcaaaagaa tggagataaa   10140
atggtgtggt tcaattgaag aggtagtagt ctctaaggag ggggatgaat cacatgagga   10200
ggagattata tttccgcagc tcaattgttt gaaacttgaa tatttatcaa agctgagaag   10260
cttctataaa ggaagtttat taagtttccc atcattggag gaattgtcag taatccgttg   10320
cgagtggatg gaaacattat gtccaggtac ccttaaagca gacaagttgg ttcaagttca   10380
acttaaggag agttattctt ggaggcactc agatcctatc aaattggaaa atgacctgaa   10440
ctctaccatg cgggaggcat tttggaaaaa ggtatgtttt caattatttt gattaaatat   10500
gattgatatt ggtgtatgtt gttcttataa tgcaaaatat acaccgttag gttgattaga   10560
ttcatcttca aattaacttg ggcctcatcc aatttatctt ggattttcag cgtcgtccaa   10620
tttttcggaa aaccaaaaaa ctcacagaaa caacatttat gtgccaatcc aatttggcta   10680
atattaattt tttacgttaa actcataata tttaaataat ttaatttatt ttctatgtac   10740
tttatcaatg ctacttaact tttatatata ttaataatat aaaatgaatc caaactcttt   10800
caagtcattg taaaaatgat ttgaaaatta tttaattttt attttatttta tattaatcct   10860 attaaataaa agaaactatc aatcttttgt aatccaatct tatatacata ttcaaaatat   10920
ttatctttta gcaattttaa ctatataaaa aaattatctt ctaggattaa gatactatat   10980
aattatattt aaaatctaga ttaggtagtt aaaatgttag ttgttcattt ttttttaatt   11040
```

-continued

```
ttctttaact ttttgttatt tcttcattta tacataaaaa taaattaaat aaatattaaa   11100
aaaattagag tgacttgaag aagtttagat tcactgtata ttattattat tattaattac   11160
taatacaaat aaaagttaag tagtataagt aaggtatata aaaaataatt atttaaatat   11220
tagtgagttt agcttactaa aaaattaaga gattcttttt ttagtataag gtaagaggtt   11280
aatataagtc aaataatttt gtttgtcaac ttaattgtat gacgtgactg caagctcaat   11340
ctaatggtat atattgtgtt ggagagaaaa gtatgttcaa gagcatctgg atcttatatt   11400
ttaacggaga ttaaatgtgt tgtatttatt agtattcatt gcatatatga attttttata   11460
agaaatggtc attaaatttg tgcgattttc ttataaataa ctcaccagtt gagactaata   11520
aatatgctaa attttcttta attttctaa gtaagataaa aaaatactcg atcgactatc    11580
tagctttgat catgcgtatg ttttgtcaaa tgatgaattt tgaattttga aaaataacct   11640
actctttctt atacaaatat ctagaaactt ttttatgagt gcaacaaaga catataaaaa   11700
atattctgga aaatactttc attgtgtgtt gataaattta gaatgaatgt accagaatca   11760
actagttgaa aactattatc tcaggcgcat tcatccagaa atcaactcaa ggaggagctg   11820 atttttttc cttacaaat tatttaaata attttgaagg cagattttga ttagagagca     11880
tccacgatta acggaaatct ggactataat cagaaatttg ttacttttt aatttattgt     11940 tttaaaaata attacacttt aaaaattgag agcacattag ttatttggtg cgattgggga    12000
tgcatttctt cctacagaat aatactactc tttttttta ttcttttacg tttgcagtta     12060
tggaagtctg cagatacgga attcagtatt gacctcaaag atagcccagt acaagagata    12120
tggcttaggc ttcactcact gcatatcccc ccacacttct gcttccctaa gttacacacc    12180
ttgattgtgg acggctgcca tttttttatca gatgcggtct tacccttctc tttacttcct   12240
ttattaccta atttgaaaac attggaagtt cgaaactgtg attttgtgaa aatcatattt    12300
gatgtgacaa ctatgggacc actccctttt gccctcaaga cattggcact gtgtgatctg    12360
ccaaatctgg agaatgtttg gaattcaaat gttgagctta cgttccccca agtcaagtca    12420
ttggcactct gtgatctgcc aaagttaaag tatgacatct tgaagccatt tacacatcta    12480
gaaccacata ctctaaatca agtctgtatt caaaaggtat cattactact tctatatata    12540
tgaactaaat tgccatcatt agtgttcttt actacttcta tatatatgaa ctaaattgcc    12600
atcattagtg ttctttacta cttctatata tatgaacaaa ttgccatcct gttaaaatta    12660
aaaagttgtg aacctttccc ttatacagtt atatatgcta tgttgagtct tctatccatc    12720
ttctacgcat attggcttcc atttttctat tttttattta tctacataag tcagataata    12780
cggctacagc tactattcaa tattgatcat gatgaattta taatggaaca tgttgcattc    12840
atgatgtgaa acagcatttg aggtgcgatc cttattctca ttattttctt ctacaacctt    12900
actaataatc tcatctatca cttttcccat cttaaaatat taaagtcgac atacggtgtg    12960
aatatccttt ctccacctta ttcttttat ggtatccttt tccaccttat aaatagctag     13020
cctagttcgt cttttttct ttttggttt ttaagtaaac tgatttcttt taaattgact      13080
tgtttgcacc tatttaattg aattggttaa tttgtcatta attattggac ttattttagc    13140
gtgaaagttc attatttcaa ttatataaaa agagctggat ctataacttc cctaacctgc    13200
tttttcttca ttgttggttt ctcttggtag cttacaccca acatagagca cctgacactc    13260
ggtgaacatg aactcaacat gattttgagt ggagaattcc agggaaacca cttaaacgag    13320
ttaaaagtgc ttgctctgtt ctttcatatt gaatccgatg tatttctaca acgggtgccc    13380
```

```
aatatagaga agcttgaggt gcgtgatggt tccttcaaag agattttctg ctttgatagc   13440
cttaatgtgg atgaggatgg attggtttca cagctgaaag tgatatgccc ggactccctt   13500
ccagagcttg tttccattgg gtcagagaac tctgggattg tgccctttct cagaaatcta   13560
gaaacattgc aagtaatcag ctgtttcagt tcaataaatc tggtaccatg cacagtgtct   13620
ttttccaatc tgacatattt gaaagtagaa agttgcaaga gtctgctata tttgttcaca   13680
tcctcaacag caagaagttt gggtcaactc aaaacaatgg agataagttg gtgtaattca   13740
attgaagaga tagtgtcttc aacagaggaa ggggatgaat cagatgagaa tgagataata   13800
tttcagcagc tcaattgttt gaaacttgaa ttttttattta agctgagaag gttctacaaa   13860
gggagtttaa gtttcccgtc cttggaggaa ttcacagtat ggcgttgcga gaggatggaa   13920
agtttgtgtg caggtacagt caaaacagac aagctgttac aagtgaatac taattggggc   13980
ggagatgtta tcccattgga aactgatctg aactctgcca tgcaaaaccg atag        14034
```

```
<210> SEQ ID NO 2
<211> LENGTH: 2463
<212> TYPE: PRT
<213> ORGANISM: Glycine max

<400> SEQUENCE: 2

Met Asp Ala Val Ser Ser Ala Leu Leu Glu Pro Val Thr Asn Ser Val
1               5                   10                  15

Leu Asp Leu Leu Lys Lys Gln Val Asp Tyr Ile Arg Tyr Arg Arg Asn
            20                  25                  30

Phe Asp Glu Leu Asp Glu Cys Val Lys Gln Leu Lys His Lys Lys Glu
        35                  40                  45

Ile Val Asp His Gln Cys Glu Glu Ala Val Lys Asn Gly His Glu Ile
    50                  55                  60

Glu Gly Lys Val Arg Glu Trp Leu Gly Lys Val Gly Lys Phe Glu Thr
65                  70                  75                  80

Glu Val Glu Lys Tyr Trp Asn Asp Asp Gly His Lys Lys Thr Arg Phe
                85                  90                  95

Ser Asn Tyr Leu Phe Pro Tyr Phe Arg His Arg Leu Gly Arg Leu Ala
            100                 105                 110

Lys Lys Met Ala Val Glu Gly Lys Lys Ile Thr Asp Asp Cys Pro Lys
        115                 120                 125

Ser Asp Glu Ile Ala Tyr Arg Val Tyr Val Thr Ser Asn Tyr Ala Ile
    130                 135                 140

Leu Ser Asn Asn Asp Leu Met Asp Phe Gly Ser Arg Lys Ser Ile Met
145                 150                 155                 160

Glu Gln Ile Met Ala Thr Leu Val Glu Asp Pro Thr Val Lys Met Ile
                165                 170                 175

Gly Val Tyr Gly Arg Ser Gly Val Gly Lys Ser Thr Leu Ile Lys Ala
            180                 185                 190

Ile Ala Lys Ile Ala Arg Asp Lys Lys Leu Phe Asn Val Val Ala Phe
        195                 200                 205

Ser Glu Ile Thr Asp Asn Pro Asn Leu Lys Gln Val Gln Glu Asp Ile
    210                 215                 220

Ala Tyr Pro Leu Gly Leu Lys Leu Glu Gly Gly Glu Asn Val Arg
225                 230                 235                 240

Ala Asp His Leu Arg Arg Arg Leu Lys Lys Glu Lys Glu Asn Thr Leu
                245                 250                 255

Ile Ile Leu Asp Asp Leu Trp Asp Arg Leu Asp Leu Asn Arg Leu Gly
```

-continued

```
                260              265              270
Ile Pro Leu Asp Gly Asp Val Asp Asp Lys Gln Gly Pro Lys Gly Pro
            275              280              285

Thr Lys Glu Lys Ser Leu Ala Asp Tyr Lys Gly Cys Lys Ile Leu Leu
        290              295              300

Thr Ser Arg Lys Arg Asn Val Leu Thr Asp Lys Met Glu Val Lys Leu
305              310              315              320

Thr Phe Cys Val Glu Glu Leu Asp Glu Lys Asp Ala Leu Lys Leu Phe
                325              330              335

Arg Lys Glu Ala Ala Ile Gln Gly Glu Met Ser Lys Ser Lys Lys Glu
            340              345              350

Ile Val Lys Lys Tyr Cys Ala Gly Leu Pro Met Ala Ile Val Thr Val
            355              360              365

Gly Arg Ala Leu Arg Asp Lys Ser Asp Ser Glu Trp Glu Lys Leu Lys
        370              375              380

Asn Gln Glu Leu Val Gly Val Gln Asn Pro Met Glu Ile Ser Val Lys
385              390              395              400

Met Ser Tyr Asp His Leu Glu Asn Glu Glu Leu Lys Ser Ile Phe Phe
                405              410              415

Leu Cys Ala Gln Met Gly His Gln Pro Leu Ile Met Asp Leu Val Lys
            420              425              430

Tyr Cys Phe Gly Leu Gly Ile Leu Glu Gly Val Tyr Ser Leu Gly Glu
        435              440              445

Ala Arg Asp Arg Ile Ser Thr Ser Ile Lys Lys Leu Lys Asp Ser Gly
        450              455              460

Leu Val Leu Asp Gly Ser Ser Ser Ile His Phe Asn Met His Asp Leu
465              470              475              480

Val Arg Asp Ala Ala Leu Ser Ile Ala Gln Asn Glu Gln Asn Val Phe
                485              490              495

Thr Leu Arg Asn Gly Lys Leu Asn Asp Trp Pro Glu Leu Lys Arg Cys
            500              505              510

Thr Ser Ile Ser Ile Cys Asn Ser Asp Ile Ile Asp Glu Leu Pro Asn
            515              520              525

Val Met Asn Cys Pro Gln Leu Lys Phe Phe Gln Ile Asp Asn Asp Asp
        530              535              540

Pro Ser Leu Lys Ile Pro Glu Ser Phe Phe Lys Arg Met Lys Lys Leu
545              550              555              560

Arg Val Leu Ile Leu Thr Gly Phe His Leu Ser Ser Leu Pro Ser Ser
            565              570              575

Ile Lys Cys Leu Ser Asp Leu Arg Leu Leu Cys Leu Glu Arg Cys Thr
            580              585              590

Leu Asp His Asn Leu Ser Ile Ile Gly Lys Leu Lys Lys Leu Arg Ile
            595              600              605

Leu Ser Phe Ser Gly Ser Arg Ile Glu Asn Leu Pro Ala Glu Leu Lys
        610              615              620

Asp Leu Asp Lys Leu Gln Leu Leu Asp Ile Ser Asn Cys Ser Ile Val
625              630              635              640

Thr Met Ile Pro Pro Asn Leu Ile Ser Arg Leu Thr Ser Leu Glu Glu
                645              650              655

Leu Tyr Val Arg Lys Cys Phe Met Glu Val Ser Glu Glu Gly Glu Arg
            660              665              670

Asn Gln Ser Gln Asn Ser Phe Ile Ser Glu Leu Lys His Leu His Gln
            675              680              685
```

-continued

```
Leu Gln Val Val Asp Leu Ser Ile Pro Cys Ala Glu Phe Phe Ala Lys
    690             695             700

Glu Leu Phe Phe Asp Asn Leu Ser Asp Tyr Lys Ile Glu Ile Gly Asn
705             710             715             720

Phe Lys Thr Leu Ser Ala Gly Asp Phe Arg Met Pro Asn Lys Tyr Glu
            725             730             735

Asn Phe Lys Ser Leu Ala Leu Glu Leu Lys Asp Asp Thr Asp Asn Ile
            740             745             750

His Ser Gln Thr Gly Ile Lys Leu Leu Phe Glu Thr Val Glu Asn Leu
            755             760             765

Leu Leu Gly Glu Leu Asn Gly Val Gln Asp Val Val Asn Glu Leu Asn
    770             775             780

Leu Asn Gly Phe Pro His Leu Lys His Phe Ser Ile Val Asn Asn Pro
785             790             795             800

Ser Ile Lys Tyr Ile Ile Asn Ser Lys Asp Leu Phe Tyr Pro Gln Asp
            805             810             815

Val Phe Pro Lys Leu Glu Ser Leu Cys Leu Tyr Lys Leu Lys Glu Ile
            820             825             830

Glu Met Ile Tyr Phe Ser Ser Gly Thr Glu Met Ile Cys Phe Ser Pro
            835             840             845

Phe Thr Asp Cys Ser Phe Thr Lys Leu Lys Thr Ile Lys Val Glu Lys
    850             855             860

Cys Asp Gln Leu Lys Asn Leu Phe Ser Phe Cys Met Val Lys Leu Leu
865             870             875             880

Ala Ser Leu Glu Thr Ile Gly Val Ser Asn Cys Gly Ser Leu Glu Glu
            885             890             895

Ile Ile Lys Ile Pro Asp Asn Ser Asp Lys Ile Glu Phe Leu Lys Leu
            900             905             910

Met Ser Leu Ser Leu Glu Ser Leu Ser Ser Phe Thr Ser Phe Tyr Thr
            915             920             925

Thr Val Glu Gly Ser Ser Thr Asn Arg Asp Gln Ile Gln Ile Thr Val
    930             935             940

Met Thr Pro Pro Leu Phe Gly Glu Leu Val Glu Ile Pro Asn Leu Glu
945             950             955             960

Asn Leu Asn Leu Ile Ser Met Asn Lys Ile Gln Lys Ile Trp Ser Asp
            965             970             975

Gln Pro Pro Ser Asn Phe Cys Phe Gln Asn Leu Ile Lys Leu Val Val
            980             985             990

Lys Asp Cys Gln Asn Leu Arg Tyr  Leu Cys Ser Leu Ser  Val Ala Ser
            995             1000            1005

Ser Leu Arg Lys Leu Lys Gly  Leu Phe Val Ser Asn  Cys Lys Met
    1010            1015            1020

Met Glu  Lys Ile Phe Ser Thr  Glu Gly Asn Ser Ala  Asp Lys Val
    1025            1030            1035

Cys Val  Phe Pro Lys Leu Glu  Glu Ile His Leu Asp  Gln Met Asp
    1040            1045            1050

Glu Leu  Thr Asp Ile Trp Gln  Ala Glu Val Ser Ala  Asp Ser Phe
    1055            1060            1065

Ser Ser  Leu Thr Ser Val Asn  Ile Arg Ser Cys His  Lys Leu Asp
    1070            1075            1080

Lys Ile  Phe Pro Ser His Met  Glu Gly Trp Phe Ala  Ser Leu Asn
    1085            1090            1095
```

-continued

```
Ser Leu  Lys Val Ser Phe Cys  Glu Ser Val Glu Val  Ile Phe Glu
    1100              1105              1110

Ile Lys  Asp Ser Gln Gln Val  Asp Ala Ser Gly Gly  Ile Asp Thr
    1115              1120              1125

Asn Leu  Gln Val Val Tyr Val  Ser Glu Leu Pro Lys  Leu Glu Gln
    1130              1135              1140

Val Trp  Ser Arg Asp Pro Gly  Gly Ile Leu Asn Phe  Lys Lys Leu
    1145              1150              1155

Gln Ser  Ile Glu Met Asp Asp  Cys Glu Arg Leu Arg  Asn Val Phe
    1160              1165              1170

Pro Ala  Ser Val Gly Lys Asp  Val Pro Lys Leu Glu  Tyr Met Ser
    1175              1180              1185

Val Ile  Glu Cys Asp Gly Ile  Val Glu Ile Val Ala  Cys Glu Asp
    1190              1195              1200

Gly Ser  Glu Thr Asn Thr Glu  Gln Leu Val Phe Pro  Glu Leu Thr
    1205              1210              1215

Asp Met  Glu Leu Cys Tyr Leu  Ser Ser Ile Gln His  Phe Tyr Arg
    1220              1225              1230

Gly Arg  His Pro Ile Glu Cys  Pro Lys Leu Lys Lys  Leu Ser Val
    1235              1240              1245

Gly Lys  Cys Asn Glu Lys Leu  Lys Thr Phe Gly Thr  Gly Glu Arg
    1250              1255              1260

Ser Asn  Glu Glu Asp Glu Ala  Val Met Ser Ala Glu  Lys Ile Phe
    1265              1270              1275

Pro Asn  Leu Glu Tyr Leu Asp  Ile His Phe Asp Glu  Ala Gln Lys
    1280              1285              1290

Trp Leu  Leu Ser Asn Thr Val  Lys His Arg Met His  Arg Leu Lys
    1295              1300              1305

Lys Leu  Arg Leu Ser Glu Val  Asn Asp Gly Glu Arg  Leu Cys Gln
    1310              1315              1320

Ile Leu  Tyr Arg Met Pro Asn  Leu Glu Lys Leu Tyr  Leu Pro Met
    1325              1330              1335

Ala Lys  His Leu Leu Lys Glu  Ser Ser Glu Ser Arg  Leu Gly Thr
    1340              1345              1350

Leu Leu  Gln Leu Lys Glu Leu  Asp Leu Trp Arg Ser  Glu Ile Lys
    1355              1360              1365

Asp Ile  Gly Phe Glu Arg Glu  Pro Val Leu Gln Arg  Leu Glu Leu
    1370              1375              1380

Leu Ser  Leu Phe Lys Cys His  Lys Leu Arg Asn Leu  Gly Pro Pro
    1385              1390              1395

Ser Val  Ser Leu Ala Tyr Leu  Thr Asn Leu Lys Val  Glu Tyr Cys
    1400              1405              1410

Tyr Gly  Leu Arg Asn Leu Met  Ala Ser Ser Thr Ala  Lys Ser Leu
    1415              1420              1425

Val Gln  Leu Lys Ser Met Lys  Ile Arg Lys Cys Cys  Lys Leu Glu
    1430              1435              1440

Glu Ile  Val Ser Asp Glu Gly  Asn Glu Glu Glu Glu  Gln Ile Val
    1445              1450              1455

Phe Gly  Lys Leu Ile Thr Ile  Glu Leu Glu Gly Leu  Lys Lys Leu
    1460              1465              1470

Lys Ser  Phe Cys Ser Ser Lys  Asn Tyr Glu Phe Lys  Phe Pro Ser
    1475              1480              1485

Leu Glu  Gly Leu Ile Val Arg  Lys Cys Pro Met Met  His Thr Phe
```

```
              1490                1495                1500

Thr Glu  Gly Asp Ala Arg Ala  Pro Lys Leu Glu Asn  Thr Val Thr
    1505                1510                1515

Ala Lys  Glu Glu Gly Lys Glu  Glu Ala Lys Trp Gln  Trp Glu Gly
    1520                1525                1530

Asp Leu  Asn Ser Thr Ile Gln  Lys Gly Phe Asn Lys  Leu Leu Glu
    1535                1540                1545

Ser Ala  Ser Thr Glu Ser Ser  Leu Ser Leu Ile Asp  Ser Pro Leu
    1550                1555                1560

Gln Val  Ile Trp Leu Asp Ser  Arg Arg Ile Pro Lys  Ser Cys Phe
    1565                1570                1575

Ser Asn  Leu Thr Glu Leu Thr  Val His Gly Cys Gln  Phe Leu Thr
    1580                1585                1590

Asp Val  Val Ile Pro Phe Tyr  Leu Leu Pro Phe Leu  Thr Asn Leu
    1595                1600                1605

Gln Gln  Leu Gln Val Ser Asp  Cys Arg Ser Val Lys  Ser Ile Phe
    1610                1615                1620

Asp Val  Lys Thr Ala Met Gly  Leu Gly Ala Ala Ala  Phe Pro Arg
    1625                1630                1635

Pro Leu  Pro Phe Ser Leu Lys  Lys Leu Thr Leu Glu  Trp Leu Pro
    1640                1645                1650

Lys Leu  Glu Asn Val Trp Asn  Glu Asp Pro His Gly  Ile Leu Thr
    1655                1660                1665

Met Gln  Leu Leu Gln His Val  Lys Val Lys Asn Cys  Lys Cys Leu
    1670                1675                1680

Thr Ser  Val Phe Pro Ala Ser  Leu Ala Lys Asp Leu  Glu Lys Leu
    1685                1690                1695

Val Val  Lys Asp Cys Glu Gly  Leu Ile Glu Ile Val  Ala Glu Asp
    1700                1705                1710

Asn Ala  Asp Pro Arg Glu Ala  Asn Leu Glu Leu Thr  Phe Pro Cys
    1715                1720                1725

Pro Cys  Val Ser Ser Leu Lys  Leu Gln Gly Leu Pro  Lys Phe Lys
    1730                1735                1740

Tyr Phe  Tyr Tyr Cys Ser Leu  Gln Cys Asp Met Phe  Gln Thr Pro
    1745                1750                1755

Thr Lys  Asp Glu Met Pro Thr  Ser Asn Leu Gln Cys  Leu Ser Leu
    1760                1765                1770

Gly Glu  Lys Gly Leu Glu Met  Ile Lys Arg Ala Glu  Phe Gln Arg
    1775                1780                1785

Asn Phe  Leu His Lys Leu Gln  Val Leu Thr Leu Cys  Phe His Ile
    1790                1795                1800

Gly Ser  Asn Val Phe Pro Tyr  Glu Ile Leu Gln Leu  Ala Pro Asn
    1805                1810                1815

Ile Glu  Lys Leu Val Val Cys  Asp Gly Ser Phe Lys  Glu Ile Phe
    1820                1825                1830

Cys Phe  Asp Ser Leu Asn Val  Asp Glu Ala Gly Leu  Leu Leu Gln
    1835                1840                1845

Leu Lys  Val Leu Cys Leu Glu  Ser Leu Pro Glu Leu  Val Ser Ile
    1850                1855                1860

Gly Leu  Glu Asn Ser Trp Ile  Gln Pro Leu Leu Gly  Asn Leu Glu
    1865                1870                1875

Thr Leu  Glu Val Ile Gly Cys  Ser Ser Leu Lys Asp  Leu Val Pro
    1880                1885                1890
```

-continued

```
Ser Thr  Val Ser Phe Ser Asn  Leu Thr Tyr Leu Glu  Val Glu Arg
    1895             1900             1905

Cys His  Cys Leu Leu Tyr Leu  Phe Thr Ser Ser Thr  Ala Arg Ser
    1910             1915             1920

Leu Gly  Gln Leu Lys Arg Met  Glu Ile Lys Trp Cys  Gly Ser Ile
    1925             1930             1935

Glu Glu  Val Val Val Ser Lys  Glu Gly Asp Glu Ser  His Glu Glu
    1940             1945             1950

Glu Ile  Ile Phe Pro Gln Leu  Asn Cys Leu Lys Leu  Glu Tyr Leu
    1955             1960             1965

Ser Lys  Leu Arg Ser Phe Tyr  Lys Gly Ser Leu Leu  Ser Phe Pro
    1970             1975             1980

Ser Leu  Glu Glu Leu Ser Val  Ile Arg Cys Glu Trp  Met Glu Thr
    1985             1990             1995

Leu Cys  Pro Gly Thr Leu Lys  Ala Asp Lys Leu Val  Gln Val Gln
    2000             2005             2010

Leu Lys  Glu Ser Tyr Ser Trp  Arg His Ser Asp Pro  Ile Lys Leu
    2015             2020             2025

Glu Asn  Asp Leu Asn Ser Thr  Met Arg Glu Ala Phe  Trp Lys Lys
    2030             2035             2040

Leu Trp  Lys Ser Ala Asp Thr  Glu Phe Ser Ile Asp  Leu Lys Asp
    2045             2050             2055

Ser Pro  Val Gln Glu Ile Trp  Leu Arg Leu His Ser  Leu His Ile
    2060             2065             2070

Pro Pro  His Phe Cys Phe Pro  Lys Leu His Thr Leu  Ile Val Asp
    2075             2080             2085

Gly Cys  His Phe Leu Ser Asp  Ala Val Leu Pro Phe  Ser Leu Leu
    2090             2095             2100

Pro Leu  Leu Pro Asn Leu Lys  Thr Leu Glu Val Arg  Asn Cys Asp
    2105             2110             2115

Phe Val  Lys Ile Ile Phe Asp  Val Thr Thr Met Gly  Pro Leu Pro
    2120             2125             2130

Phe Ala  Leu Lys Thr Leu Ala  Leu Cys Asp Leu Pro  Asn Leu Glu
    2135             2140             2145

Asn Val  Trp Asn Ser Asn Val  Glu Leu Thr Phe Pro  Gln Val Lys
    2150             2155             2160

Ser Leu  Ala Leu Cys Asp Leu  Pro Lys Leu Lys Tyr  Asp Ile Leu
    2165             2170             2175

Lys Pro  Phe Thr His Leu Glu  Pro His Thr Leu Asn  Gln Val Cys
    2180             2185             2190

Ile Gln  Lys Leu Thr Pro Asn  Ile Glu His Leu Thr  Leu Gly Glu
    2195             2200             2205

His Glu  Leu Asn Met Ile Leu  Ser Gly Glu Phe Gln  Gly Asn His
    2210             2215             2220

Leu Asn  Glu Leu Lys Val Leu  Ala Leu Phe Phe His  Ile Glu Ser
    2225             2230             2235

Asp Val  Phe Leu Gln Arg Val  Pro Asn Ile Glu Lys  Leu Glu Val
    2240             2245             2250

Arg Asp  Gly Ser Phe Lys Glu  Ile Phe Cys Phe Asp  Ser Leu Asn
    2255             2260             2265

Val Asp  Glu Asp Gly Leu Val  Ser Gln Leu Lys Val  Ile Cys Pro
    2270             2275             2280
```

-continued

```
Asp Ser  Leu Pro Glu Leu Val  Ser Ile Gly Ser  Glu  Asn Ser Gly
    2285             2290             2295

Ile Val  Pro Phe Leu Arg Asn  Leu Glu Thr Leu  Gln  Val Ile Ser
    2300             2305             2310

Cys Phe  Ser Ser Ile Asn Leu  Val Pro Cys Thr  Val  Ser Phe Ser
    2315             2320             2325

Asn Leu  Thr Tyr Leu Lys Val  Glu Ser Cys Lys  Ser  Leu Leu Tyr
    2330             2335             2340

Leu Phe  Thr Ser Ser Thr Ala  Arg Ser Leu Gly  Gln  Leu Lys Thr
    2345             2350             2355

Met Glu  Ile Ser Trp Cys Asn  Ser Ile Glu Glu  Ile  Val Ser Ser
    2360             2365             2370

Thr Glu  Glu Gly Asp Glu Ser  Asp Glu Asn Glu  Ile  Ile Phe Gln
    2375             2380             2385

Gln Leu  Asn Cys Leu Lys Leu  Glu Phe Leu Phe  Lys  Leu Arg Arg
    2390             2395             2400

Phe Tyr  Lys Gly Ser Leu Ser  Phe Pro Ser Leu  Glu  Glu Phe Thr
    2405             2410             2415

Val Trp  Arg Cys Glu Arg Met  Glu Ser Leu Cys  Ala  Gly Thr Val
    2420             2425             2430

Lys Thr  Asp Lys Leu Leu Gln  Val Asn Thr Asn  Trp  Gly Gly Asp
    2435             2440             2445

Val Ile  Pro Leu Glu Thr Asp  Leu Asn Ser Ala  Met  Gln Asn Arg
    2450             2455             2460
```

```
<210> SEQ ID NO 3
<211> LENGTH: 2700
<212> TYPE: DNA
<213> ORGANISM: Glycine max

<400> SEQUENCE: 3
atggctgcaa aaacacgttc ccttgcatcc atctatgatg tgttcctcag cttcagaggt      60
ttagacacac gccatggttt cactgacaat ctctacaaag ctcttgatga caggggaatc     120
tacactttca ttgatgatca ggagtttccc agaggagacg aaataacacc tgcactttcc     180
aaggcaattc aagagtccag gattgctatt actgtgcttt ctcaaaacta tgcttcttcc     240 tcgtttttgtt tagatgaact tgtaaccatc cttcactgca agagtgaagg gctgttggtt     300
ataccggtct tttataaggt agatccttct gatgtcagac accagaaagg tagttatgga     360
gaagcaatgg ctaagcatca gaagaggttc aaagctaaga aggagaagct gcagaaatgg     420
aggatggctt tgaaacaagt agctgacttg tctggctatc atttggaaga tgggtataaa     480
accatactaa tatattttac tttatggtt ttattggatt aggttttact tgtctattga     540
tttaactagt aaaattcaaa taggaaagaa atgttcttgt taaccttgac aattattgta     600
cctatcgaga catggatgca aggattttag gctgacttca tcagaacttt ttttgtttgt     660
ttgaaacaga gatgcatatg aatacgaatt tattgggagt attgttgagg aggtctgtag     720
gaagattagt cgtgcttctt tacatgctgc ggattatcca gttgatctag agtcacaagt     780
gacaaaggta atgaagcttt tgtatcttgg atcccatgat gttgtccaca tcatagggat     840
ccatggaatg ggcgggttag gaaaaacaac acttgctcgg gcagtttata atttgattgc     900
tctccatttt gatgaatcat gttttcttca aaacgtgaga gaagaatcaa ataaacatgg     960
gttaaaacac cttcaaagca cccttctttc aaaattactt ggtgaaaagg acatcacctt    1020
aacaagttgg caagaaggag cttcaatgat acaacatagg ctccgaagaa agaagattct    1080
```

```
cttgatttta gatgatgttg acaaggacga gcaattaaag gctattgttg gaagacctga    1140
ttggtttggt cccggtagca gagtcatcat taccactcgg gacaaacatc tgctaaaatg    1200
tcacgaggtt gaaataactt ttgaggtgaa tgatttgaat tacaaagctg taacaaaatg    1260
ggaatctgct gttttatatt tttataaaag aattcccagt gatgaaatcc aagagatact    1320
aaaagtaagc tttgatgctt tggaggaaga acaaaagaat gttttttcttg atattgctta    1380 tttcttgaaa gggtataaat ggaaagaggt tgatgatata ctccgtgctc tttatggtaa    1440
ctgcaagaag catcatattg gggagttggt tgaaaaatct ctcataaagc ttaactgcta    1500
tgatggtggt actgttgaaa tgcacgacct gcttcaggac atgggtagag aaattgggcg    1560
gcagagatca ccagaagagc cctggaagtg caagagatta tggtcaccaa aagatataat    1620
tcaagtttta aaacacaaca cggtgagtga gctcatgaat agttgaattt tttttgtcta    1680
tctcatattt acatcatggt taacttttttc ttgataattt gtgaatttct ctaagcgagt    1740
caattgatat ttcacacaaa ttgtattgtg gttgattcgt gccttttttgc attagcaggg    1800 aactagtaaa attgaaatca tatgtctgga ttgctccata tctgagaaag aagaaacagt    1860
ggaatggaat gaaaacgcct tcatgaagat ggaaaacctt aaaatactta ttattagaaa    1920
tggcaaattt tccaaagctc ccagttattt tccagaaggt ttgagagtac tggaatggca    1980
cagatatcct tcaaattgtt taccatctaa ctttaatccg aacaaccttg ttatatgcaa    2040
cttacctgac agttccatga cgtcatttga gttccatggc tcatcgaagg catgtttaaa    2100
gagtatattt tcctcattgc atggctcatc gaaggcaagt ttaaagagta tattttcctc    2160
attccatgaa ttaaatttat tcatttgttt cttatttctt ttctttttttc ttttttttttg    2220 cctttgcaga agctggggca tctaacagtt ttgaattttg actggtgcaa atttttaacc    2280
cagatacctg atgtatctga tcttccaaat ttgagggaac tttcatttcg atggtgtgag    2340
agtttagttg cagttgatga gtcaattggt tttctgaaga aacttaaaat attgaatgct    2400
gctggttgca ggaagcttac gagtttttccg cctctcaact tgacctctct tgaaacactt    2460
gaactttctc actgttccag tcttgagtat tttccagaaa tattaggaga gatggaaaac    2520
ataaaggcac ttcatttgga aggccttccc ataaaagaat tgccattttc atttcaaaat    2580
cttattggac tccgtgagat aaccctgagg aggtgtagaa ttgttcggtt acgatgtagc    2640
ttagccatga tgcccaatct gtttcgattc caaattagaa attgcaacag ctggcaataa    2700
```

<210> SEQ ID NO 4
<211> LENGTH: 750
<212> TYPE: PRT
<213> ORGANISM: Glycine max

<400> SEQUENCE: 4

```
Met Ala Ala Lys Thr Arg Ser Leu Ala Ser Ile Tyr Asp Val Phe Leu
1               5                   10                  15

Ser Phe Arg Gly Leu Asp Thr Arg His Gly Phe Thr Asp Asn Leu Tyr
            20                  25                  30

Lys Ala Leu Asp Asp Arg Gly Ile Tyr Thr Phe Ile Asp Asp Gln Glu
        35                  40                  45

Phe Pro Arg Gly Asp Glu Ile Thr Pro Ala Leu Ser Lys Ala Ile Gln
    50                  55                  60

Glu Ser Arg Ile Ala Ile Thr Val Leu Ser Gln Asn Tyr Ala Ser Ser
65                  70                  75                  80

Ser Phe Cys Leu Asp Glu Leu Val Thr Ile Leu His Cys Lys Ser Glu
```

-continued

```
                  85                  90                  95
Gly Leu Leu Val Ile Pro Val Phe Tyr Lys Val Asp Pro Ser Asp Val
            100                 105                 110

Arg His Gln Lys Gly Ser Tyr Gly Glu Ala Met Ala Lys His Gln Lys
            115                 120                 125

Arg Phe Lys Ala Lys Lys Glu Lys Leu Gln Lys Trp Arg Met Ala Leu
        130                 135                 140

Lys Gln Val Ala Asp Leu Ser Gly Tyr His Leu Glu Asp Gly Asp Ala
145                 150                 155                 160

Tyr Glu Tyr Glu Phe Ile Gly Ser Ile Val Glu Glu Val Cys Arg Lys
                165                 170                 175

Ile Ser Arg Ala Ser Leu His Ala Ala Asp Tyr Pro Val Asp Leu Glu
            180                 185                 190

Ser Gln Val Thr Lys Val Met Lys Leu Leu Tyr Leu Gly Ser His Asp
            195                 200                 205

Val Val His Ile Ile Gly Ile His Gly Met Gly Gly Leu Gly Lys Thr
        210                 215                 220

Thr Leu Ala Arg Ala Val Tyr Asn Leu Ile Ala Leu His Phe Asp Glu
225                 230                 235                 240

Ser Cys Phe Leu Gln Asn Val Arg Glu Glu Ser Asn Lys His Gly Leu
                245                 250                 255

Lys His Leu Gln Ser Thr Leu Leu Ser Lys Leu Leu Gly Glu Lys Asp
            260                 265                 270

Ile Thr Leu Thr Ser Trp Gln Glu Gly Ala Ser Met Ile Gln His Arg
            275                 280                 285

Leu Arg Arg Lys Lys Ile Leu Leu Ile Leu Asp Asp Val Asp Lys Asp
        290                 295                 300

Glu Gln Leu Lys Ala Ile Val Gly Arg Pro Asp Trp Phe Gly Pro Gly
305                 310                 315                 320

Ser Arg Val Ile Ile Thr Thr Arg Asp Lys His Leu Leu Lys Cys His
                325                 330                 335

Glu Val Glu Ile Thr Phe Glu Val Asn Asp Leu Asn Tyr Lys Ala Val
            340                 345                 350

Thr Lys Trp Glu Ser Ala Val Leu Tyr Phe Tyr Lys Arg Ile Pro Ser
            355                 360                 365

Asp Glu Ile Gln Glu Ile Leu Lys Val Ser Phe Asp Ala Leu Glu Glu
        370                 375                 380

Glu Gln Lys Asn Val Phe Leu Asp Ile Ala Tyr Phe Leu Lys Gly Tyr
385                 390                 395                 400

Lys Trp Lys Glu Val Asp Asp Ile Leu Arg Ala Leu Tyr Gly Asn Cys
                405                 410                 415

Lys Lys His His Ile Gly Glu Leu Val Glu Lys Ser Leu Ile Lys Leu
            420                 425                 430

Asn Cys Tyr Asp Gly Gly Thr Val Glu Met His Asp Leu Leu Gln Asp
            435                 440                 445

Met Gly Arg Glu Ile Gly Arg Gln Arg Ser Pro Glu Glu Pro Trp Lys
        450                 455                 460

Cys Lys Arg Leu Trp Ser Pro Lys Asp Ile Ile Gln Val Leu Lys His
465                 470                 475                 480

Asn Thr Gly Thr Ser Lys Ile Glu Ile Ile Cys Leu Asp Cys Ser Ile
                485                 490                 495

Ser Glu Lys Glu Glu Thr Val Glu Trp Asn Glu Asn Ala Phe Met Lys
            500                 505                 510
```

-continued

```
Met Glu Asn Leu Lys Ile Leu Ile Ile Arg Asn Gly Lys Phe Ser Lys
        515                 520                 525

Ala Pro Ser Tyr Phe Pro Glu Gly Leu Arg Val Leu Glu Trp His Arg
    530                 535                 540

Tyr Pro Ser Asn Cys Leu Pro Ser Asn Phe Asn Pro Asn Asn Leu Val
545                 550                 555                 560

Ile Cys Asn Leu Pro Asp Ser Ser Met Thr Ser Phe Glu Phe His Gly
                565                 570                 575

Ser Ser Lys Ala Cys Leu Lys Ser Ile Phe Ser Ser Leu His Gly Ser
                580                 585                 590

Ser Lys Lys Leu Gly His Leu Thr Val Leu Asn Phe Asp Trp Cys Lys
        595                 600                 605

Phe Leu Thr Gln Ile Pro Asp Val Ser Asp Leu Pro Asn Leu Arg Glu
    610                 615                 620

Leu Ser Phe Arg Trp Cys Glu Ser Leu Val Ala Val Asp Glu Ser Ile
625                 630                 635                 640

Gly Phe Leu Lys Lys Leu Lys Ile Leu Asn Ala Ala Gly Cys Arg Lys
                645                 650                 655

Leu Thr Ser Phe Pro Pro Leu Asn Leu Thr Ser Leu Glu Thr Leu Glu
                660                 665                 670

Leu Ser His Cys Ser Ser Leu Glu Tyr Phe Pro Glu Ile Leu Gly Glu
        675                 680                 685

Met Glu Asn Ile Lys Ala Leu His Leu Glu Gly Leu Pro Ile Lys Glu
    690                 695                 700

Leu Pro Phe Ser Phe Gln Asn Leu Ile Gly Leu Arg Glu Ile Thr Leu
705                 710                 715                 720

Arg Arg Cys Arg Ile Val Arg Leu Arg Cys Ser Leu Ala Met Met Pro
                725                 730                 735

Asn Leu Phe Arg Phe Gln Ile Arg Asn Cys Asn Ser Trp Gln
                740                 745                 750
```

<210> SEQ ID NO 5
<211> LENGTH: 2661
<212> TYPE: DNA
<213> ORGANISM: Glycine max

<400> SEQUENCE: 5

```
tgtcattgtt accatatgtc gtgttactct gcgtaataat aaacattttg tatgctatct      60
ttttcatatt tgttcaagtt tgattctaca ctcccaccat atcaaccata atcatactaa     120
acttttttct tctaataatg ctgcaaaaa cacgttccct tgcatccatc tatgatgtgt     180
tcctcagctt cagaggttta gacacacgcc atggtttcac tgacaatctc tacaaagctc     240
ttgatgacag gggaatctac actttcattg atgatcagga gtttcccaga ggagacgaaa     300
taacacctgc actttccaag gcaattcaag agtccaggat tgctattact gtgctttctc     360
aaaactatgc ttcttcctcg ttttgtttag atgaacttgt aaccatcctt cactgcaaga     420
gtgaagggct gttggttata ccggtctttt ataaggtaga tccttctgat gtcagacacc     480
agaaaggtag ttatggagaa gcaatggcta agcatcagaa gaggttcaaa gctaagaagg     540
agaagctgca gaaatggagg atggctttga aacaagtagc tgacttgtct ggctatcatt     600
tggaagatgg agatgcatat gaatacgaat ttattgggag tattgttgag gaggtctgta     660
ggaagattag tcgtgcttct ttacatgctg cggattatcc agttgatcta gagtcacaag     720
tgacaaaggt aatgaagctt ttgtatcttg atcccatga tgttgtccac atcataggga     780
```

-continued

```
tccatggaat gggcgggtta ggaaaaacaa cacttgctcg ggcagtttat aatttgattg      840
ctctccattt tgatgaatca tgttttcttc aaaacgtgag agaagaatca aataaacatg      900
ggttaaaaca ccttcaaagc acccttcttt caaaattact tggtgaaaag gacatcacct      960
taacaagttg gcaagaagga gcttcaatga tacaacatag gctccgaaga aagaagattc     1020
tcttgatttt agatgatgtt gacaaggacg agcaattaaa ggctattgtt ggaagacctg     1080
attggtttgg tcccggtagc agagtcatca ttaccactcg ggacaaacat ctgctaaaat     1140
gtcacgaggt tgaaataact tttgaggtga atgatttgaa ttacaaagct gtaacaaaat     1200
gggaatctgc tgttttatat tttttataaaa gaattcccag tgatgaaatc caagagatac     1260
taaaagtaag ctttgatgct ttggaggaag aacaaaagaa tgtttttctt gatattgctt     1320
atttcttgaa agggtataaa tggaaagagg ttgatgatat actccgtgct ctttatggta     1380
actgcaagaa gcatcatatt ggggagttgg ttgaaaaatc tctcataaag cttaactgct     1440
atgatggtgg tactgttgaa atgcacgacc tgcttcagga catgggtaga gaaattgggc     1500
ggcagagatc accagaagag ccctggaagt gcaagagatt atggtcacca aaagatataa     1560
ttcaagtttt aaaacacaac acgggaacta gtaaaattga aatcatatgt ctggattgct     1620
ccatatctga gaaagaagaa acagtggaat ggaatgaaaa cgccttcatg aagatggaaa     1680
accttaaaat acttattatt agaaatggca aattttccaa agctcccagt tattttccag     1740
aaggtttgag agtactggaa tggcacagat atccttcaaa ttgtttacca tctaacttta     1800
atccgaacaa ccttgttata tgcaacttac ctgacagttc catgacgtca tttgagttcc     1860
atggctcatc gaaggcatgt ttaaagagta tattttcctc attgcatggc tcatcgaaga     1920
agctggggca tctaacagtt ttgaattttg actggtgcaa atttttaacc cagatacctg     1980
atgtatctga tcttccaaat ttgagggaac tttcatttcg atggtgtgag agtttagttg     2040
cagttgatga gtcaattggt tttctgaaga aacttaaaat attgaatgct gctggttgca     2100
ggaagcttac gagttttccg cctctcaact tgacctctct tgaaacactt gaactttctc     2160
actgttccag tcttgagtat tttccagaaa tattaggaga gatggaaaac ataaaggcac     2220
ttcatttgga aggccttccc ataaaagaat tgccatttte atttcaaaat cttattggac     2280
tccgtgagat aaccctgagg aggtgtagaa ttgttcggtt acgatgtagc ttagccatga     2340
tgcccaatct gtttcgattc caaattagaa attgcaacag ctggcaataa gtagaatcgg     2400
aagcaggtga agaaaaagtc cctccttcct acaaaccata gctttgggga cacgcaagtt     2460
ttccgtagct ttttcttat tttttttcatg tttttttattt tattattttg gtttcagttg     2520
tcaaaaattc acttaaccca actgatgttc accctatctt catcacgtac ttttgattca     2580
tttatattca tctttcacga ctttatgcat tttctatata taacctttca agttttatct     2640
ttctatatat ttttatagtt a                                               2661
```

<210> SEQ ID NO 6
<211> LENGTH: 2279
<212> TYPE: DNA
<213> ORGANISM: Glycine max

<400> SEQUENCE: 6

```
atgctggtgc cccacttaac attttctata ctatcttttt catatttgtt caagtttgat       60
tctacactcc caccatatca attaaccatt atcatactaa acttgtttct tctaataatg      120
gctgcaacga cacgttccct tgcatccatc tatgatgtgt tcctcaactt cagaggggaa      180
```

-continued

```
gacacgcgct atggttttac tggcaatctc tacaaggctc tttgtgacaa gggatttcat      240
accttctttg acgaagacaa gcttcacagc ggagaggaaa taacacctgc acttttgaag      300
gcaattcaag attccaggat tgctattatt gtgctttctg aaaactatgc ttttccctca      360
ttttgtttag atgaacttgt agccatccta cactgcaaga gggaagggct gttggttata      420
ccggtctttt acaaagtaga tccttctgat gttagacacc agaaaggtag ttatggagaa      480
gcaatgacta agcatcacga aaggttcaaa gataagatgg agaagctgca gaaatggagg      540
atggcattgc atcaagtagc tgacttgtct ggcaaacatt tcaaagatgg gtatacaatc      600
atactaatat attttacttt atggtttta ttggattatg gtttacttgt ctattgattt      660
aacttgtaaa atataaagag aaaataaatg cttgttaatc ttgacaatta atgtacctat      720
caagacatgg atgcaaggct tttaggctga cttcatcaga acttttttg tttgtttgaa      780 acagagatgc atatgaatac aagtttattg ggagtattgt tgaggagctc tctaggaaga      840
ttaatcgtgc ttctttacat gttgcggatt atcctgttgg tttagagtca caagtgacag      900
aggtaatgaa gcttttggat gttggatccg atgatgttgt ccacatcata gggatccatg      960
gaatgggcgg gttaggaaaa acaacacttg ctctggcagt atataatttc attgctctcc     1020
attttgatga atcctgtttt cttcaaaacg tgagagaaga atcaaataaa catgggttaa     1080
aacaccttca aagcatcctt ctttcaaaat tacttggtga aaggacatc atcttaacaa     1140 gttggcaaga aggagcttca atgatacaac ataggctccg acgaagaag gttctcttga     1200 ttttagacga tgttgacaag tgtgagcaat taatggctat tgttggaaga cctgattggt     1260
ttggtcccgg tagcagagtc atcattacca ctcgggacga acatctgcta aaatgtcacg     1320
aggttgaaag aacttatgag gtgaaggttt tgaatcacaa tgctgctctt caactgctta     1380
ctaggaatgc ttttaaaaga gaaaaaattg atccaagtta tgaggacgtc ttgaatcgtg     1440
tagtagctta tgcttctggc cttccattgg ctttggaagt cataggctcg gacttgtttg     1500
gaaaaactgt agcagaatgg gaatctgctg tggaacatta taaaagaatt cccagggata     1560
aaatccaaga gatactaaaa gtaagctttg atgctttggg ggaagaacaa aagaatgtgt     1620
ttcttgacat cgcttgttgc ttcaaagggt ataaatggac agaggttgat gatctactcc     1680 atgttctta tggtaactgc aagaagcatc atattggggt gttggttgaa aaatctctca     1740
taaagtacta tgatgatact gttgaaatgc acgacctgat tcaggacatg ggtagagaaa     1800
ttgagcggca gagatcacca gatgagccag ggaagcgcaa gagattatgg tcaccacaag     1860
atataattca agttttaaaa cacaacacgg tgagtgagct catgaatagt tgaatttttt     1920
tttgtctatc tcatatattt acatcatggt taactttttc tttataattc gtaatatttt     1980
ctaagcgagt caattgatat ttcacacaag ttgaattgtg gttgattcgt gccttttttgc     2040 attagcaggg aacttgtaaa attgaaatca tatgtttgga tccctccata tctgacaaag     2100
aagaaacagt ggaatggaat gaaaacgcct tcatgaagat ggaaaacctt aaaatactta     2160
ttattagaaa tggcaatttt tcgataggtc ccaataattt tccagaaggt ttgagagtac     2220
tggaatggca agatatcct tcaaattgtt taccgtctaa ctttgatccg atcaactga     2279
```

<210> SEQ ID NO 7
<211> LENGTH: 641
<212> TYPE: PRT
<213> ORGANISM: Glycine max

<400> SEQUENCE: 7

Met Leu Val Pro His Leu Thr Phe Ser Ile Leu Ser Phe Ser Tyr Leu

```
1                   5                    10                   15

Phe Lys Phe Asp Ser Thr Leu Pro Pro Tyr Gln Leu Thr Ile Ile Ile
                20                   25                   30

Leu Asn Leu Phe Leu Leu Ile Met Ala Ala Thr Thr Arg Ser Leu Ala
                35                   40                   45

Ser Ile Tyr Asp Val Phe Leu Asn Phe Arg Gly Glu Asp Thr Arg Tyr
        50                   55                   60

Gly Phe Thr Gly Asn Leu Tyr Lys Ala Leu Cys Asp Lys Gly Phe His
65                   70                   75                   80

Thr Phe Phe Asp Glu Asp Lys Leu His Ser Gly Glu Glu Ile Thr Pro
                85                   90                   95

Ala Leu Leu Lys Ala Ile Gln Asp Ser Arg Ile Ala Ile Ile Val Leu
                100                  105                  110

Ser Glu Asn Tyr Ala Phe Ser Ser Phe Cys Leu Asp Glu Leu Val Ala
                115                  120                  125

Ile Leu His Cys Lys Arg Glu Gly Leu Leu Val Ile Pro Val Phe Tyr
        130                  135                  140

Lys Val Asp Pro Ser Asp Val Arg His Gln Lys Gly Ser Tyr Gly Glu
145                  150                  155                  160

Ala Met Thr Lys His His Glu Arg Phe Lys Asp Lys Met Glu Lys Leu
                165                  170                  175

Gln Lys Trp Arg Met Ala Leu His Gln Val Ala Asp Leu Ser Gly Lys
                180                  185                  190

His Phe Lys Asp Gly Asp Ala Tyr Glu Tyr Lys Phe Ile Gly Ser Ile
                195                  200                  205

Val Glu Glu Leu Ser Arg Lys Ile Asn Arg Ala Ser Leu His Val Ala
        210                  215                  220

Asp Tyr Pro Val Gly Leu Glu Ser Gln Val Thr Glu Val Met Lys Leu
225                  230                  235                  240

Leu Asp Val Gly Ser Asp Asp Val Val His Ile Ile Gly Ile His Gly
                245                  250                  255

Met Gly Gly Leu Gly Lys Thr Thr Leu Ala Leu Ala Val Tyr Asn Phe
                260                  265                  270

Ile Ala Leu His Phe Asp Glu Ser Cys Phe Leu Gln Asn Val Arg Glu
        275                  280                  285

Glu Ser Asn Lys His Gly Leu Lys His Leu Gln Ser Ile Leu Leu Ser
        290                  295                  300

Lys Leu Leu Gly Glu Lys Asp Ile Ile Leu Thr Ser Trp Gln Glu Gly
305                  310                  315                  320

Ala Ser Met Ile Gln His Arg Leu Arg Arg Lys Lys Val Leu Leu Ile
                325                  330                  335

Leu Asp Asp Val Asp Lys Cys Glu Gln Leu Met Ala Ile Val Gly Arg
                340                  345                  350

Pro Asp Trp Phe Gly Pro Gly Ser Arg Val Ile Ile Thr Thr Arg Asp
                355                  360                  365

Glu His Leu Leu Lys Cys His Glu Val Glu Arg Thr Tyr Glu Val Lys
        370                  375                  380

Val Leu Asn His Asn Ala Ala Leu Gln Leu Leu Thr Arg Asn Ala Phe
385                  390                  395                  400

Lys Arg Glu Lys Ile Asp Pro Ser Tyr Glu Asp Val Leu Asn Arg Val
                405                  410                  415

Val Ala Tyr Ala Ser Gly Leu Pro Leu Ala Leu Glu Val Ile Gly Ser
                420                  425                  430
```

```
Asp Leu Phe Gly Lys Thr Val Ala Glu Trp Glu Ser Ala Val Glu His
        435                 440                 445

Tyr Lys Arg Ile Pro Arg Asp Lys Ile Gln Glu Ile Leu Lys Val Ser
    450                 455                 460

Phe Asp Ala Leu Gly Glu Glu Gln Lys Asn Val Phe Leu Asp Ile Ala
465                 470                 475                 480

Cys Cys Phe Lys Gly Tyr Lys Trp Thr Glu Val Asp Asp Leu Leu His
                485                 490                 495

Val Leu Tyr Gly Asn Cys Lys Lys His His Ile Gly Val Leu Val Glu
            500                 505                 510

Lys Ser Leu Ile Lys Tyr Tyr Asp Asp Thr Val Glu Met His Asp Leu
        515                 520                 525

Ile Gln Asp Met Gly Arg Glu Ile Glu Arg Gln Arg Ser Pro Asp Glu
        530                 535                 540

Pro Gly Lys Arg Lys Arg Leu Trp Ser Pro Gln Asp Ile Ile Gln Val
545                 550                 555                 560

Leu Lys His Asn Thr Gly Thr Cys Lys Ile Glu Ile Ile Cys Leu Asp
                565                 570                 575

Pro Ser Ile Ser Asp Lys Glu Glu Thr Val Glu Trp Asn Glu Asn Ala
                580                 585                 590

Phe Met Lys Met Glu Asn Leu Lys Ile Leu Ile Ile Arg Asn Gly Asn
            595                 600                 605

Phe Ser Ile Gly Pro Asn Asn Phe Pro Glu Gly Leu Arg Val Leu Glu
        610                 615                 620

Trp Gln Arg Tyr Pro Ser Asn Cys Leu Pro Ser Asn Phe Asp Pro Ile
625                 630                 635                 640

Asn
```

```
<210> SEQ ID NO 8
<211> LENGTH: 4410
<212> TYPE: DNA
<213> ORGANISM: Glycine max

<400> SEQUENCE: 8
ttttaattta tctgtgttaa cttctttctt tacatagaat ttattagtgt taactaagaa        60
ctgcatatat gctcaaagac atacacatgt cctcatatat taaaatcctt ccttgttatt       120
aggggtggaa ataggtcagg ccaaatcgct ttgaaaggtg cttaacctat gatgaatctt       180
tgaggccaga acttgaccta tagcctatca acgactttta ttttggctcg tctgacggt        240 cttttataag cctggtctga cctgatagtc tttttaaatc ttcacaataa atatttaata       300
tttcgtggag tagaaacgta ataggaaagt taaagaaaaa ggaaagtcaa tcaaaataat       360
aatgaacaat ataaatgac acatgactca cacctaaatt gtaattaaag tcaactttga        420
taagatgtgt acgcgttact agttattgtc gttattatcg tttagcctca tatgtcattg       480
tcactctgcc taataataaa catttgtgtg accgcgtcaa ataatgctgg tgccccactt       540
aacattttct atactatctt tttcatattt gttcaagttt gattctacac tcccaccata       600
tcaattaacc attatcatac taaacttgtt tcttctaata atggctgcaa cgacacgttc       660
ccttgcatcc atctatgatg tgttcctcaa cttcagaggg gaagacacgc gctatggttt       720
tactggcaat ctctacaagg ctctttgtga caagggattt catccttct ttgacgaaga        780 caagcttcac agcggagagg aaataacacc tgcactttg aaggcaattc aagattccag        840
gattgctatt attgtgcttt ctgaaaacta tgcttttcc tcatttgtt tagatgaact        900
```

-continued

```
tgtagccatc ctacactgca agagggaagg gctgttggtt ataccggtct tttacaaagt    960
agatccttct gatgttagac accagaaagg tagttatgga gaagcaatga ctaagcatca   1020
cgaaaggttc aaagataaga tggagaagct gcagaaatgg aggatggcat tgcatcaagt   1080
agctgacttg tctggcaaac atttcaaaga tggagatgca tatgaataca agtttattgg   1140
gagtattgtt gaggagctct ctaggaagat taatcgtgct tctttacatg ttgcggatta   1200
tcctgttggt ttagagtcac aagtgacaga ggtaatgaag cttttggatg ttggatccga   1260
tgatgttgtc cacatcatag ggatccatgg aatgggcggg ttaggaaaaa caacacttgc   1320
tctggcagta tataatttca ttgctctcca ttttgatgaa tcctgttttc ttcaaaacgt   1380
gagagaagaa tcaaataaac atgggttaaa acaccttcaa agcatccttc tttcaaaatt   1440
acttggtgag aaggacatca tcttaacaag ttggcaagaa ggagcttcaa tgatacaaca   1500
taggctccga cgaaagaagg ttctcttgat tttagacgat gttgacaagt gtgagcaatt   1560
aatggctatt gttggaagac ctgattggtt tggtcccggt agcagagtca tcattaccac   1620
tcgggacgaa catctgctaa aatgtcacga ggttgaaaga acttatgagg tgaaggtttt   1680
gaatcacaat gctgctcttc aactgcttac taggaatgct tttaaaagag aaaaaattga   1740
tccaagttat gaggacgtct tgaatcgtgt agtagcttat gcttctggcc ttccattggc   1800
tttggaagtc ataggctcgg acttgtttgg aaaaactgta gcagaatggg aatctgctgt   1860
ggaacattat aaaagaattc ccagggataa aatccaagag atactaaaag taagctttga   1920
tgctttgggg gaagaacaaa agaatgtgtt tcttgacatc gcttgttgct tcaaagggta   1980
taaatggaca gaggttgatg atctactcca tgttctttat ggtaactgca agaagcatca   2040
tattggggtg ttggttgaaa aatctctcat aaagtactat gatgatactg ttgaaatgca   2100
cgacctgatt caggacatgg gtagagaaat tgagcggcag agatcaccag atgagccagg   2160
gaagcgcaag agattatggt caccacaaga tataattcaa gttttaaaac acaacacggg   2220
aacttgtaaa attgaaatca tatgtttgga tccctccata tctgacaaag aagaaacagt   2280
ggaatggaat gaaaacgcct tcatgaagat ggaaaacctt aaaatactta ttattagaaa   2340
tggcaatttt tcgataggtc ccaataattt tccagaaggt ttgagagtac tggaatggca   2400
aagatatcct tcaaattgtt taccgtctaa ctttgatccg atcaactgat aggaacacag   2460
agaagacaac aacaaaggct tacacagggg tcgaaatagc agaacaggag gtgcagaagc   2520
aagccaaacc caaatggaga attacgaaac catcttacct cagtgagtat gtctgaggaa   2580
gaatggtaaa tgaatagcgg aaagcaccaa attaggaaaa gggaacatcc ttgctgagtg   2640
tgtcttcatt aggggacag cactaacaga attacaattg ccaaaccatt ctagaagctt   2700
tttctgttac tagggaaact tatatatata tatgtaaata acacagcaag gaattaatgg   2760
gaaatacttc aattaccttc tttctctgtg ccttcttctt cttcttctgt gtcttcttct   2820
tctcattttc aggggagtgc taacatcaac cttgttatat gcaagttacc tgatagttcc   2880
attacgtcat ttgagttcca tggctcatcc aagaagttgg ggcatctaac agttctgaat   2940
tttgacaagt gcaaatttt aacacagata cctgatgtat ctgatcttcc aaatttgagg   3000
gaactttcat ttcgatggtg tgagagttta gttgcagttg atgactcaat tggttttctg   3060
aataaactta aagaattgag tgctgatggt tgcaggaagc ttacgagttt tccgcctctc   3120
aacttgacct ctcttgaaac acttgaaatt tctgagtgtt ccagtcttag tattttccag   3180
aaatattagg agagatggaa aacatacaga aacttcgttt gactgacctt cccataaaaa   3240
```

-continued

```
aattgccatt ttcaattcaa aatcttactg gactccaatg gttaaccctg gggagctgtg      3300
gaattgttca gttaccatgt agcttatcca tgatgcccaa actgttggaa ttcaatatta      3360
gagattgcaa caggtggcaa tgggtagaat cggaagaagg tgaagaaaaa gtgggcccaa      3420
cacagtcttc aacggaacat tgctttggtg ccacgaagtg caatttatgt gatgattttt      3480 tttaacagg ttccaagagg tttgctcttg taacattttt agatctatcg gagaataatt       3540
tcaccatcct tcccgaattc ttcaaagaat tggaattttt acaaactctt ttcgtgagtg      3600
attgcgagca tcttcaggaa attagagggc ttccaccaaa cttagagtat tttgatgcaa      3660
gaaactgtgc atccttgact tcctcgacta aaagcatgct tttaaatcag gaactgcatg      3720
aggctagacc aacccagttt gtgtttccag gaacaagaat accagagtgg ttcgatcagc      3780
aaaagagtgg acattcaatt tctttctggt ttcgtaataa actcccagcc aaacttcttt      3840
gtcttcttat tgcactgtct actgagaatt ttatcctatc tccagacgtg ttcatcaatg      3900
gaaaatttga agaattggag ccctataaga cggacgaaat agaaagtatg tcgaaattgg      3960
atcatactta tatcttttat ctccaaaagt tacctttcaa aaatggtaat ctgtttgaag      4020
aagtggctag ggaaaaggaa tggaaccatg tggaggttag atatgaaagt gtgttagagt      4080
tagagagctc actcatcaaa ggaagtggaa tccatatatt cagagaagaa ggcagtatgg      4140
aggaagatat tcgatttgat gatccatatc tcagcagctc tgcatcagaa agcccctcct      4200
tcctacaaac catagctttg gggacacgca agttttccat tgctttttc ttatttttt          4260 catgttttt tattttatta ttttggtttc agtcttcaaa aaacgactta atccaactgg        4320
tgttcgccct atcttcataa tgtacttttg actcatttat attcatcttt catgacttta       4380
tgcattttct atatataacc tttcaagttt                                        4410

<210> SEQ ID NO 9
<211> LENGTH: 558
<212> TYPE: DNA
<213> ORGANISM: Glycine max

<400> SEQUENCE: 9
atgaagcttt tggatgttgg atccgatgat gttgtccata taatagggat ccatgggatg        60
cgtgggttag gaaaaacaac ccttgctcta gctgtttata attcgattgc tggtcatttt       120
gatgaagcct gttttcttga aaacgtgaga gaagaatcaa gtaaacatgg gttaaaacac       180
cttcaaagca tcattatttc aaaattactt ggtgagaagg acatcaactt agcaagttgg       240
caagaaggag cttcaatgat acaaagtagg ctccgacgaa agaaggttct cttgatttta       300
gacgatgtca acaagcgcga gcaattaaag gctattgttg aagatctga ttggtttggt         360 cccggtagca gagtcatcat taccactcgg gacaaatatc tgctaaaaga tcacgaggtt       420
gaaagaactt atggggtgaa ttataaattg tttggaaaaa ctgtagcaaa atgggaatct       480
gctgtcggtg attatacaaa gctcttgata tataagacag gggaatctac actttcaatg       540
atagaaggat ggctttga                                                     558

<210> SEQ ID NO 10
<211> LENGTH: 185
<212> TYPE: PRT
<213> ORGANISM: Glycine max

<400> SEQUENCE: 10

Met Lys Leu Leu Asp Val Gly Ser Asp Asp Val Val His Ile Ile Gly
1               5                   10                  15
```

-continued

```
Ile His Gly Met Arg Gly Leu Gly Lys Thr Thr Leu Ala Leu Ala Val
            20              25              30

Tyr Asn Ser Ile Ala Gly His Phe Asp Glu Ala Cys Phe Leu Glu Asn
        35              40              45

Val Arg Glu Glu Ser Ser Lys His Gly Leu Lys His Leu Gln Ser Ile
    50              55              60

Ile Ile Ser Lys Leu Leu Gly Glu Lys Asp Ile Asn Leu Ala Ser Trp
65              70              75              80

Gln Glu Gly Ala Ser Met Ile Gln Ser Arg Leu Arg Arg Lys Lys Val
                85              90              95

Leu Leu Ile Leu Asp Asp Val Asn Lys Arg Glu Gln Leu Lys Ala Ile
            100             105             110

Val Gly Arg Ser Asp Trp Phe Gly Pro Gly Ser Arg Val Ile Ile Thr
            115             120             125

Thr Arg Asp Lys Tyr Leu Leu Lys Asp His Glu Val Glu Arg Thr Tyr
    130             135             140

Gly Val Asn Tyr Lys Leu Phe Gly Lys Thr Val Ala Lys Trp Glu Ser
145             150             155             160

Ala Val Gly Asp Tyr Thr Lys Leu Leu Ile Tyr Lys Thr Gly Glu Ser
                165             170             175

Thr Leu Ser Met Ile Glu Gly Trp Leu
            180             185
```

<210> SEQ ID NO 11
<211> LENGTH: 1993
<212> TYPE: DNA
<213> ORGANISM: Glycine max

<400> SEQUENCE: 11

```
tcaagtttga ttctccctcc taccatatca accataacca tactaaactt tgttcttcta        60
ataatggctg caacgacacg ttcccttgca tccatctatg atgtgttcct cagcttcaga       120
gggacagaca cacgctatgg ttttactggc aatctctaca aggctctttg tgacaaggga       180
tttcatacct tctttgacga agacaagctt cacagcggag aggaaataac acctgcactt       240
ttgaaggcaa ttcaagattc cagggttgct attattgtgc tttctgaaaa ctatgctttt       300
tcctcatttt gtttagatga acttgtaacc atctttcact gcaagaggga agggctgttg       360
gttataccgg tcttttacaa agtcgatcct tcttatgtca gacaccagaa aggtagttat       420
ggagaagcaa tgactaagca tcaggaaagg ttcaaagata agatggagaa gctgcaggaa       480
tggaggatgg ctttgaaaca gtagctgac ttgtctggct ctcatttcaa agatggagac       540
gcatatgaat acaagtttat tgtgaatatt gttgaggagg tctctaggaa gattggtcgt       600
ggttctttac atgttgcgga ttatccggtt ggtcaagcgt cacaagtgac agaggtaatg       660
aagcttttgg atgttggatc cgatgatgtt gtccatataa tagggatcca tgggatgcgt       720
gggttaggaa aaacaaccct tgctctagct gtttataatt cgattgctgg tcattttgat       780
gaagcctgtt ttcttgaaaa cgtgagagaa gaatcaagta aacatgggtt aaaacacctt       840
caaagcatca ttatttcaaa attacttggt gagaaggaca tcaacttagc aagttggcaa       900
gaaggagctt caatgataca agtaggctc cgacgaaaga aggttctctt gattttagac       960
gatgtcaaca agcgcgagca attaaaggct attgttggaa gatctgattg gtttggtccc      1020
ggtagcagag tcatcattac cactcgggac aaatatctgc taaagatca cgaggttgaa      1080 agaacttatg gggtgaatta taaattgttt ggaaaaactg tagcaaaatg ggaatctgct      1140
```

```
gtcggtgatt atacaaagct cttgatatat aagacagggg aatctacact ttcaatgata      1200
gaaggatggc tttgaaacaa gtagctgact tgtctggctc tcatttcaaa gatgggtata      1260
caatcatact aatatatttt actttatggt ttttattgga ttaggtttta cttgtctatt      1320
gatttaacta gtcaaatta aatagaaaag aaatgctctt gttaaccttg acaattaatg       1380
tacctatcaa gacatggatg caaggatttt aggctgactt catcattacc actcgggaca      1440
aatatctgct aaaagatcac gaggttgaaa gaacttatgg ggtgaattat aaattgtttg      1500
gaaaaactgt agcaaaatgg gaatctgctg tcggtgatta tacaaagctc ttgatatata      1560
tgacagggga atctacactt tcattgatga tgaggagctt ccgagaggag acaaaataac      1620
acctgcactt ttcagttttt taaatcctca acgtcttcgt aatttctgta tcttttttgct      1680 tttaattctt tcagtttttg tatttgcagt tcataatttg aaaagaaaac atcacttcct      1740
aataattaag catgaataac tatgaataac tgctaaataa ttttttttaaa gacattttca     1800 ctttattttt cattatgaaa aacacattta tttaacagtt attaatgcat aggcctttct      1860
ccgcaaattg ttaggatccc ccagttgtag gtttgaatct taagctgctc ttttttgaaa      1920
cctgtaagag tttaagatca gaaaagatta ccatatgtat accattagaa taaatttcat      1980
cttaattcat att                                                         1993
```

```
<210> SEQ ID NO 12
<211> LENGTH: 20
<212> TYPE: DNA
<213> ORGANISM: Glycine max

<400> SEQUENCE: 12
tgtgaacatt cgtagttgtc                                                    20

<210> SEQ ID NO 13
<211> LENGTH: 20
<212> TYPE: DNA
<213> ORGANISM: Glycine max

<400> SEQUENCE: 13
ttccactgac tcacaaaaag                                                    20

<210> SEQ ID NO 14
<211> LENGTH: 20
<212> TYPE: DNA
<213> ORGANISM: Glycine max

<400> SEQUENCE: 14
tggctcatcg aaggcatgtt                                                    20

<210> SEQ ID NO 15
<211> LENGTH: 20
<212> TYPE: DNA
<213> ORGANISM: Glycine max

<400> SEQUENCE: 15
gaggtcaagt tgagaggcgg                                                    20

<210> SEQ ID NO 16
<211> LENGTH: 22
<212> TYPE: DNA
<213> ORGANISM: Glycine max

<400> SEQUENCE: 16
tcccagggat aaaatccaag ag                                                 22
```

<210> SEQ ID NO 17
<211> LENGTH: 20
<212> TYPE: DNA
<213> ORGANISM: Glycine max

<400> SEQUENCE: 17
ggtgatctct gccgctcaat                                               20

<210> SEQ ID NO 18
<211> LENGTH: 24
<212> TYPE: DNA
<213> ORGANISM: Glycine max

<400> SEQUENCE: 18
cactttcaat gatagaagga tggc                                          24

<210> SEQ ID NO 19
<211> LENGTH: 20
<212> TYPE: DNA
<213> ORGANISM: Glycine max

<400> SEQUENCE: 19
tcctctcgga agctcctcat                                               20

<210> SEQ ID NO 20
<211> LENGTH: 22
<212> TYPE: DNA
<213> ORGANISM: Glycine max

<400> SEQUENCE: 20
gcgtggcacc cttgataaat aa                                            22

<210> SEQ ID NO 21
<211> LENGTH: 24
<212> TYPE: DNA
<213> ORGANISM: Glycine max

<400> SEQUENCE: 21
gcgcacgaaa gtttttctgt aaca                                          24

<210> SEQ ID NO 22
<211> LENGTH: 20
<212> TYPE: DNA
<213> ORGANISM: Glycine max

<400> SEQUENCE: 22
ttatgaccaa tttttccccc                                               20

<210> SEQ ID NO 23
<211> LENGTH: 20
<212> TYPE: DNA
<213> ORGANISM: Glycine max

<400> SEQUENCE: 23
gaaattttga ctgccacggt                                               20

<210> SEQ ID NO 24
<211> LENGTH: 20
<212> TYPE: DNA
<213> ORGANISM: Glycine max

<400> SEQUENCE: 24

-continued

```
tgccatatgc aaattaccca                                          20

<210> SEQ ID NO 25
<211> LENGTH: 21
<212> TYPE: DNA
<213> ORGANISM: Glycine max

<400> SEQUENCE: 25
aaacattcag tcccgtcaaa a                                        21

<210> SEQ ID NO 26
<211> LENGTH: 20
<212> TYPE: DNA
<213> ORGANISM: Glycine max

<400> SEQUENCE: 26
ccactggtaa atttgggtca                                          20

<210> SEQ ID NO 27
<211> LENGTH: 25
<212> TYPE: DNA
<213> ORGANISM: Glycine max

<400> SEQUENCE: 27
caaccatgtt gttaatatga atgga                                    25

<210> SEQ ID NO 28
<211> LENGTH: 20
<212> TYPE: DNA
<213> ORGANISM: Glycine max

<400> SEQUENCE: 28
ccctcttcat ttcccttggt                                          20

<210> SEQ ID NO 29
<211> LENGTH: 22
<212> TYPE: DNA
<213> ORGANISM: Glycine max

<400> SEQUENCE: 29
cctcccaata tctttgggat aa                                        22

<210> SEQ ID NO 30
<211> LENGTH: 21
<212> TYPE: DNA
<213> ORGANISM: Glycine max

<400> SEQUENCE: 30
gcacataaca tcacccactg a                                        21

<210> SEQ ID NO 31
<211> LENGTH: 20
<212> TYPE: DNA
<213> ORGANISM: Glycine max

<400> SEQUENCE: 31
aaacagagag gcccgaagtt                                          20

<210> SEQ ID NO 32
<211> LENGTH: 26
<212> TYPE: DNA
<213> ORGANISM: Glycine max

<400> SEQUENCE: 32
```

-continued

```
gcgtcttagt cgtgctgaca ctactc                                    26

<210> SEQ ID NO 33
<211> LENGTH: 30
<212> TYPE: DNA
<213> ORGANISM: Glycine max

<400> SEQUENCE: 33
gcgagtttgt ttagctcaat ctttcactca                                30

<210> SEQ ID NO 34
<211> LENGTH: 20
<212> TYPE: DNA
<213> ORGANISM: Glycine max

<400> SEQUENCE: 34
tgtgttcttg aatgaggcga                                           20

<210> SEQ ID NO 35
<211> LENGTH: 21
<212> TYPE: DNA
<213> ORGANISM: Glycine max

<400> SEQUENCE: 35
tcagctgatg tttgaacgaa a                                         21

<210> SEQ ID NO 36
<211> LENGTH: 203
<212> TYPE: DNA
<213> ORGANISM: Glycine max

<400> SEQUENCE: 36
ttaaaataaa attcaagatg ctttatattt gcggaaagtt tgatagtctt tgaactccgg    60
attttctggc gttgatttgt gaacacgata tacccttgc caatgaattt ccagcaactt   120
caaattaacg taaactttaa atgtttgaga atgtctgtgg tagtcttaat tgtgatggag   180 ataatttta tggagacacg tgc                                         203

<210> SEQ ID NO 37
<211> LENGTH: 203
<212> TYPE: DNA
<213> ORGANISM: Glycine max

<400> SEQUENCE: 37
ttaaaataaa attcaagatg ctttatattt gcggaaagtt tgatagtctt tgaactccgg    60
attttctggc gttgatttgt gaacacgata tacccttgc cgatgaattt ccagcaactt   120
caaattaacg taaactttaa atgtttgaga atgtctgtgg tagtcttaat tgtgatggag   180 ataatttta tggagacacg tgc                                         203

<210> SEQ ID NO 38
<211> LENGTH: 203
<212> TYPE: DNA
<213> ORGANISM: Glycine max

<400> SEQUENCE: 38
aggtagccta tgttatggat aaatttatgt tatcccgcgt aatactcagt gttatgggca    60 gttctttgg gagaagaaaa aattgagata tgtttaatct ctacttctgg aattcaaatt   120
tcagccttat atcaaaacct gttaaagttt cacaaccaga tgtttcaaag gcattgaata   180
```

-continued

```
tgatttcgta tatcagtggc tat                                           203

<210> SEQ ID NO 39
<211> LENGTH: 203
<212> TYPE: DNA
<213> ORGANISM: Glycine max

<400> SEQUENCE: 39
aggtagccta tgttatggat aaatttatgt tatcccgcgt aatactcagt gttatgggca      60
gttcttttgg gagaagaaaa aattgagata tgtttaatct caacttctgg aattcaaatt     120
tcagccttat atcaaaacct gttaaagttt cacaaccaga tgtttcaaag gcattgaata     180
tgatttcgta tatcagtggc tat                                           203

<210> SEQ ID NO 40
<211> LENGTH: 203
<212> TYPE: DNA
<213> ORGANISM: Glycine max

<400> SEQUENCE: 40
ttattccccg acagatttaa atgtcctaca cgagcaaagg tcttgaaacc tgttaaaaaa      60
aaatcatcac atagattgca atccttggcc gaaaaccgat gtgcctttga agatggtatt     120
gagcccactt ttttttcacc ttcttccgat tctacccatt gccacctgtt gcaatattcc     180
atatggaatt caaacagttc ggg                                           203

<210> SEQ ID NO 41
<211> LENGTH: 203
<212> TYPE: DNA
<213> ORGANISM: Glycine max

<400> SEQUENCE: 41
ttattccccg acagatttaa atgtcctaca cgagcaaagg tcttgaaacc tgttaaaaaa      60
aaatcatcac atagattgca atccttggcc gaaaaccgat gcgcctttga agatggtatt     120
gagcccactt ttttttcacc ttcttccgat tctacccatt gccacctgtt gcaatattcc     180
atatggaatt caaacagttc ggg                                           203

<210> SEQ ID NO 42
<211> LENGTH: 203
<212> TYPE: DNA
<213> ORGANISM: Glycine max

<400> SEQUENCE: 42
ctctgttttg ccgaggagag tgtcactgca agcataactg gtacgacgga gccatcagaa      60
ccaccatata gcattttgtc ttttttctctt ccttcctccc cgctctttct cctttccttc     120
tctttcttac cttctccgtt gatgatggat ttcagatctt caattgcttc ttgcaccacc     180
atcaaccacg actttcgcat cta                                           203

<210> SEQ ID NO 43
<211> LENGTH: 203
<212> TYPE: DNA
<213> ORGANISM: Glycine max

<400> SEQUENCE: 43
ctctgttttg ccgaggagag tgtcactgca agcataactg gtacgacgga gccatcagaa      60
ccaccatata gcattttgtc ttttttctctt ccttcctccc cactctttct cctttccttc     120
tctttcttac cttctccgtt gatgatggat ttcagatctt caattgcttc ttgcaccacc     180
```

```
atcaaccacg actttcgcat cta                                                  203

<210> SEQ ID NO 44
<211> LENGTH: 203
<212> TYPE: DNA
<213> ORGANISM: Glycine max

<400> SEQUENCE: 44
tggaagtgaa gaaataaaga tattttttag atgcaagaag gaggaaactg aaaacgaagc         60
aagtagtact actgtggtgt ggtgttattt tgtttggttg tttgataata attgtaagca        120
tcagtaatgg gcagtgggtg gcagcacatg gccgccgtgc tccaccaatc accaatccaa        180
cttcgctttc ttaaatcata tcg                                                203

<210> SEQ ID NO 45
<211> LENGTH: 204
<212> TYPE: DNA
<213> ORGANISM: Glycine max

<400> SEQUENCE: 45
tggaagtgaa gaaataaaga tattttttag atgcaagaag gaggaaactg aaaacgaagc         60
aagtagtact actgtggtgt ggtgttattt tgtttggttg tcctgataat aattgtaagc        120
atcagtaatg ggcagtgggt ggcagcacat ggccgccgtg ctccaccaat caccaatcca        180
acttcgcttt cttaaatcat atcg                                               204

<210> SEQ ID NO 46
<211> LENGTH: 203
<212> TYPE: DNA
<213> ORGANISM: Glycine max

<400> SEQUENCE: 46
atataattaa attattttac aagaaattta tatccctatt tttttataaa aataatccaa         60
aatcatcaat ttcttccctt cccaatgtac tgttgacatc cctaatatat tttcaagtat        120
ttttcagtaa ctactgaatt ttttgtttca cataacaaat taaaccacac tgaaactctg        180
gcatgattat atggaattat tta                                                203

<210> SEQ ID NO 47
<211> LENGTH: 203
<212> TYPE: DNA
<213> ORGANISM: Glycine max

<400> SEQUENCE: 47
atataattaa attattttac aagaaattta tatccctatt tttttataaa aataatccaa         60
aatcatcaat ttcttccctt cccaatgtac tgttgacatc cttaatatat tttcaagtat        120
ttttcagtaa ctactgaatt ttttgtttca cataacaaat taaaccacac tgaaactctg        180
gcatgattat atggaattat tta                                                203

<210> SEQ ID NO 48
<211> LENGTH: 203
<212> TYPE: DNA
<213> ORGANISM: Glycine max

<400> SEQUENCE: 48
atccattgga aacaaataag ctttgtgttc atgttcgttt tcctgaatat ttttctagat         60
ctccgcagtg aaacattccg attgttgttg agtagaacac cccgagtacg aaaatcgttc        120
```

-continued

```
tcgaagttag tttttcgtgt tgagacgaaa tcagaaacga agccaagggc atattgggca      180
taatgttttt taatttttaa tta                                              203

<210> SEQ ID NO 49
<211> LENGTH: 203
<212> TYPE: DNA
<213> ORGANISM: Glycine max

<400> SEQUENCE: 49
atccattgga aacaaataag ctttgtgttc atgttcgttt tcctgaatat ttttctagat       60
ctccgcagtg aaacattccg attgttgttg agtagaacac cgcgagtacg aaaatcgttc      120
tcgaagttag tttttcgtgt tgagacgaaa tcagaaacga agccaagggc atattgggca      180
taatgttttt taatttttaa tta                                              203

<210> SEQ ID NO 50
<211> LENGTH: 203
<212> TYPE: DNA
<213> ORGANISM: Glycine max

<400> SEQUENCE: 50
tgcacttttt tttttttttt gaaagaaagg gtctccctaa ttatttttga ttgtaaactt       60
agccattcat tgagctgaaa taaagtatct tcaatcattg gtgaaaaagg caaagaatat      120
aaattatgaa tagaaagcct cgttaacccc gcttcacggg attccatttt atgtcaggta      180
tgacaaatta aactgcgttc agt                                              203

<210> SEQ ID NO 51
<211> LENGTH: 203
<212> TYPE: DNA
<213> ORGANISM: Glycine max

<400> SEQUENCE: 51
tgcacttttt tttttttttt gaaagaaagg gtctccctaa ttatttttga ttgtaaactt       60
agccattcat tgagctgaaa taaagtatct tcaatcattg gagaaaaagg caaagaatat      120
aaattatgaa tagaaagcct cgttaacccc gcttcacggg attccatttt atgtcaggta      180
tgacaaatta aactgcgttc agt                                              203

<210> SEQ ID NO 52
<211> LENGTH: 203
<212> TYPE: DNA
<213> ORGANISM: Glycine max

<400> SEQUENCE: 52
aattgaataa agaaaaacaa aaaaattgca aataagttga aggatatata attgaaagcg       60
gcaggacgcc gtttggtgga gacccaccaa tatgatgtag ccctcaggtc attagtggca      120
acaactccat tgttatttgt taccacaacc tagctatatc ttaatagcct caatgtcccc      180
atccttaggc ttcaagagta cta                                              203

<210> SEQ ID NO 53
<211> LENGTH: 203
<212> TYPE: DNA
<213> ORGANISM: Glycine max

<400> SEQUENCE: 53
aattgaataa agaaaaacaa aaaaattgca aataagttga aggatatata attgaaagcg       60
gcaggacgcc gtttggtgga gacccaccaa tatgatgtag ctctcaggtc attagtggca      120
```

-continued

```
acaactccat tgttatttgt taccacaacc tagctatatc ttaatagcct caatgtcccc      180
atccttaggc ttcaagagta cta                                              203

<210> SEQ ID NO 54
<211> LENGTH: 203
<212> TYPE: DNA
<213> ORGANISM: Glycine max

<400> SEQUENCE: 54
tttatggttt gagtactttc cagtaatttt tgggattatc tgttgaaata tacttatctt       60
tttttctcat cttttattct gacaaaatta tcagaattag caataacaac ttctggattg      120
gttctcgttg atgacaaatg taactaaccc actagtattt tttttgttct aactcagagc      180
cacaaaagtt ctccaaagat ggt                                              203

<210> SEQ ID NO 55
<211> LENGTH: 203
<212> TYPE: DNA
<213> ORGANISM: Glycine max

<400> SEQUENCE: 55
tttatggttt gagtactttc cagtaatttt tgggattatc tgttgaaata tacttatctt       60
tttttctcat cttttattct gacaaaatta tcagaattag cgataacaac ttctggattg      120
gttctcgttg atgacaaatg taactaaccc actagtattt tttttgttct aactcagagc      180
cacaaaagtt ctccaaagat ggt                                              203

<210> SEQ ID NO 56
<211> LENGTH: 203
<212> TYPE: DNA
<213> ORGANISM: Glycine max

<400> SEQUENCE: 56
cactgtaagt aatacagcat aacttgaaaa atgttcaaag agtactagga aaatggctac       60
tgaaggtact ttgagtttga gggtcatgcc gcctcccact ccaaatcttt ccctcgaaac      120
tgtgtccctc catttctttc tcttccttcc ctgttaaagt tcccccactt acaacctgct      180
gcatagacag acaattacaa tta                                              203

<210> SEQ ID NO 57
<211> LENGTH: 203
<212> TYPE: DNA
<213> ORGANISM: Glycine max

<400> SEQUENCE: 57
cactgtaagt aatacagcat aacttgaaaa atgttcaaag agtactagga aaatggctac       60
tgaaggtact ttgagtttga gggtcatgcc gcctcccact ctaaatcttt ccctcgaaac      120
tgtgtccctc catttctttc tcttccttcc ctgttaaagt tcccccactt acaacctgct      180
gcatagacag acaattacaa tta                                              203

<210> SEQ ID NO 58
<211> LENGTH: 203
<212> TYPE: DNA
<213> ORGANISM: Glycine max

<400> SEQUENCE: 58
caaaattttt actaaaaatc acaatatagt ttgtagtact tttttcata attttttttc       60
```

-continued

```
cacttttgat tccttttaat atgcactaaa aaatctaaaa tgactttta ttcaataaaa      120 tgatgaattg tgtttaacac caataatcat gtttgacact actttcaaag acatcaaaca      180
agtctcctgg tgttttcgga tgc                                             203

<210> SEQ ID NO 59
<211> LENGTH: 203
<212> TYPE: DNA
<213> ORGANISM: Glycine max

<400> SEQUENCE: 59
caaaattttt actaaaaatc acaatatagt ttgtagtact ttttttcata attttttttc       60
cacttttgat tccttttaat atgcactaaa aaatctaaaa taactttta ttcaataaaa      120 tgatgaattg tgtttaacac caataatcat gtttgacact actttcaaag acatcaaaca      180
agtctcctgg tgttttcgga tgc                                             203

<210> SEQ ID NO 60
<211> LENGTH: 203
<212> TYPE: DNA
<213> ORGANISM: Glycine max

<400> SEQUENCE: 60
atcaacaaca taagaagtat aacaagagaa ccaggagcgt ttttttctt tgcatgctct        60 gtttgtttgg cagagaaaaa cagggaagag tgagagaaag taggaaactt ttcaacatca      120
gtacatctca tttgaaaaac aaaacatgcc cattaaagat cagatacatt gttaaacaat      180
gcagcaagca gcaattacat ggc                                             203

<210> SEQ ID NO 61
<211> LENGTH: 203
<212> TYPE: DNA
<213> ORGANISM: Glycine max

<400> SEQUENCE: 61
atcaacaaca taagaagtat aacaagagaa ccaggagcgt ttttttctt tgcatgctct        60 gtttgtttgg cagagaaaaa cagggaagag tgagagaaag ttggaaactt ttcaacatca      120
gtacatctca tttgaaaaac aaaacatgcc cattaaagat cagatacatt gttaaacaat      180
gcagcaagca gcaattacat ggc                                             203

<210> SEQ ID NO 62
<211> LENGTH: 203
<212> TYPE: DNA
<213> ORGANISM: Glycine max

<400> SEQUENCE: 62
gaaaaggata cgtgaaagaa agcactaacc aagattatca tagaaattac aagaagaggt        60
ccagaccaaa gaacagacat aaatagtcca ctcggatcaa agtagttatg actagagaag      120
cttttccagt ttttttcccaa aaatctgttc agactctcag caagatatac accaaccact      180
gcatcaaaac aatttgtagg taa                                             203

<210> SEQ ID NO 63
<211> LENGTH: 203
<212> TYPE: DNA
<213> ORGANISM: Glycine max

<400> SEQUENCE: 63
gaaaaggata cgtgaaagaa agcactaacc aagattatca tagaaattac aagaagaggt        60
```

```
ccagaccaaa gaacagacat aaatagtcca ctcggatcaa actagttatg actagagaag       120
cttttccagt tttttcccaa aaatctgttc agactctcag caagatatac accaaccact       180
gcatcaaaac aatttgtagg taa                                               203

<210> SEQ ID NO 64
<211> LENGTH: 203
<212> TYPE: DNA
<213> ORGANISM: Glycine max

<400> SEQUENCE: 64
ttttatattt ttttatattc tattttaatt taatattttt attttttta tcctctaaat        60 taaacacacc ataagggttg aagagaggaa cggaaggaat cttgggttta aaccctccta       120
ttaatattca tattctagta ataactaaca atgattgtat ttattgaata aatgaaacaa       180
ttaataatca agagaagtca ttt                                              203

<210> SEQ ID NO 65
<211> LENGTH: 203
<212> TYPE: DNA
<213> ORGANISM: Glycine max

<400> SEQUENCE: 65
ttttatattt ttttatattc tattttaatt taatattttt attttttta tcctctaaat        60 taaacacacc ataagggttg aagagaggaa cggaaggaat cgtgggttta aaccctccta       120
ttaatattca tattctagta ataactaaca atgattgtat ttattgaata aatgaaacaa       180
ttaataatca agagaagtca ttt                                              203

<210> SEQ ID NO 66
<211> LENGTH: 20
<212> TYPE: DNA
<213> ORGANISM: Glycine max

<400> SEQUENCE: 66
aaaaatcagc acccatcgac                                                   20

<210> SEQ ID NO 67
<211> LENGTH: 20
<212> TYPE: DNA
<213> ORGANISM: Glycine max

<400> SEQUENCE: 67
agccctggcc ttattttgtt                                                   20

<210> SEQ ID NO 68
<211> LENGTH: 20
<212> TYPE: DNA
<213> ORGANISM: Glycine max

<400> SEQUENCE: 68
ctctcctttc attccccaca                                                   20

<210> SEQ ID NO 69
<211> LENGTH: 20
<212> TYPE: DNA
<213> ORGANISM: Glycine max

<400> SEQUENCE: 69
ttcttggagc ttcggaggta                                                   20
```

<210> SEQ ID NO 70
<211> LENGTH: 22
<212> TYPE: DNA
<213> ORGANISM: Glycine max

<400> SEQUENCE: 70
gaactccact taatcatctc ac                                         22

<210> SEQ ID NO 71
<211> LENGTH: 21
<212> TYPE: DNA
<213> ORGANISM: Glycine max

<400> SEQUENCE: 71
ttcactccgt cctcggcggc g                                          21

<210> SEQ ID NO 72
<211> LENGTH: 37
<212> TYPE: DNA
<213> ORGANISM: Glycine max

<400> SEQUENCE: 72
atttcctaat taagtgaaag tttgaaatgt tatatta                         37

<210> SEQ ID NO 73
<211> LENGTH: 28
<212> TYPE: DNA
<213> ORGANISM: Glycine max

<400> SEQUENCE: 73
gatttatcac actatcaaag tgtatgac                                   28

<210> SEQ ID NO 74
<211> LENGTH: 20
<212> TYPE: DNA
<213> ORGANISM: Glycine max

<400> SEQUENCE: 74
tcgcaatatt ggctacgatg                                            20

<210> SEQ ID NO 75
<211> LENGTH: 26
<212> TYPE: DNA
<213> ORGANISM: Glycine max

<400> SEQUENCE: 75
ctgaaaacaa aataaaagag aacaaa                                     26

<210> SEQ ID NO 76
<211> LENGTH: 18
<212> TYPE: DNA
<213> ORGANISM: Glycine max

<400> SEQUENCE: 76
ctctgtcccc acctctcc                                              18

<210> SEQ ID NO 77
<211> LENGTH: 18
<212> TYPE: DNA
<213> ORGANISM: Glycine max

<400> SEQUENCE: 77
catggtcagt ttgatagc                                              18

```
<210> SEQ ID NO 78
<211> LENGTH: 21
<212> TYPE: DNA
<213> ORGANISM: Glycine max

<400> SEQUENCE: 78
taagtgattc gtttgagtcc t                                             21

<210> SEQ ID NO 79
<211> LENGTH: 22
<212> TYPE: DNA
<213> ORGANISM: Glycine max

<400> SEQUENCE: 79
tatggtgtgg ctatggagat tg                                            22

<210> SEQ ID NO 80
<211> LENGTH: 21
<212> TYPE: DNA
<213> ORGANISM: Glycine max

<400> SEQUENCE: 80
gcatcaacac ttggcgcaag c                                             21

<210> SEQ ID NO 81
<211> LENGTH: 24
<212> TYPE: DNA
<213> ORGANISM: Glycine max

<400> SEQUENCE: 81
ggataatgcg ataattgttc tagc                                          24

<210> SEQ ID NO 82
<211> LENGTH: 20
<212> TYPE: DNA
<213> ORGANISM: Glycine max

<400> SEQUENCE: 82
aaatatagca ccctttagag                                               20

<210> SEQ ID NO 83
<211> LENGTH: 17
<212> TYPE: DNA
<213> ORGANISM: Glycine max

<400> SEQUENCE: 83
agcctcactc tccacat                                                  17

<210> SEQ ID NO 84
<211> LENGTH: 22
<212> TYPE: DNA
<213> ORGANISM: Glycine max

<400> SEQUENCE: 84
tttaactgaa aatactccgg ca                                            22

<210> SEQ ID NO 85
<211> LENGTH: 24
<212> TYPE: DNA
<213> ORGANISM: Glycine max

<400> SEQUENCE: 85
```

-continued tcataattta agagaccaaa ccga                                          24

<210> SEQ ID NO 86
<211> LENGTH: 23
<212> TYPE: DNA
<213> ORGANISM: Glycine max

<400> SEQUENCE: 86
ttggaattct gaaagtgttg ttg                                           23

<210> SEQ ID NO 87
<211> LENGTH: 20
<212> TYPE: DNA
<213> ORGANISM: Glycine max

<400> SEQUENCE: 87
ggaaatccaa ccccaaaaat                                               20

<210> SEQ ID NO 88
<211> LENGTH: 21
<212> TYPE: DNA
<213> ORGANISM: Glycine max

<400> SEQUENCE: 88
gcaaacttgc atcaacttca a                                             21

<210> SEQ ID NO 89
<211> LENGTH: 20
<212> TYPE: DNA
<213> ORGANISM: Glycine max

<400> SEQUENCE: 89
tccacctttt ccaacattcc                                               20

<210> SEQ ID NO 90
<211> LENGTH: 21
<212> TYPE: DNA
<213> ORGANISM: Glycine max

<400> SEQUENCE: 90
catattttcc gctcactttg c                                             21

<210> SEQ ID NO 91
<211> LENGTH: 23
<212> TYPE: DNA
<213> ORGANISM: Glycine max

<400> SEQUENCE: 91
aaattagcaa aatgcatgta ccc                                           23

<210> SEQ ID NO 92
<211> LENGTH: 20
<212> TYPE: DNA
<213> ORGANISM: Glycine max

<400> SEQUENCE: 92
tcgtcgcatg caactttta                                                20

<210> SEQ ID NO 93
<211> LENGTH: 20
<212> TYPE: DNA
<213> ORGANISM: Glycine max

<400> SEQUENCE: 93

-continued ttagctcgca acaccatcac                                                          20

<210> SEQ ID NO 94
<211> LENGTH: 20
<212> TYPE: DNA
<213> ORGANISM: Glycine max

<400> SEQUENCE: 94
aatgggttgg aaacttgcag                                                          20

<210> SEQ ID NO 95
<211> LENGTH: 22
<212> TYPE: DNA
<213> ORGANISM: Glycine max

<400> SEQUENCE: 95
tgggtacgtc aaaattagga aa                                                       22

<210> SEQ ID NO 96
<211> LENGTH: 20
<212> TYPE: DNA
<213> ORGANISM: Glycine max

<400> SEQUENCE: 96
ttctttgttt gacggtggtg                                                          20

<210> SEQ ID NO 97
<211> LENGTH: 22
<212> TYPE: DNA
<213> ORGANISM: Glycine max

<400> SEQUENCE: 97
tgactcgaac acaaaactcc tt                                                       22

<210> SEQ ID NO 98
<211> LENGTH: 20
<212> TYPE: DNA
<213> ORGANISM: Glycine max

<400> SEQUENCE: 98
tggccagaac ttgaaggaac                                                          20

<210> SEQ ID NO 99
<211> LENGTH: 21
<212> TYPE: DNA
<213> ORGANISM: Glycine max

<400> SEQUENCE: 99
tgcttattat tgcaccccat t                                                        21

<210> SEQ ID NO 100
<211> LENGTH: 20
<212> TYPE: DNA
<213> ORGANISM: Glycine max

<400> SEQUENCE: 100
tgatcccttt aacccagcaa                                                          20

<210> SEQ ID NO 101
<211> LENGTH: 20
<212> TYPE: DNA
<213> ORGANISM: Glycine max -continued

```
<400> SEQUENCE: 101
caatgacaaa aagccaacca                                                20

<210> SEQ ID NO 102
<211> LENGTH: 20
<212> TYPE: DNA
<213> ORGANISM: Glycine max

<400> SEQUENCE: 102
ttccccgatg aattatttgc                                                20

<210> SEQ ID NO 103
<211> LENGTH: 22
<212> TYPE: DNA
<213> ORGANISM: Glycine max

<400> SEQUENCE: 103
tgtgataaaa ggatccagag ca                                             22

<210> SEQ ID NO 104
<211> LENGTH: 24
<212> TYPE: DNA
<213> ORGANISM: Glycine max

<400> SEQUENCE: 104
ggtagatcca ggagcttgag tcag                                           24

<210> SEQ ID NO 105
<211> LENGTH: 24
<212> TYPE: DNA
<213> ORGANISM: Glycine max

<400> SEQUENCE: 105
gcgcatctca ctgcacttga tttt                                           24

<210> SEQ ID NO 106
<211> LENGTH: 23
<212> TYPE: DNA
<213> ORGANISM: Glycine max

<400> SEQUENCE: 106
ttcttagctg ccactattta cga                                            23

<210> SEQ ID NO 107
<211> LENGTH: 20
<212> TYPE: DNA
<213> ORGANISM: Glycine max

<400> SEQUENCE: 107
tgccatgcat acacatcctt                                                20

<210> SEQ ID NO 108
<211> LENGTH: 21
<212> TYPE: DNA
<213> ORGANISM: Glycine max

<400> SEQUENCE: 108
ttttgccacc taattgtgtc t                                              21

<210> SEQ ID NO 109
<211> LENGTH: 20
<212> TYPE: DNA
<213> ORGANISM: Glycine max
```

-continued

<400> SEQUENCE: 109
tctcacaaca ggtgagtcgg                                                    20

<210> SEQ ID NO 110
<211> LENGTH: 23
<212> TYPE: DNA
<213> ORGANISM: Glycine max

<400> SEQUENCE: 110
ccaacttgaa attactagag aaa                                                23

<210> SEQ ID NO 111
<211> LENGTH: 21
<212> TYPE: DNA
<213> ORGANISM: Glycine max

<400> SEQUENCE: 111
cttactagcg tattaaccct t                                                  21

<210> SEQ ID NO 112
<211> LENGTH: 20
<212> TYPE: DNA
<213> ORGANISM: Glycine max

<400> SEQUENCE: 112
cccattacac catgtcacca                                                    20

<210> SEQ ID NO 113
<211> LENGTH: 23
<212> TYPE: DNA
<213> ORGANISM: Glycine max

<400> SEQUENCE: 113
atccgtgtta agggatctaa ctt                                                23

<210> SEQ ID NO 114
<211> LENGTH: 20
<212> TYPE: DNA
<213> ORGANISM: Glycine max

<400> SEQUENCE: 114
ccaagtggcc taatttccaa                                                    20

<210> SEQ ID NO 115
<211> LENGTH: 21
<212> TYPE: DNA
<213> ORGANISM: Glycine max

<400> SEQUENCE: 115
ttcaagaaga gaaccgtgca t                                                  21

<210> SEQ ID NO 116
<211> LENGTH: 24
<212> TYPE: DNA
<213> ORGANISM: Glycine max

<400> SEQUENCE: 116
gccacttgac actcaaatct actt                                               24

<210> SEQ ID NO 117
<211> LENGTH: 23
<212> TYPE: DNA

-continued

```
<213> ORGANISM: Glycine max

<400> SEQUENCE: 117
ataacagatt atgagttctg cag                                    23

<210> SEQ ID NO 118
<211> LENGTH: 21
<212> TYPE: DNA
<213> ORGANISM: Glycine max

<400> SEQUENCE: 118
accctctcta gaatggtgtg t                                      21

<210> SEQ ID NO 119
<211> LENGTH: 22
<212> TYPE: DNA
<213> ORGANISM: Glycine max

<400> SEQUENCE: 119
agaagaatga aaatcaccca at                                     22

<210> SEQ ID NO 120
<211> LENGTH: 24
<212> TYPE: DNA
<213> ORGANISM: Glycine max

<400> SEQUENCE: 120
gtccactaaa atgacattgt gaaa                                   24

<210> SEQ ID NO 121
<211> LENGTH: 24
<212> TYPE: DNA
<213> ORGANISM: Glycine max

<400> SEQUENCE: 121
caggtatgga tatgtatgta tcaa                                   24

<210> SEQ ID NO 122
<211> LENGTH: 21
<212> TYPE: DNA
<213> ORGANISM: Glycine max

<400> SEQUENCE: 122
atgaactcat gtgttcaatg a                                      21

<210> SEQ ID NO 123
<211> LENGTH: 20
<212> TYPE: DNA
<213> ORGANISM: Glycine max

<400> SEQUENCE: 123
tgcacacgtt tgaattaggg                                        20
```

COMPOSITIONS AND METHODS TO INCREASE RESISTANCE TO PHYTOPHTHORA SOJAE IN SOYBEAN

CROSS REFERENCE TO RELATED APPLICATIONS

This application is a U.S. national counterpart application of international application serial No. PCT/US2021/063556 filed Dec. 15, 2021, which claims priority to the following: U.S. Provisional Patent Application Ser. No. 63/126,283, filed on Dec. 16, 2020 and U.S. Provisional Application Ser. No. 63/154,913, filed on Mar. 1, 2021, respectively, the disclosures of both of which are expressly incorporated herein by reference in their entireties.

REFERENCE TO SEQUENCE LISTING SUBMITTED ELECTRONICALLY

The official copy of the sequence listing is submitted electronically via EFS-Web as an ASCII formatted sequence listing with a file named 83005_Sequence-Listing_ST25349117 created on Dec. 13, 2021 and having a size of 94,700 bytes and is filed concurrently with the specification. The sequence listing comprised in this ASCII formatted document is part of the specification and is herein incorporated by reference in its entirety.

FIELD

This disclosure relates generally to the field of molecular biology.

BACKGROUND

Soybean diseases are major threat for soybean production, resulting in yield losses and decrease in grain quality. *Phytophthora* root and stem root (PRSR), caused by the soil-borne oomycete pathogen *Phytophthora sojae*, is one of the top five most destructive diseases leading to soybean yield loss. From 1996 to 2016, the total estimated economic loss due to PRSR was 7.4 billion USD in the United States and ranked as the third most severe soybean disease after soybean cyst nematode (SCN) and seedling disease (Bandara A Y et al. 2019). Resistance to *Phytophthora* infection is conditioned by naturally occurring variation at the Resistance to *Phytophthora sojae* (Rps) loci. As races of *Phytophthora* in the fields shift, previously effective resistance sources are breaking down, causing damage and compromised yields in grower fields.

Accordingly, there is a need to develop new compositions and methods for conferring resistance to *Phytophthora sojae*. This disclosure provides such compositions and methods.

SUMMARY

In accordance with one embodiment an isolated gene construct is provided comprising a heterologous regulatory sequence operably linked to a polynucleotide encoding a polypeptide comprising an amino acid sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 2 or 4. In one embodiment the heterologous regulatory element is a heterologous promoter. In one embodiment the isolated gene construct comprises a heterologous promoter operably linked to a polynucleotide sequence encoding a polypeptide comprising SEQ ID NOs: 2 or 4. In one embodiment the isolated gene construct comprises a heterologous promoter operably linked to a polynucleotide sequence having at least 95% sequence identity with SEQ ID NO: 1 or 3.

In one embodiment soybean plants or soybean seeds are provided comprising a targeted genetic modification increasing expression of a polynucleotide encoding a polypeptide comprising an amino acid sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 2 or 4 as compared to a control plant not comprising the targeted genetic modification. In certain embodiments, the soybean plant or a plant grown from the soybean seed comprising the targeted genetic modification has improved resistance to *Phytophthora* infection as compared to the control plant. In certain embodiments, the targeted genetic modification introduces a polynucleotide sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 1 or 3, optionally wherein said polynucleotide is operably linked to a heterologous promoter.

Further provided are plants grown from seed whose cells comprise a polynucleotide encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO: 2 or 4, and methods of plant breeding comprising crossing such soybean plants with a second soybean plant to produce a progeny seed. In certain embodiments, the second soybean plant is susceptible to the at least one race of *Phytophthora*. In certain embodiments, the progeny seed comprises the targeted genetic modification and a plant produced from the seed has increased resistance to at least one race of *Phytophthora*.

Also provided are methods for generating a *Phytophthora* resistant soybean plant comprising introducing in a regenerable soybean plant cell a polynucleotide encoding a polypeptide comprising an amino acid sequence having at least 80% sequence identity to any one of SEQ ID NOs: 2 or 4, and generating the plant wherein the plant expresses the polynucleotide and has increased resistance to *Phytophthora* as compared to a control plant not expressing the polynucleotide. In certain embodiments, the regenerable plant cell is isolated from a soybean plant susceptible to at least one race of *Phytophthora* and the plant generated has increased resistance to the at least one race of *Phytophthora*. In certain embodiments, the polynucleotide is introduced in the regenerable soybean plant cell using a targeted genetic modification Further provided are methods for generating a *Phytophthora* resistant soybean plant comprising introducing in a regenerable soybean plant cell a targeted genetic modification increasing the expression of a polynucleotide encoding a polypeptide comprising an amino acid sequence having at least 80% sequence identity to any one of SEQ ID NOs: 2 or 4, optionally at least 95% sequence identity to any one of SEQ ID NOs: 2 or 4, and generating the plant wherein the plant has increased expression of the polynucleotide and increased resistance to *Phytophthora* infection as compared to a control plant not comprising the targeted genetic modification, optionally compared to the parent plant that was used to generate the modified plant that exhibits increased expression of a polynucleotide encoding a polypeptide comprising an amino acid sequence having at least 80% sequence identity to any one of SEQ ID NOs: 2 or 4.

Also provided are soybean plants or seed comprising a recombinant DNA construct comprising a polynucleotide encoding a polypeptide comprising an amino acid sequence that is at least 80% identical to any one of SEQ ID NOs: 2 or 4, wherein the soybean seed or soybean plant has increased expression of the polynucleotide as compared to a control plant not comprising the polynucleotide, optionally wherein the DNA construct comprises a heterologous promoter operably linked to a polynucleotide encoding a polypeptide comprising an amino acid sequence that is at least 80% identical to any one of SEQ ID NOs: 2 or 4.

Further provided are methods for increasing resistance to *Phytophthora* infection in a soybean plant comprising expressing in a regenerable soybean plant cell a recombinant DNA construct comprising a polynucleotide encoding a polypeptide comprising an amino acid sequence having at least 80% sequence identity to any one of SEQ ID NOs: 2 or 4, and generating the plant wherein the plant has increased expression of the polynucleotide and increased resistance to *Phytophthora* infection as compared to a control plant not comprising the recombinant DNA construct.

Also provided are methods for identifying a soybean plant that displays increased resistance to *Phytophthora*, comprising detecting in a soybean plant or seed thereof a polynucleotide sequence encoding a polypeptide comprising an amino acid sequence that is at least 80% identical to any one of SEQ ID NOs: 2 or 4 or detecting in a soybean plant or seed thereof at least one allele of a marker locus associated with Rps11, Rps2b (also known as Rps2cas), Rps15 (also known as Rps2f), or Rps14 (also known as Rps1f).

BRIEF DESCRIPTION OF THE DRAWINGS AND THE SEQUENCE LISTING

The disclosure can be more fully understood from the following detailed description and the accompanying drawings and Sequence Listing, which form a part of this application, which are incorporated herein by reference.

FIG. 1 depicts the expression level of the twelve NBS-LRR genes across the Rps11 locus in the Rps11 donor line.

Figure 2:
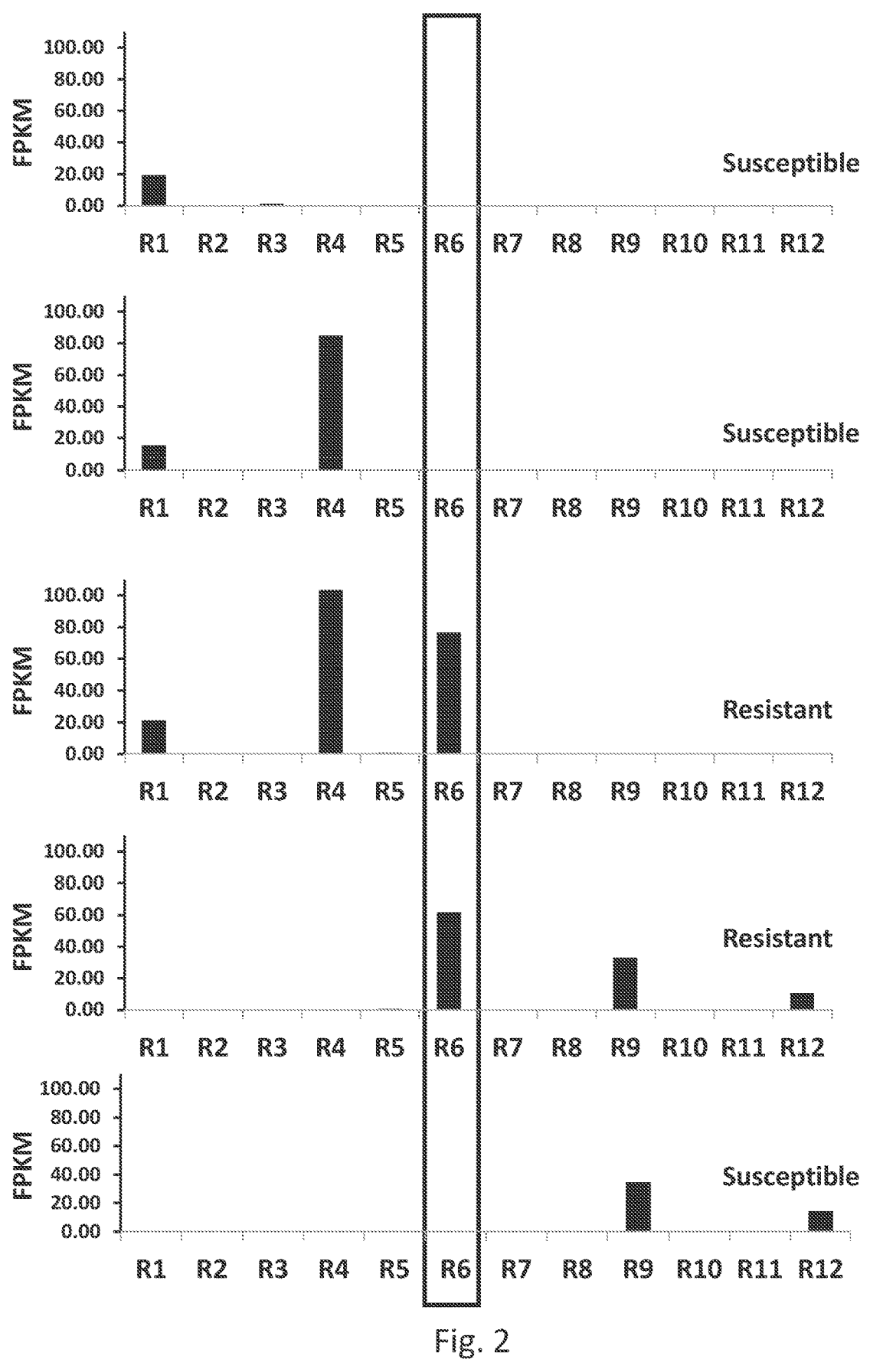

FIG. 2 provides experimental results depicting the expression profile of the NBS-LRR genes in 9 recombinants. The y-axis is the expression value in Fragments per Kilobase per Million mapped reads (FPKM) and the x-axis is the code of twelve NBS-LRR genes at Rps11 locus. The phenotype (i.e., susceptible or resistant) of each recombinant is listed and recombinants with the same expression pattern are combined together.

Figure 3:
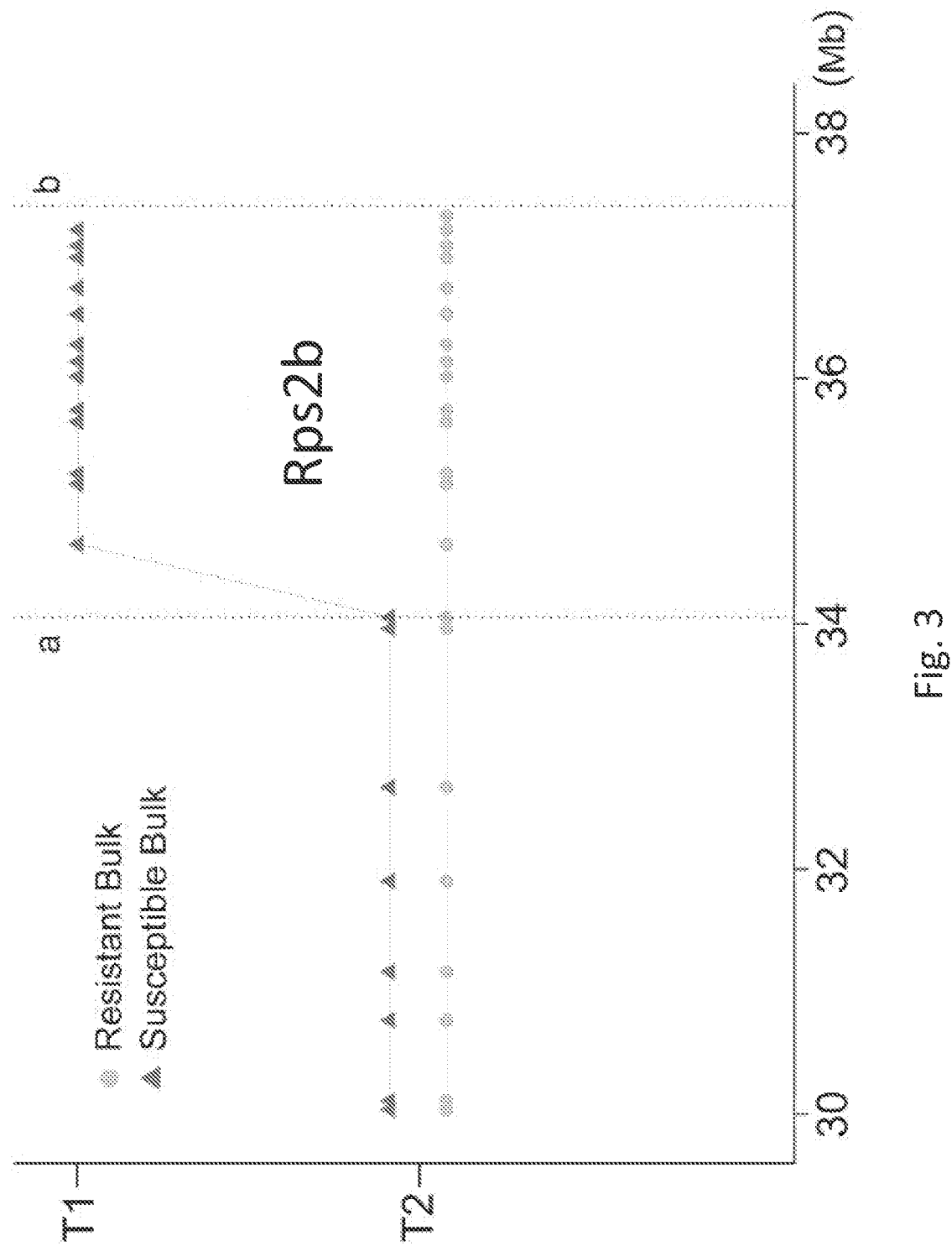

FIG. 3 provides experimental results showing the initial mapping of Rp2cas from the bulked segregant analysis (BSA). Triangles represent the genotypes of the susceptible bulk at the SNP sites between the two parental lines, while circles are genotypes of the resistant bulk at the same set of SNP sites. The x-axis shows the physical positions of these SNP sites along chromosome 16. On the y-axis, the T1 position represents the homozygous genotype detected in the susceptible bulk, and the T2 position indicates the heterozygous genotypes that were detected in susceptible or/and resistant bulks. Dotted vertical lines a and b define the two boundaries of the Rps2b region from initial BSA mapping.

Figure 4:
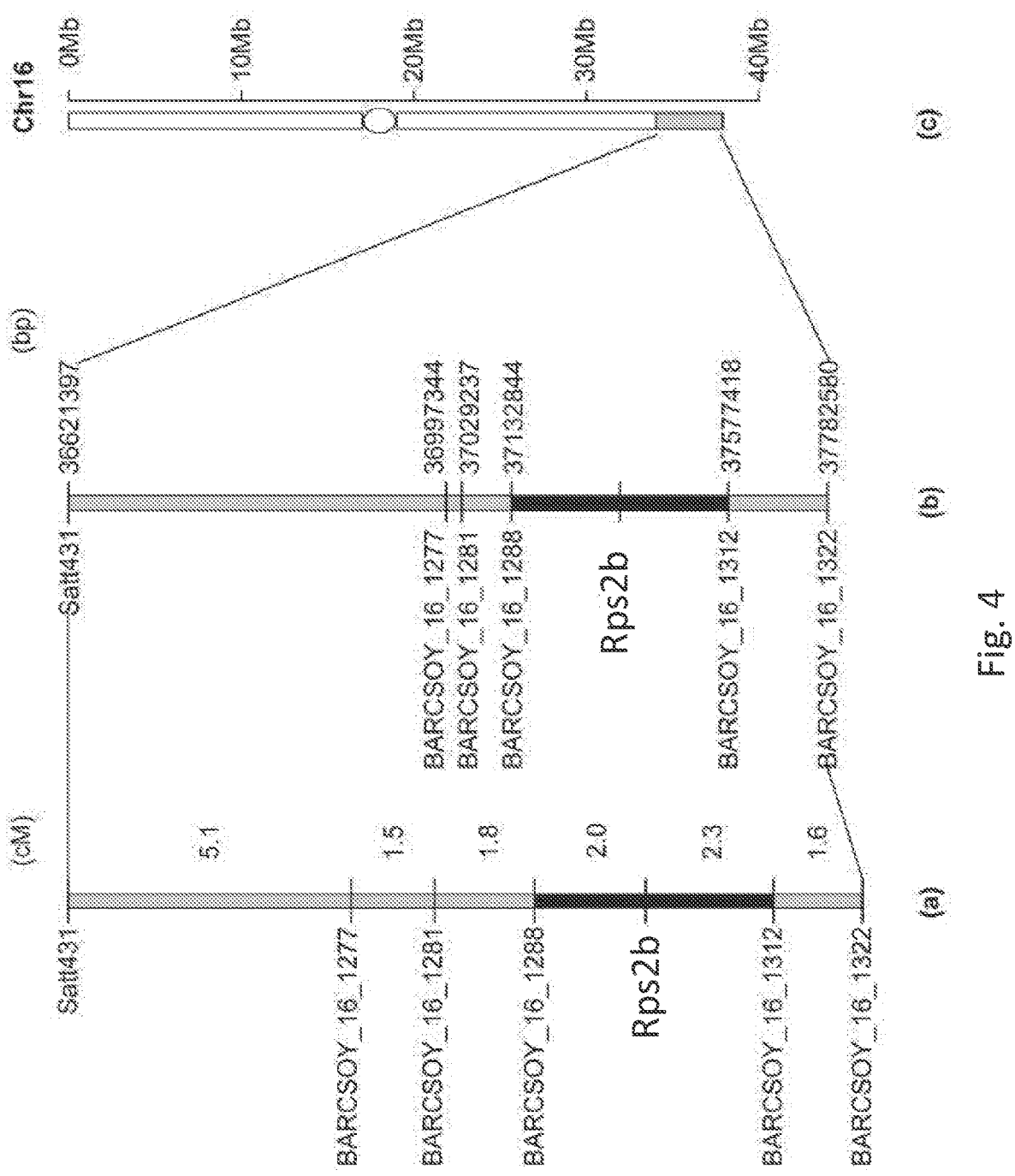

FIG. 4 provides the genetic and physical map of the Rps2b region. The left bar (a) provides the genetic map of the Rps2b region according to linkage analysis. SSR markers are listed on the left side and the genetic distance (centimorgan, cM) between adjacent markers are shown on the right side of the map. The middle bar (b) provides the physical positions of molecular markers on chromosome 16 based on soybean reference genome (Wms82 v2.1). Both genetic and physical regions of Rps2b defined by the two most closely linked markers are marked with solid dark bars. The right bar (c) provides the physical location of the Rps2b initial mapping region on Chromosome 16 based on BSA analysis. The Circle represents approximate position of centromere, whereas the two bars connected to centromere represent two arms of chromosome.

Figure 5A:
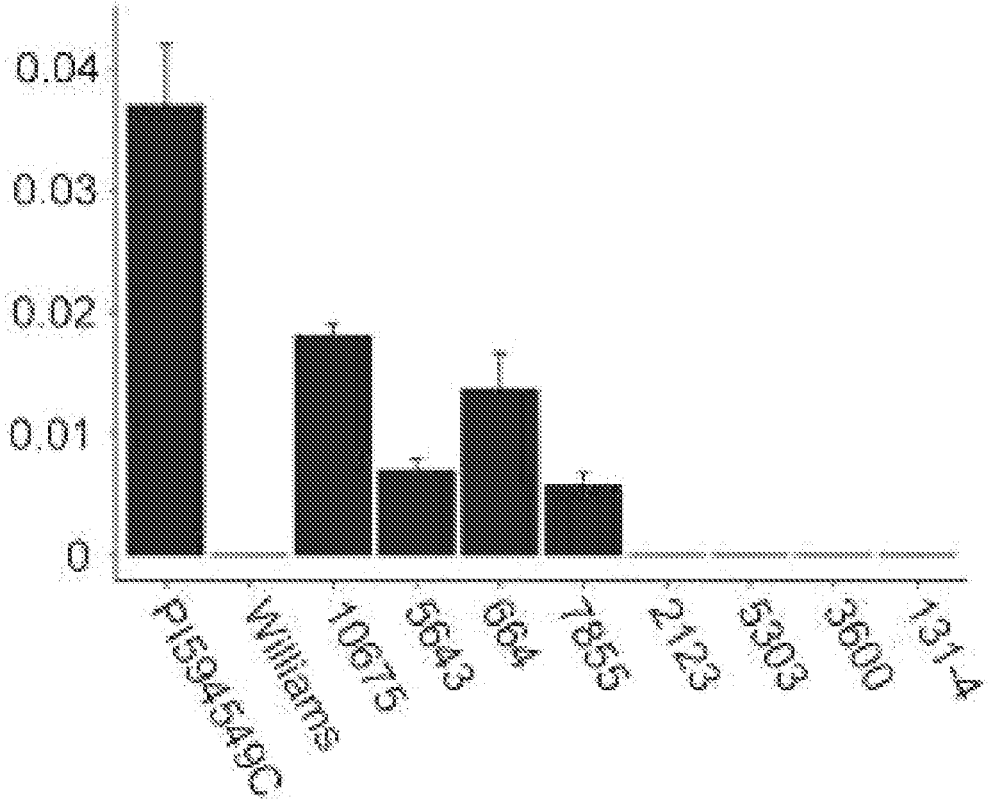
Figure 5B:
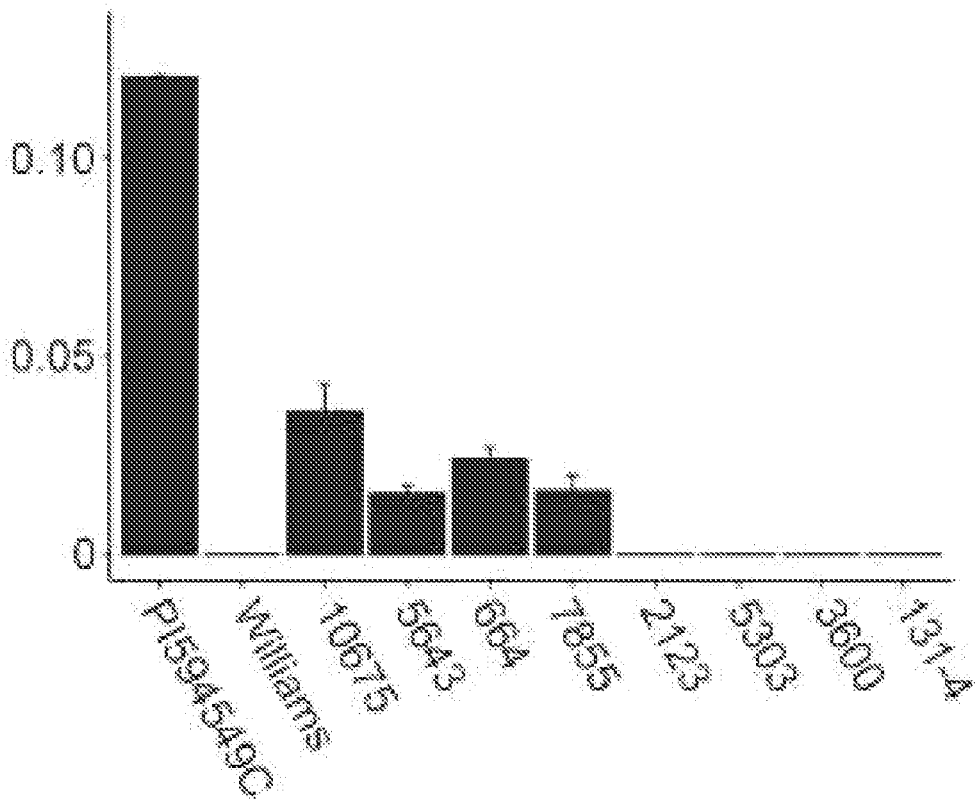
Figure 5C:
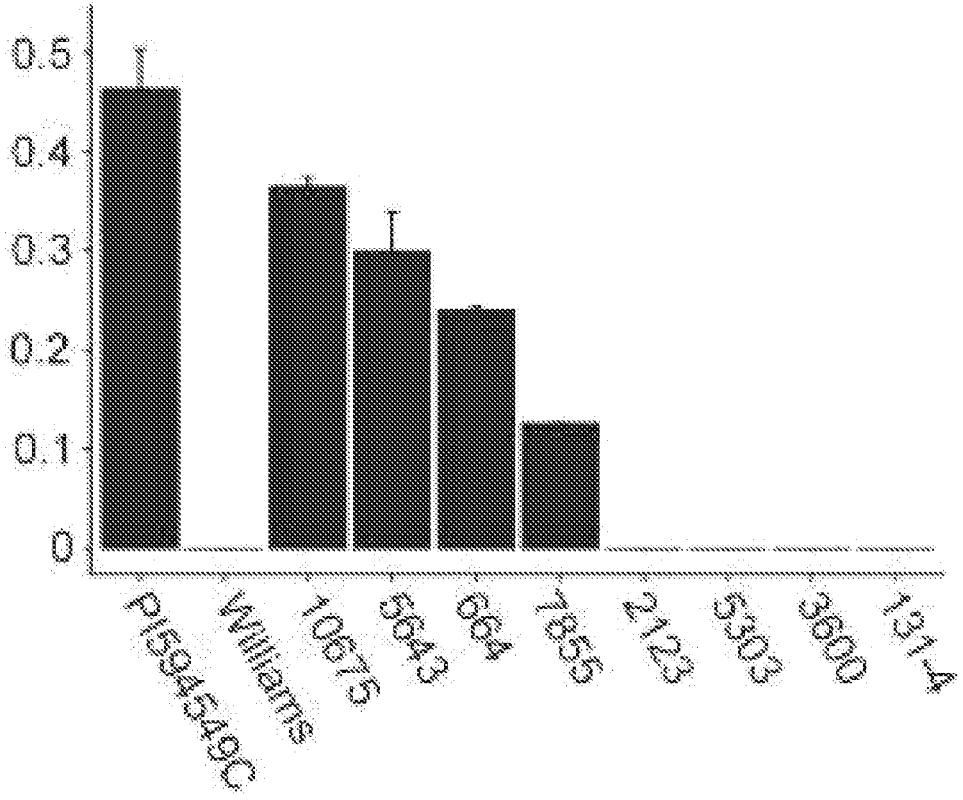

FIGS. 5A-5C provide the experimental results showing the expression pattern of the 3 tested Rps2b locus R-genes in the recombinants. The phenotype of first four recombinants (10675, 5643, 664, 7855) are all heterozygous resistance, while the phenotypes of the last four recombinants (2123, 5303, 3600, 131-4) are all susceptible. FIG. 5A provides the results of Rps2b R-gene2. FIG. 5B provides the results of Rps2b R-gene3. FIG. 5C provides the results of Rps2b R-gene4.

Figure 6A:
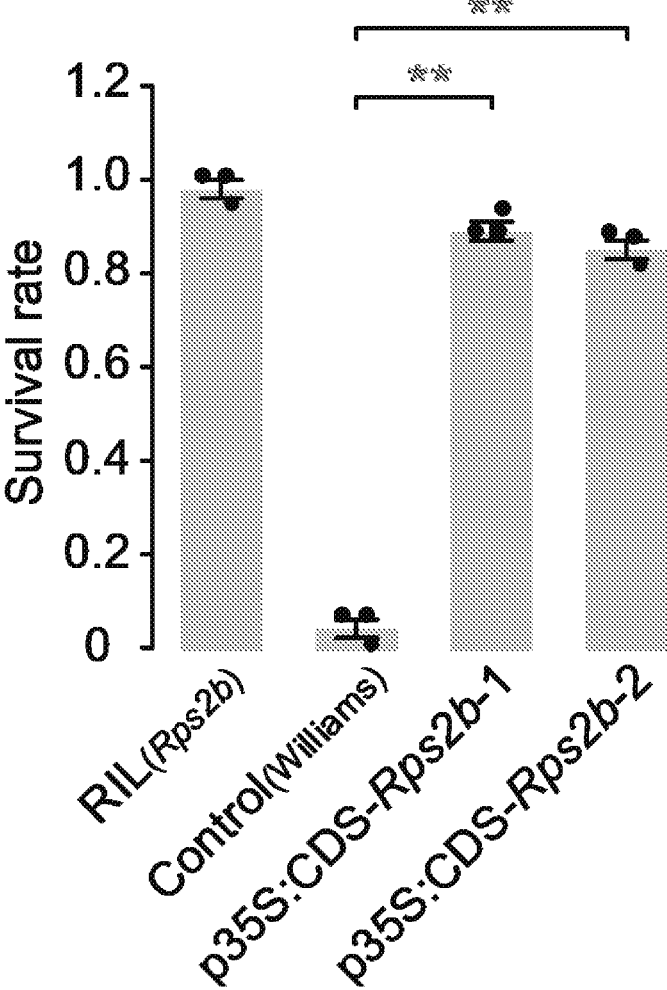
Figure 6B:
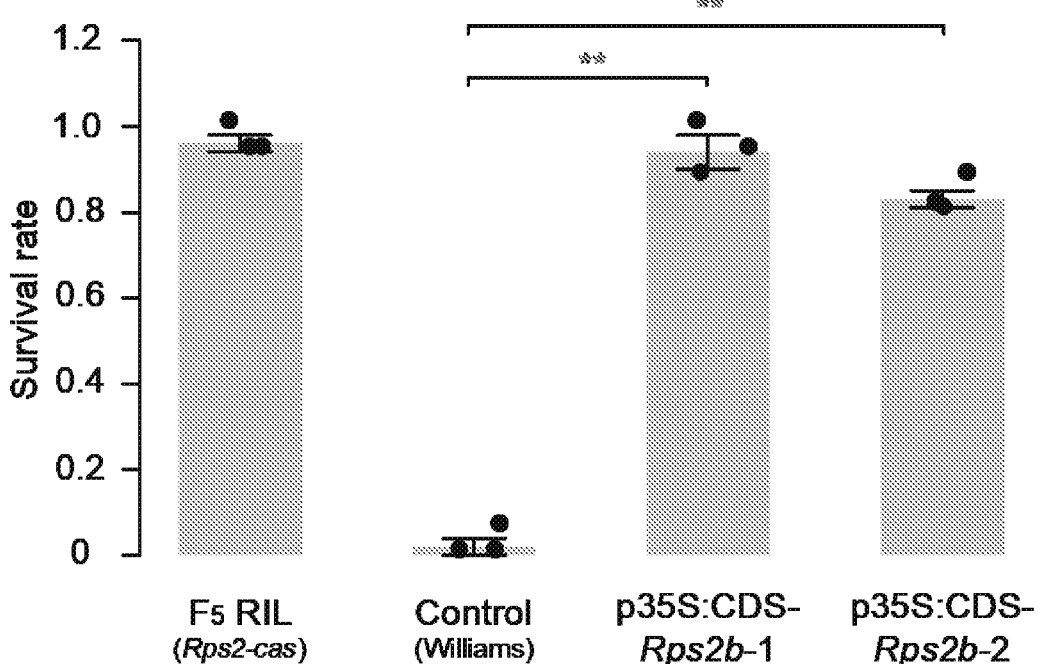

FIGS. 6A and 6B provide graphs of experimental results of a complementation test to *P. sojae* Race 1 (FIG. 6A) and Race 25 (FIG. 6B) in transgenic soybean plants expressing the Rps2b gene, soybean variety $F_5$ RIL (positive control line), or soybean Williams (negative control).

Figure 6C:
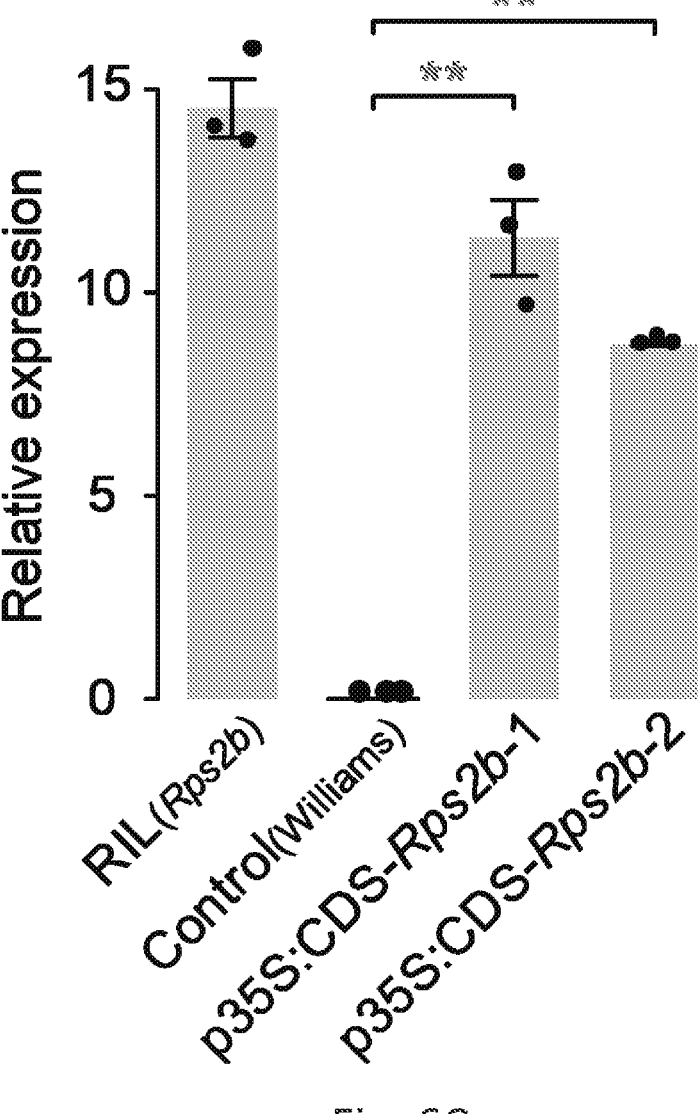

FIG. 6C provides a graph of experimental results providing the relative expression level of Rps2b in the transgenic soybean plants expressing the Rps2b gene, the soybean variety $F_5$ RIL (positive control line), and the soybean Williams (negative control).

Figure 7:
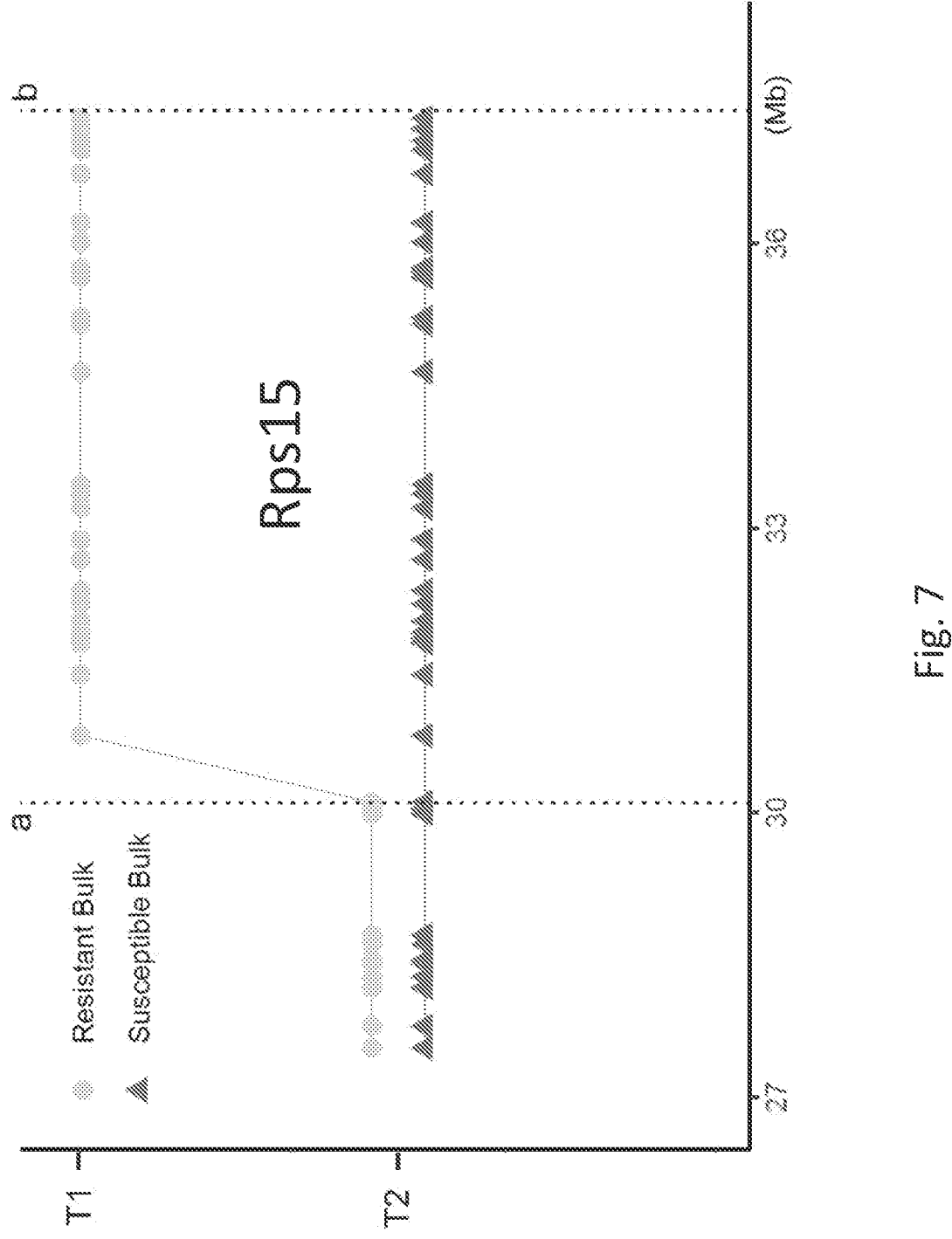

FIG. 7 provides experimental results depicting the initial mapping of Rps15 from the bulked segregant analysis (BSA). Circles represent the genotypes of the resistant bulk at the SNP sites between the two parental lines, while triangles are the genotypes of the susceptible bulk at the same set of SNP sites. The x-axis shows the physical positions of these SNP sites along chromosome 16 and on the y-axis, the T1 position represents homozygous genotype detected in the resistant bulk, and the T2 position indicates the heterozygous genotypes that were detected in susceptible or/and resistant bulks. Dotted vertical line a and b define two boundaries of Rps15 region from initial BSA mapping.

Figure 8:
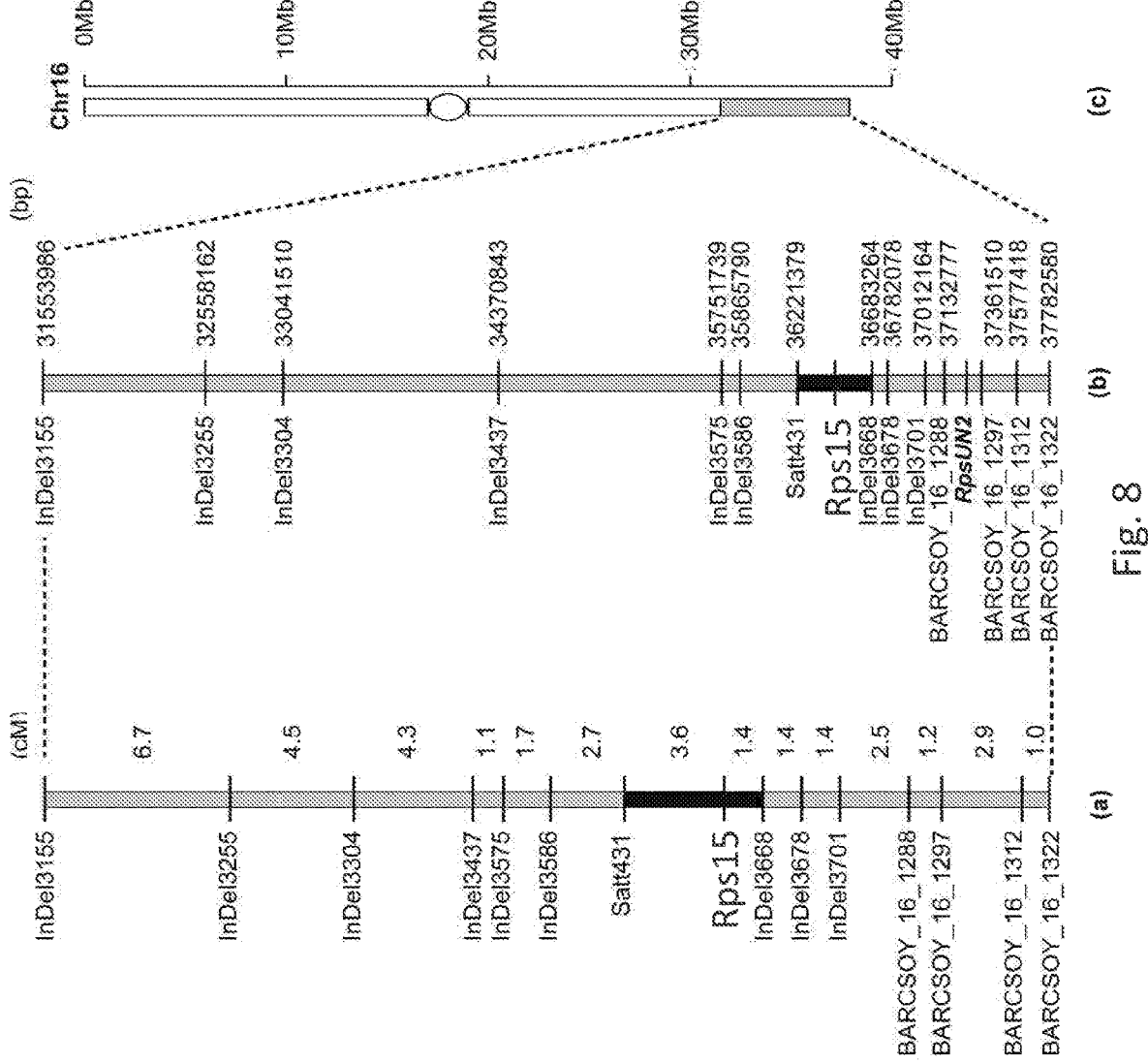

FIG. 8 provides the genetic and physical map of the Rps15 region. The left bar (a) provides a genetic map of the Rps15 region according to linkage analysis. Molecular markers (SSR/InDels) are listed on the left side and the genetic distance (centimorgan, cM) between adjacent markers are shown on the right side of the map. The center bar (b) provides the physical positions of molecular markers on chromosome 16 based on soybean reference genome (Wms82 v2.1). Both genetic and physical regions of Rps15 defined by two most closely linked markers are marked with solid dark bars. Fine mapping region of RpsUN2 is within the region defined by BARCSOY_16_1288 and BARCSOY_16_1297 (Li et al. 2016). The right bar (c) provides the physical location of the Rps15 initial mapping region on Chromosome 16 based on BSA analysis. Circle represents approximate position of centromere, whereas two bars connected to centromere represent two arms of chromosome.

Figure 9:
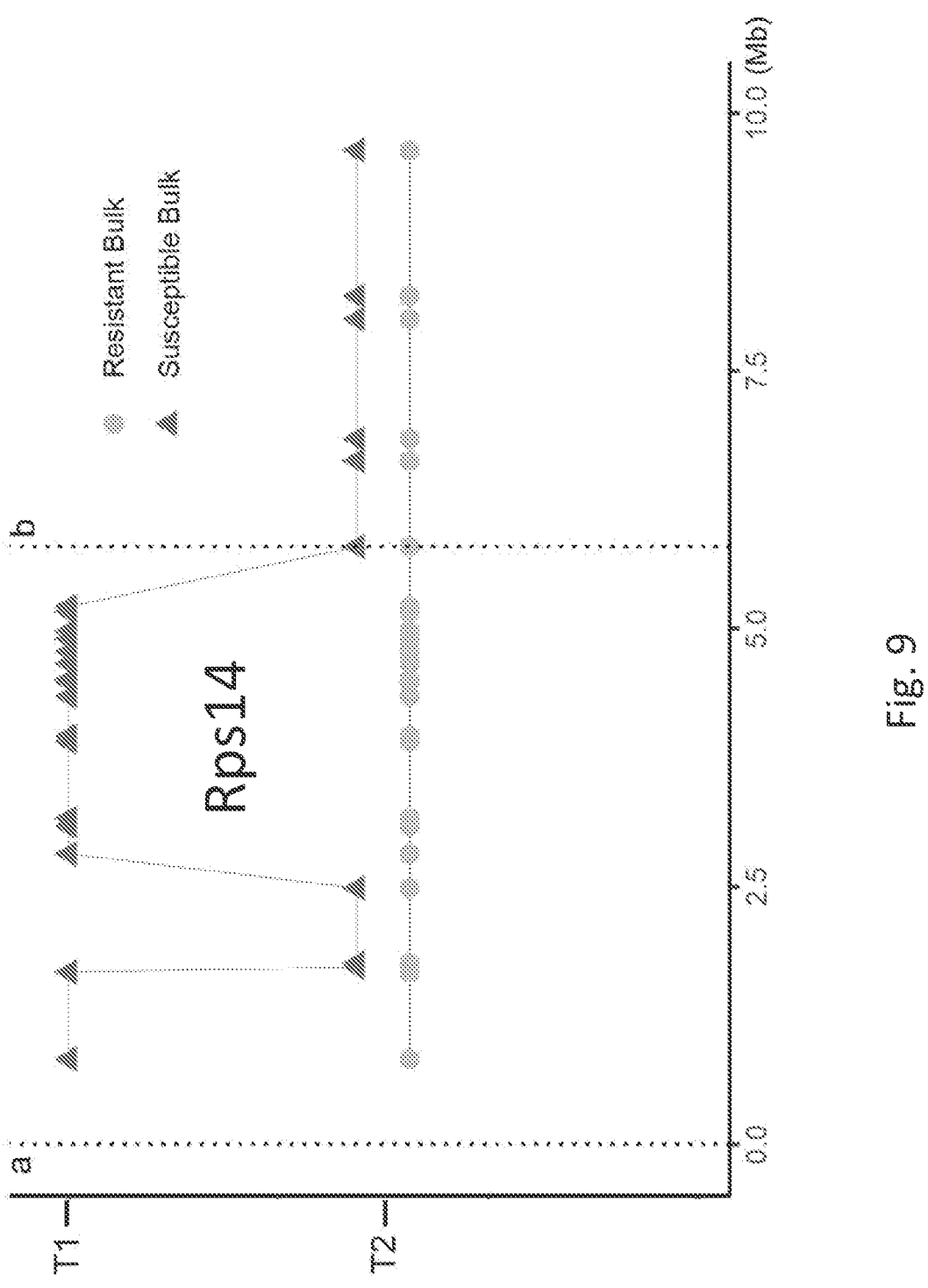

FIG. 9 provides experimental results depicting the initial mapping of Rp1f from bulked segregant analysis (BSA). Circles represent the genotypes of the resistant bulk at the SNP sites between the two parental lines, while triangles are genotypes of the susceptible bulk at the same set of SNP sites. The x-axis shows the physical positions of these SNP sites along chromosome 3 and on the y-axis, the T1 position represents homozygous genotype detected in the susceptible bulk, and the T2 position indicates the heterozygous geno-types that were detected in susceptible or/and resistant bulks. Dotted vertical line a and b define two boundaries of Rps14 region from initial BSA mapping.

Figure 10:
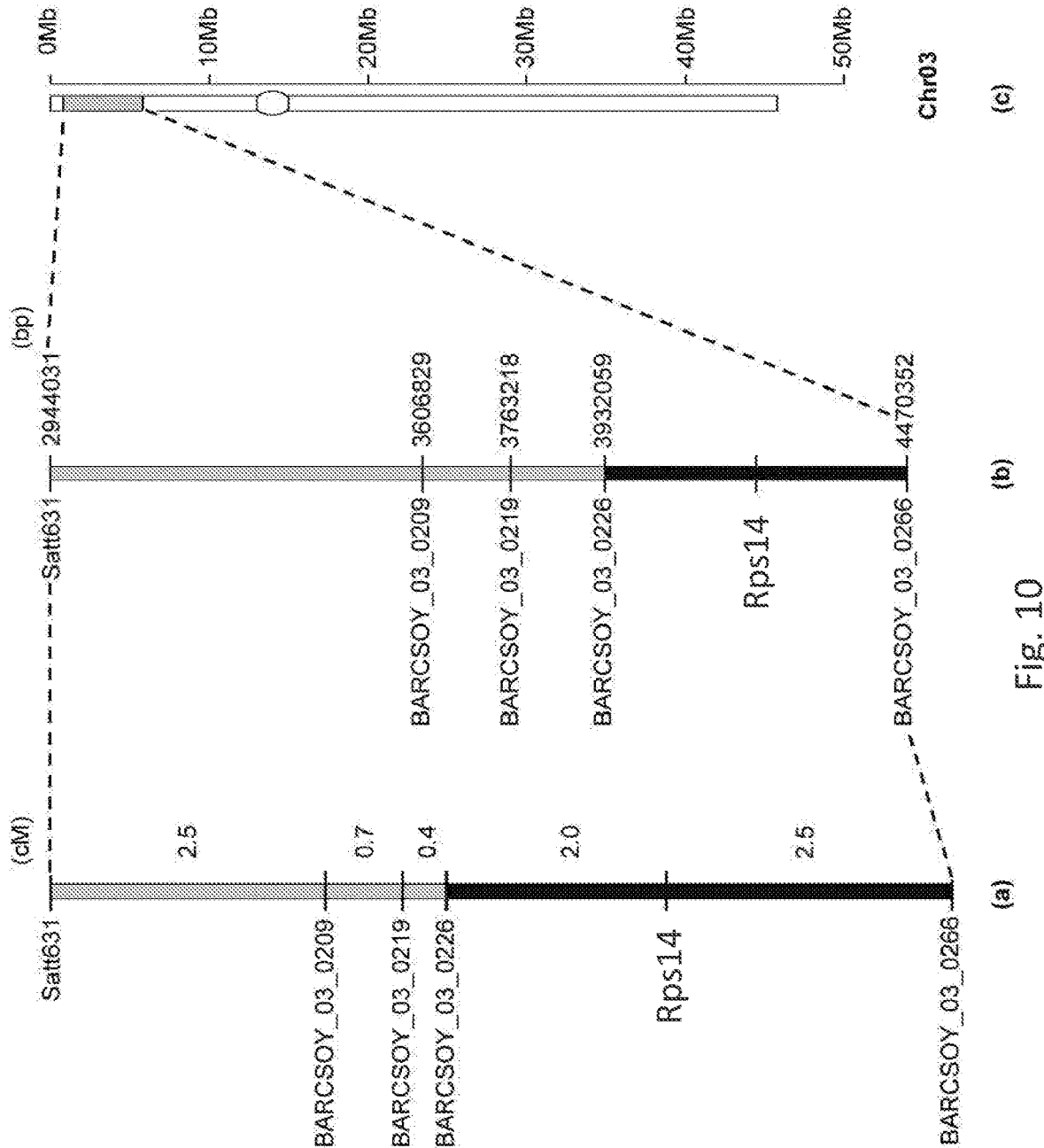

FIG. 10 provides the genetic and physical map of the Rps14 region. The left bar (a) provides the genetic map of the Rps14 region according to linkage analysis. SSR mark-ers are listed on the left side and the genetic distance (centimorgan, cM) between adjacent markers are shown on the right side of the map. The middle bar (b) provides the physical positions of molecular markers on chromosome 3 based on soybean reference genome (Wms82 v2.1). Both genetic and physical regions of Rps14 defined by two most closely linked markers are marked with solid dark bars. The right bar (c) provides the physical location of the Rps14 initial mapping region on Chromosome 3 based on BSA analysis. The circle represents approximate position of cen-tromere, whereas the two bars connected to centromere represent the two arms of the chromosome.

The sequence descriptions summarize the Sequence list-ing attached hereto, which is hereby incorporated by refer-ence and as indicated below in Table 1. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

TABLE 1

| Sequence Listing Description | | |
|---|---|---|
| Polynucleotide SEQ ID NO: | Polypeptide SEQ ID NO: | Name |
| 1 | 2 | Rps11 |
| 3, 5 | 4 | Rps2b |
| 6, 8 | 7 | Rps2b-Rgene2 |
| 9, 11 | 10 | Rps2b-Rgene4 |
| 12 | | Rps11 forward primer |
| 13 | | Rps11 reverse primer |
| 14 | | Rps2b forward primer |
| 15 | | Rps2b reverse primer |
| 16 | | Rps2b-Rgene2 forward primer |
| 17 | | Rps2b-Rgene2 reverse primer |
| 18 | | Rps2b-Rgene4 forward primer |
| 19 | | Rps2b-Rgene4 reverse primer |
| 20 | | Satt431_F |
| 21 | | Satt431_R |
| 22 | | BARCSOYSSR_16_1277_F |
| 23 | | BARCSOYSSR_16_1277_R |
| 24 | | BARCSOYSSR_16_1281_F |
| 25 | | BARCSOYSSR_16_1281_R |
| 26 | | BARCSOYSSR_16_1288_F |
| 27 | | BARCSOYSSR_16_1288_R |
| 28 | | BARCSOYSSR_16_1294_F |
| 29 | | BARCSOYSSR_16_1294_R |
| 30 | | BARCSOYSSR_16_1297_F |
| 31 | | BARCSOYSSR_16_1297_R |
| 32 | | BARCSOYSSR_16_1312_F |
| 33 | | BARCSOYSSR_16_1312_R |
| 34 | | BARCSOYSSR_16_1322_F |
| 35 | | BARCSOYSSR_16_1322_R |
| 36 | | MappingMarker-KASP-Gm16_36635129_A_G_Susceptible |
| 37 | | MappingMarker-KASP-Gm16_36635129_A_G_Resistant |
| 38 | | MappingMarker-KASP-Gm16_36641187_T_A_Susceptible |
| 39 | | MappingMarker-KASP-Gm16_36635129_A_G_Resistant |
| 40 | | MappingMarker-KASP-Gm16_36687038_T_C_Susceptible |
| 41 | | MappingMarker-KASP-Gm16_36687038_T_C_Resistant |
| 42 | | MappingMarker-KASP-Gm16_36742320_G_A_Susceptible |
| 43 | | MappingMarker-KASP-Gm16_36742320_G_A_Resistant |
| 44 | | MappingMarker-KASP-Gm16_36745870_T_C_Susceptible |
| 45 | | MappingMarker-KASP-Gm16_36745870_T_C_Resistant |
| 46 | | MappingMarker-KASP-Gm16_36789567_C_T_Susceptible |
| 47 | | MappingMarker-KASP-Gm16_36789567_C_T_Resistant |
| 48 | | MappingMarker-KASP-Gm16_36805209_C_G_Susceiptble |
| 49 | | MappingMarker-KASP-Gm16_36805209_C_G_Resistant |
| 50 | | MsppingMarker-KASP-Gm16_36818299_T_A_Susceptible |
| 51 | | MappingMarker-KASP-Gm16_36818299_T_A_Resistant |
| 52 | | MappingMarker-KASP-Gm16_36825046_C_T_Susceptible |
| 53 | | MappingMarker-KASP-Gm16_36825046_C_T_Resistant |
| 54 | | MappingMarker-KASP-Gm16_36840817_A_G_Susceptible |
| 55 | | MappingMarker-KASP-Gm16_36840817_A_G_Resistant |
| 56 | | MappingMarker-KASP-Gm16_36844181_C_T_Susceptible |
| 57 | | MappingMarker-KASP-Gm16_36844181_C_T_Resistant |
| 58 | | MappingMarker-KASP-Gm16_36849203_G_A_Susceptible |
| 59 | | MappingMarker-KASP-Gm16_36849203_G_A_Resistant |
| 60 | | MappingMarker-KASP-Gm16_36854790_A_T_Susceptible |
| 61 | | MappingMarker-KASP-Gm16_36854790_A_T_Resistant |
| 62 | | MappingMarker-KASP-Gm16_36870179_G_C_Susceptible |
| 63 | | MappingMarker-KASP-Gm16_36870179_G_C_Resistant |
| 64 | | MappingMarker-KASP-Gm16_36889339_T_G_Susceptible |

TABLE 1-continued

Sequence Listing Description

| Polynucleotide SEQ ID NO: | Polypeptide SEQ ID NO: Name |
| --- | --- |
| 65 | MappingMarker-KASP-Gm16__36889339__T__G__Resistant |
| 66 | MappingMarker-SSR-07-286F |
| 67 | MappingMarker-SSR-07-286R |
| 68 | MappingMarker-SSR-07-295F |
| 69 | MappingMarker-SSR-07-295R |
| 70 | MappingMarker-InDel-626F |
| 71 | MappingMarker-InDel-626R |
| 72 | MappingMarker-InDel-5UTR-43F |
| 73 | MappingMarker-InDel-5UTR-43R |
| 74 | MappingMarker-SSR-07-300F |
| 75 | MappingMarker-SSR-07-300R |
| 76 | MappingMarker-176kb-F |
| 77 | MappingMarker-176kb-R |
| 78 | MappingMarker-InDel-327kb-F |
| 79 | MappingMarker-InDel-327kb-R |
| 80 | MappingMarker-InDel-5.922-F |
| 81 | MappingMarker-InDel-5.922-R |
| 82 | MappingMarker-InDel-6.036-F |
| 83 | MappingMarker-InDel-6.036-R |
| 84 | MappingMarker-SSR-07-320F |
| 85 | MappingMarker-SSR-07-320R |
| 86 | InDel3155-F |
| 87 | InDel3155-R |
| 88 | InDel3255-F |
| 89 | InDel3255-R |
| 90 | InDel3304-F |
| 91 | InDel3304-R |
| 92 | InDel3437-F |
| 93 | InDel3437-R |
| 94 | InDel3575-F |
| 95 | InDel3575-R |
| 96 | InDel3568-F |
| 97 | InDel3568-R |
| 98 | InDel3668-F |
| 99 | InDel3668-R |
| 100 | InDel3678-F |
| 101 | InDel3678-R |
| 102 | InDel3701-F |
| 103 | InDel3701-R |
| 104 | Satt631-F |
| 105 | Satt631-R |
| 106 | BARCSOYSSR__03__0209-F |
| 107 | BARCSOYSSR__03__0209-R |
| 108 | BARCSOYSSR__03__0219-F |
| 109 | BARCSOYSSR__03__0219-R |
| 110 | BARCSOYSSR__03__0226-F |
| 111 | BARCSOYSSR__03__0226-R |
| 112 | BARCSOYSSR__03__0229-F |
| 113 | BARCSOYSSR__03__0229-R |
| 114 | BARCSOYSSR__03__0266-F |
| 115 | BARCSOYSSR__03__0266-R |
| 116 | InDel3971-F |
| 117 | InDel3971-R |
| 118 | InDel4033-F |
| 119 | InDel4033-R |
| 120 | InDel4263-F |
| 121 | InDel4263-R |
| 122 | InDel4330-F |
| 123 | InDel4330-R |

DETAILED DESCRIPTION

I. Compositions

A. Rps Polynucleotides and Polypeptides

One aspect of the disclosure provides a polynucleotide encoding a resistant to *Phytophthora sojae* (Rps) polypeptide comprising an amino acid sequence that is at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2, 4, 7 or 10.

As used herein "encoding," "encoded," or the like, with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma capri-*

9 colum (Yamao, et al., (1985) *Proc. Natl. Acad. Sci. USA* 82:2306-9) or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference).

The terms "polypeptide," "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

As used herein "percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

Unless otherwise stated, sequence identity/similarity values provided herein refer to the value obtained using the BLAST 2.0 suite of programs using default parameters (Altschul, et al., (1997) Nucleic Acids Res. 25:3389-402).

B. Recombinant DNA Construct

Also provided is a recombinant DNA construct comprising any of the Rps polynucleotides described herein. In certain embodiments, the recombinant DNA construct further comprises at least one regulatory element. In certain embodiments, the at least one regulatory element of the recombinant DNA construct comprises a promoter. In certain embodiments, the promoter is the native Rps polynucleotide promoter sequence. In certain embodiments, the promoter is heterologous to the Rps polynucleotide sequence.

As used herein, a "recombinant DNA construct" comprises two or more operably linked DNA segments, preferably DNA segments that are not operably linked in nature (i.e., heterologous). Non-limiting examples of recombinant DNA constructs include a polynucleotide of interest operably linked to regulatory elements, which aid in the expression, autologous replication, and/or genomic insertion of the sequence of interest. Such regulatory elements include, for example, promoters, expression modulating elements (EMEs), termination sequences, enhancers, etc., or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

The Rps polynucleotides described herein can be provided in expression cassettes for expression in a plant of interest or any organism of interest. The cassette can include 5' and 3' regulatory sequences operably linked to a Rps polynucleotide. "Operably linked" is intended to mean a functional linkage between two or more elements. For, example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the Rps polynucleotide to be under the transcriptional regulation of the regulatory regions. The expression cassette may additionally contain selectable marker genes.

The expression cassette can include in the 5'-3' direction of transcription, a transcriptional and translational initiation region (e.g., a promoter), a Rps polynucleotide, and a transcriptional and translational termination region (e.g., termination region) functional in plants. The regulatory regions (e.g., promoters, transcriptional regulatory regions, and translational termination regions) and/or the Rps polynucleotide may be native/analogous to the host cell or to each other. Alternatively, the regulatory regions and/or the Rps polynucleotide may be heterologous to the host cell or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide that is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region, with the plant host, or may be derived from another source (i.e., foreign or heterologous) than the promoter, the Rps polynucleotide, the plant host, or any combination thereof.

The expression cassette may additionally contain a 5' leader sequences. Such leader sequences can act to enhance translation. Translation leaders are known in the art and include viral translational leader sequences.

In preparing the expression cassette, the various DNA fragments may be manipulated, to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

As used herein "promoter" refers to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Certain types of promoters preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026); GOS2 (U.S. Pat. No. 6,504,083), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Also contemplated are synthetic promoters which include a combination of one or more heterologous regulatory elements.

The promoter of the recombinant DNA constructs described herein can be any type or class of promoter known in the art, such that any one of a number of promoters can be used to express the various Rps polynucleotide sequences disclosed herein, including the native promoter of the polynucleotide sequence of interest. The promoters for use in the recombinant DNA constructs of the invention can be selected based on the desired outcome.

In certain embodiments, the recombinant DNA construct, described herein, is expressed in a plant or seed. In certain embodiments, the plant or seed is a soybean plant or soybean seed. The polynucleotides or recombinant DNA constructs disclosed herein may be used for transformation of any plant species.

C. Plants and Plant Cells

Provided are plants, plant cells, plant parts, seeds, and grain comprising at least one of the Rps polynucleotide sequences or recombinant DNA constructs, described herein, so that the plants, plant cells, plant parts, seeds, and/or grain express any of the Rps polypeptides described herein. In certain embodiments, the plants, plant cells, plant parts, seeds, and/or grain have stably incorporated at least one Rps polynucleotide described herein into its genome. In certain embodiments, the plants, plant cells, plant parts, seeds and grain are soybean plants, plant cells, plant parts, seeds and grain. In certain embodiments, the plants, plant cells, plant parts, seeds, and/or grain can comprise multiple Rps polynucleotides (i.e., at least 1, 2, 3, 4, 5, 6 or more).

Also provided are plants, plant cells, plant parts, seeds, and grain comprising a targeted genetic modification increasing expression of a polynucleotide encoding a polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 2, 4, 7 or 10 as compared to a control plant not comprising the targeted genetic modification. In certain embodiments, the plants, plant cells, plant parts, seeds and grain are soybean plants, plant cells, plant parts, seeds and grain. In certain embodiments, the plant (e.g., soybean plant) comprising the targeted genetic modification has improved resistance to *Phytophthora* infection as compared to the control plant. In certain embodiments, the targeted genetic modification comprises the insertion of a polynucleotide sequence comprising and one of SEQ ID NOs: 1, 3, 6 and 9 into the genome of the plant.

"*Phytophthora*", "*Phytophthora sojae*", and "*P. sojae*" are used interchangeably herein and refer to the soil-born oomycete pathogen that is the causative agent for *Phytophthora* root and stem rot.

As used herein "increasing expression" "increased expression" or the like refers to any detectable increase in the level of the polynucleotide or encoded polypeptide as compared to a control plant (e.g., non-modified plant). The level of expression can be measure using routine methods known in the art such as PCR, Western blotting, mass spectrometry, and ELISA.

As used herein, a "targeted" genetic modification or "targeted" DNA modification, refers to the direct manipulation of an organism's genes. The targeted modification may be introduced using any technique known in the art, such as, for example, plant breeding, genome editing, or single locus conversion.

The DNA modification of the genomic locus may be done using any genome modification technique known in the art or described herein. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In certain embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

As used herein, the term "plant" includes plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the disclosure, provided that these parts comprise the introduced polynucleotides.

Also provided are plants, plant cells, plant parts, seeds, and grain comprising a polynucleotide encoding a Rps polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 2, 4, 7 or 10 operably linked to a regulatory element. In certain embodiments, the regulatory element is the native Rps promoter sequence. In certain embodiments, the regulatory element is a heterologous regulatory element, such as, for example, a heterologous promoter.

In certain embodiments, the plants described herein (e.g., plants comprising an Rps polynucleotide described herein) have a yield of soybean seeds by weight at 13% moisture that is at least 80%, 81%, 82%, 83%, 84%, 85%, 86%, 87%, 88%, 89%, 90%, 91%, 92%, 93%, 94%, 95%, 96%, 97%, 98% 99%, 100%, 101%, 102%, 103%, 104%, 105%, 106%, 107%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134% or 135% and less than 250%, 240%, 203%, 220%, 210%, 200%, 195%, 190%, 185%, 180%, 175%, 170%, 165%, 160%, 155%, 150%, 145% or 140% of the yield of seeds by weight of soybean variety 93B83 (U.S. Pat. No. 5,792,909), when grown under the same environmental conditions. Representative seed of soybean variety 93B83 were deposited under ATCC Accession No. 209766 on Apr. 10, 1998. As used herein, "under the same environmental conditions" means the plants are grown in proximity in the field or a greenhouse under non-stress conditions suitable for growth of a soybean plant to maturity, with the plants being exposed to the same environment and seeds harvested from each plant at maturity growth stage R8.

Applicant has made a deposit of at least 2500 seeds of Soybean Variety 93B83 with the American Type Culture Collection (ATCC), 10801 University Boulevard, Manassas, Va. 20110 USA, as ATCC Deposit No. 209766. The seeds were deposited with the ATCC on Apr. 10, 1998 have been accepted under the Budapest Treaty. This deposit of the Soybean Variety 93B83 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R.§§ 1.801-1.809. Upon allowance of any claims in the application, the Applicant(s) will maintain and will make this deposit available to the public pursuant to the Budapest Treaty.

As used herein, "yield" refers to the amount of agricultural production harvested per unit of land and may include reference to bushels per acre or kilograms per hectare of a crop at harvest, as adjusted for grain moisture. Grain moisture is measured in the grain at harvest. The adjusted test weight of grain is determined to be the weight in pounds per bushel or kilogram, adjusted for grain moisture level at harvest.

II. Methods

A. Methods for Increasing *Phytophthora* Resistance

Provided are methods for generating a *Phytophthora* resistant soybean plant or increasing resistance to *Phytophthora* in a soybean plant comprising expressing in a soybean plant a polynucleotide encoding a Rps polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 2, 4, 7 or 10.

"Resistance" and "improved resistance" are used interchangeably herein and refer to any type of increase in resistance or tolerance to, or any type of decrease in susceptibility. A "resistant plant" or "resistant plant variety" need not possess absolute or complete resistance. Instead, a "resistant plant," "resistant plant variety," or a plant or plant variety with "improved tolerance" will have a level of resistance or tolerance which is higher than that of a comparable susceptible plant or variety. A person of ordinary skill in the art can readily identify plants having resistance or improved resistance to *Phytophthora* using methods known in the art.

The plants of the compositions and methods described herein can have resistance or improved resistance to any race or isolate of *Phytophthora sojae* known in the art (e.g., any one of races 1 to 55). In certain embodiments, the plants are resistant or have improved resistance to at least 1, 2, 3, 4, 5, 6, 7, 8, 9, 10, 11, 12, 13, 14, 15, 16, 17, 18, 19, 20 races and/or isolates of *Phytophthora sojae*. In certain embodiments, the plants are resistant or have improved resistance to at least one, at least two, at least three, at least four, at least five, at least six, at least seven, at least eight, at least nine, or at least 10 races and/or isolates of *Phytophthora sojae* selected from the group consisting of Race1, Race 2, Race3, Race4, Race5, Race6, Race7, Race8, Race9 Race13, Race17, Race25, Race31, OH001, OHC2S1, OH003, ISA19A-1, ISA71D-1, MIN12001.01.05, MIN12002.01.05, MIN12002.05.01, MIN12002.05.05, MIN12004.01.01, MIN12004.03.01, MIN12005.07.02. In certain embodiments, the plant has resistance to Race1, Race3, Race4, Race7, Race13, Race17, Race25, ISA19A-1, ISA71D-1, MIN12001.01.05, MIN12004.01.01, MIN12004.03.01, MIN12005.07.02. In certain embodiments, the plant has resistance to Race1, Race 2, Race3, Race4, Race5, Race6, Race7, Race8, Race9, Race13, Race17, Race25, ISA19A-1, ISA71D-1, MIN12001.01.05, MIN12004.01.01, MIN12004.03.01, MIN12005.07.02. In certain embodiments, the plant has resistance to Race1, Race3, Race4, Race7, Race13, Race17, Race25, Race31, OH001, OHC2S1, OH003, MIN12002.01.05, MIN12002.05.01, MIN12002.05.05, ISA19A-1, ISA71D-1, MIN12001.01.05, MIN12004.01.01, MIN12004.03.01, MIN12005.07.02.

In certain embodiments, the method comprises introducing in a regenerable soybean plant cell a targeted genetic modification increasing the expression of a polynucleotide encoding a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 2, 4, 7 or 10 and generating the plant wherein the plant has increased expression of the polynucleotide and increased resistance to *Phytophthora* infection as compared to a control plant not comprising the targeted genetic modification. In certain embodiments, the method comprises introducing in a regenerable soybean plant cell a targeted genetic modification that inserts an exogenous polynucleotide into the plant cell genome, wherein the exogenous polynucleotide encodes a polypeptide comprising an amino acid sequence having at least 95%, 96%, 97%, 98%, or 99% sequence identity to SEQ ID NOs: 2, or 4 and generating the plant from the transformed plant cell, wherein the generated plant expresses the polynucleotide and has increased resistance to

*Phytophthora* infection as compared to a control plant not comprising the exogenous polynucleotide.

In certain embodiments, the method comprises introducing in a regenerable soybean plant cell isolated from a soybean plant susceptible to at least one race of *Phytophthora* a polynucleotide encoding a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 2, 4, 7 or 10, and generating the plant wherein the plant expresses the polynucleotide and is resistant to the at least one race of *Phytophthora* as compared to a control plant not expressing the polynucleotide. In certain embodiments, the polynucleotide is introduced in the regenerable soybean plant cell using a targeted genetic modification. In certain embodiments, the polynucleotide is introduced in the regenerable soybean plant cell by a recombinant DNA construct comprising the polynucleotide operably linked to a regulatory element, optionally wherein the regulatory element is a heterologous plant promoter.

In certain embodiments, the method comprises providing a guide RNA, at least one polynucleotide modification template, and at least one Cas endonuclease to a soybean plant cell, wherein the at least one Cas endonuclease introduces a double strand break at a locus in the soybean plant cell, and wherein the polynucleotide modification template introduces and/or inserts a polynucleotide encoding a polypeptide comprising an amino acid sequence that is at least 80% identical to any one of SEQ ID NOs: 2, 4, 7 or 10, obtaining a soybean plant from the soybean plant cell, and generating a progeny plant that comprises the polynucleotide and has increased resistance to *Phytophthora* as compared to a control pant not comprising the targeted genetic modification. In certain embodiments, the locus in the soybean plant cell is an endogenous Rps gene or locus. In certain embodiments, the Cas endonuclease is Cas9.

In certain embodiments of the methods described herein, the regenerable plant cell is derived from a soybean plant that is susceptible to at least on race of *Phytophthora*.

In certain embodiments of the methods described herein, the targeted genetic modification is introduced using a genome modification technique selected from the group consisting of polynucleotide-guided endonuclease, CRISPR-Cas endonucleases, based editing deaminases, a zinc finger nuclease, a transcription activator-like effector nuclease (TALEN), engineered site-specific meganucleases, or Argonaute.

Various methods can be used to introduce a genetic modification at a genomic locus that encodes a Rps polypeptide into the plant, plant part, plant cell, seed, and/or grain. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In certain embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

In one embodiment the DSB-inducing agent is sequence specific endonuclease. The endonuclease can be provided to a cell by any method known in the art, for example, but not limited to, transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

TAL effector nucleases (TALEN) are a class of sequence-specific nucleases that can be used to make double-strand breaks at specific target sequences in the genome of a plant or other organism (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type Hs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognized a sequence of 9 contiguous nucleotides, with a dimerization requirement of the nuclease, two sets of zinc finger triplets are used to bind an 18-nucleotide recognition sequence.

Genome editing using DSB-inducing agents, such as Cas9-gRNA complexes, has been described, for example in U.S. Patent Application US 2015-0082478 A1, WO2015/026886 A1, WO2016007347, and WO201625131 all of which are incorporated by reference herein.

In certain embodiments the genetic modification is introduced without introducing a double strand break using base editing technology, see e.g., Gaudelli et al., (2017) Programmable base editing of A*T to G*C in genomic DNA without DNA cleavage. Nature 551(7681):464-471; Komor et al., (2016) Programmable editing of a target base in genomic DNA without double-stranded DNA cleavage, Nature 533 (7603):420-4.

In certain embodiments, base editing comprises (i) a catalytically impaired CRISPR-Cas9 mutant that is mutated such that one of their nuclease domains cannot make DSBs; (ii) a single-strand-specific cytidine/adenine deaminase that converts C to U or A to G within an appropriate nucleotide window in the single-stranded DNA bubble created by Cas9; (iii) a uracil glycosylase inhibitor (UGI) that impedes uracil excision and downstream processes that decrease base editing efficiency and product purity; or (iv) nickase activity to cleave the non-edited DNA strand, followed by cellular DNA repair processes to replace the G-containing DNA strand.

In certain embodiments, the targeted genetic modification is selected from the group consisting of an insertion, deletion, single nucleotide polymorphism (SNP), and a polynucleotide modification. In certain embodiments, the targeted genetic modification is present in (a) the coding region; (b) a non-coding region; (c) a regulatory sequence; (d) an untranslated region; or (e) any combination of (a)-(d) of the genomic locus that encodes the RPS polypeptide.

In certain embodiments the DNA modification increasing the level and or activity of the RPS polypeptide is an insertion of one or more nucleotides, preferably contiguous, in the genomic locus. For example, the insertion of an expression modulating element (EME), such as an EME described in PCT/US2018/025446 (WO2018183878), in operable linkage with the RPS gene. In certain embodiments, the targeted DNA modification may be the replacement of the endogenous RPS promoter with another promoter known in the art to have higher expression. In certain embodiments, the targeted DNA modification may be the insertion of a promoter known in the art to have higher expression into the 5'UTR so that expression of the endogenous RPS polypeptide is controlled by the inserted promoter. In certain embodiments, the DNA modification is a modification to optimize Kozak context to increase expression. In certain embodiments, the DNA modification is a polynucleotide modification or SNP at a site that regulates the stability of the expressed protein.

In certain embodiments, the method comprises expressing in a regenerable soybean plant cell any of the recombinant DNA constructs described herein and generating the plant wherein the plant has increased expression of the polynucleotide and increased resistance to *Phytophthora* infection as compared to a control plant not comprising the recombinant DNA construct.

Various methods can be used to introduce the RPS sequences (e.g., modified RPS sequence or recombinant DNA comprising the modified RPS sequence) into a plant, plant part, plant cell, seed, and/or grain. "Introducing" is intended to mean presenting to the plant, plant cell, seed, and/or grain the inventive polynucleotide or resulting polypeptide in such a manner that the sequence gains access to the interior of a cell of the plant. The methods of the disclosure do not depend on a particular method for introducing a sequence into a plant, plant cell, seed, and/or grain, only that the polynucleotide or polypeptide gains access to the interior of at least one cell of the plant.

"Stable transformation" is intended to mean that the polynucleotide introduced into a plant integrates into the genome of the plant of interest and is capable of being inherited by the progeny thereof. "Transient transformation" is intended to mean that a polynucleotide is introduced into the plant of interest and does not integrate into the genome of the plant or organism or a polypeptide is introduced into a plant or organism.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (U.S. Pat. Nos. 5,563, 055 and 5,981,840), Ochrobacterium-mediated transformation (U.S. Patent Application Publication 2018/0216123 and WO20/092494) direct gene transfer (Paszkowski et al. (1984) EMBO J. 3:2717-2722), and ballistic particle acceleration (see, for example, U.S. Pat. Nos. 4,945,050; 5,879, 918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the RPS sequences can be provided to a plant using a variety of transient transformation methods. Such transient transformation methods include, but are not limited to, the introduction of the RPS protein directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference.

In other embodiments, the inventive polynucleotides disclosed herein may be introduced into plants by contacting plants with a virus or viral nucleic acids. Generally, such methods involve incorporating a nucleotide construct of the disclosure within a DNA or RNA molecule. It is recognized that the inventive polynucleotide sequence may be initially synthesized as part of a viral polyprotein, which later may be processed by proteolysis in vivo or in vitro to produce the desired recombinant protein. Further, it is recognized that promoters disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide disclosed herein can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided, and the transfer cassette is integrated at the target site. The polynucleotide of interest is thereby integrated at a specific chromosomal position in the plant genome. Other methods to target polynucleotides are set forth in WO 2009/114321 (herein incorporated by reference), which describes "custom" meganucleases produced to modify plant genomes, in particular the genome of maize. See, also, Gao et al. (2010) *Plant Journal* 1:176-187.

One of skill will recognize that after the expression cassette containing the inventive polynucleotide is stably incorporated in transgenic plants and confirmed to be operable, it can be introduced into other plants by sexual crossing. Any of a number of standard breeding techniques can be used, depending upon the species to be crossed.

Parts obtained from the regenerated plants described herein, such as flowers, seeds, leaves, branches, fruit, and the like are included, provided that these parts comprise cells comprising the inventive polynucleotide. Progeny and variants, and mutants of the regenerated plants are also included, provided that these parts comprise the introduced nucleic acid sequences.

In one embodiment, a homozygous transgenic plant can be obtained by sexually mating (selfing) a heterozygous transgenic plant that contains a single added heterologous nucleic acid, germinating some of the seed produced and analyzing the resulting plants produced for altered cell division relative to a control plant (i.e., native, non-transgenic). Back-crossing to a parental plant and out-crossing with a non-transgenic plant are also contemplated.

B. Breeding Method for Increasing *Phytophthora* Resistance

Further provided are methods of producing plants having increased *Phytophthora* resistance comprising crossing a plant comprising a targeted genetic modification increasing expression of a polynucleotide encoding a polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 2, 4, 7 or as compared to a control plant not comprising the targeted genetic modification with a second plant line and harvesting the seed produced thereby. In certain embodiments, the seed produced thereby comprises the polynucleotide. In certain embodiments, the second plant is susceptible to *Phytophthora* and the harvested seed produces a plant that is resistant and/or has increased resistance to *Phytophthora*.

In certain embodiments, the method further comprises growing the seed to produce a second-generation progeny plant that comprises the polypeptide and backcrossing the second-generation progeny plant to the second plant to produce a backcross progeny plant that comprises the polypeptide and produces backcrossed seed with increased *Phytophthora* resistance.

Also provided are methods of producing plants having increased *Phytophthora* resistance comprising crossing a plant comprising increased expression of a polynucleotide encoding a polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 2, 4, 7 or 10 as compared to a control plant not comprising the polynucleotide with a second plant line and harvesting the seed produced thereby. In certain embodiments, the plant comprises a recombinant DNA construct described herein. In certain embodiments, the seed produced thereby comprises the polynucleotide. In certain embodiments, the second plant is susceptible to *Phytophthora* and the harvested seed produces a plant that is resistant and/or has increased resistance to *Phytophthora*.

In certain embodiments, the method further comprises growing the seed to produce a second-generation progeny plant that comprises the polypeptide and backcrossing the second-generation progeny plant to the second plant to produce a backcross progeny plant that comprises the polypeptide and produces backcrossed seed with increased *Phytophthora* resistance.

C. Methods to Detect a *Phytophthora* Resistant Plant

Also provided herein are methods for detecting a *Phytophthora* resistant plant comprising identifying plants comprising a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2, 4, 7 or 10. In certain embodiments, the method comprises detecting the nucleic acid sequence using primers and probes that selectively detect a polynucleotide comprising a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2, 4, 7 or 10.

Also provided herein are methods for detecting a *Phytophthora* resistant plant comprising detecting a molecular marker linked to or associated with Rps11, Rps2b, Rps15, or Rps14.

In certain embodiments, the method comprises detecting a marker linked to or associated with Rps11. In certain embodiments, the method comprises detecting in germplasm of a soybean plant at least one allele of a marker locus within a chromosomal interval comprising and flanked by SSR-07-286 (SEQ ID NOs: 66 and 67) and SSR-07-320 (SEQ ID NOs: 84 and 85). In certain embodiments, the method comprises detecting in germplasm of a soybean plant at least one allele of a marker locus within a chromosomal interval comprising and flanked by maker_176 kb (SEQ ID NOs: 76 and 77) and InDel_327 kb (SEQ ID NOs: 78 and 79). In certain embodiments, the method comprises detecting a marker selected from the group consisting of SSR-07-286, SSR-07-295 (SEQ ID NOs: 68 and 69), InDel-626 (SEQ ID NOs: 70 and 71), InDel-SUTR-43 (SEQ ID NOs: 72 and 73), SSR-07-300 (SEQ ID NOs: 74 and 75), 176 kb (SEQ ID NOs: 76 and 77), InDel-327 kb (SEQ ID NOs: 78 and 79), InDel-5.922 (SEQ ID NOs: 80 and 81), InDel-6.036 (SEQ ID NOs: 82 and 83), and SSR-07-320 (SEQ ID NOs: 84 and 85).

In certain embodiments, the method comprises detecting a marker linked to or associated with Rps2b. In certain embodiments, the method comprises detecting in germplasm of a soybean plant at least one allele of a marker locus within a chromosomal interval comprising and flanked by Satt431 (SEQ ID NOs: 20 and 21) and BARCSOY_16_1322 (SEQ ID NOs: 34 and 35). In certain embodiments, the method comprises detecting in germplasm of a soybean plant at least one allele of a marker locus within a chromosomal interval comprising and flanked by BARCSOY_16_1277 (SEQ ID NOs: 22 and 23) and BARCSOY_16_1322 (SEQ ID NOs: 34 and 35). In certain embodiments, the method comprises detecting in germplasm of a soybean plant at least one allele of a marker locus within a chromosomal interval comprising and flanked by BARCSOY_16_1288 (SEQ ID NOs: 26 and 27) and BARCSOY_16_1312 (SEQ ID NOs: 32 and 33). In certain embodiments, the method comprises detecting a marker selected from the group consisting of Satt431, BARCSOY_16_1277, BARCSOY_16_1281 (SEQ ID NOs: 24 and 25), BARCSOY_16_1288, BARCSOY_16_1294 (SEQ ID NOs: 28 and 29), BARCSOY_16_1297 (SEQ ID NOs: 30 and 31), BARCSOY_16_1312, BARCSOY_16_1322, a G at Gm16_36635129 (SEQ ID NO: 37), an A at Gm16_36641187 (SEQ ID NO: 39), a C at Gm16_36687038 (SEQ ID NO: 41), an A at Gm16_36742320 (SEQ ID NO: 43), a C at Gm16_36745870 (SEQ ID NO: 45), a T at Gm16_36789567 (SEQ ID NO: 47), a G at Gm16_36805209 (SEQ ID NO: 49), an A at Gm16_36818299 (SEQ ID NO: 51), a Tat Gm16_36825046 (SEQ ID NO: 53), a G at Gm16_36840817 (SEQ ID NO: 55), a T at Gm16_36844181 (SEQ ID NO: 57), an A at Gm16_36849203 (SEQ ID NO: 59), a T at Gm16_36854790 (SEQ ID NO: 61), a C at Gm16_36870179 (SEQ ID NO: 63), and a G at Gm16_36889339 (SEQ ID NO: 65).

In certain embodiments, the method comprises detecting a marker linked to or associated with Rps15. In certain embodiments, the method comprises detecting in germplasm of a soybean plant at least one allele of a marker locus within a chromosomal interval comprising and flanked by InDel3155 and InDel3701. In certain embodiments, the method comprises detecting in germplasm of a soybean plant at least one allele of a marker locus within a chromosomal interval comprising and flanked by InDel3437 and InDel3701. In certain embodiments, the method comprises detecting in germplasm of a soybean plant at least one allele of a marker locus within a chromosomal interval comprising and flanked by Satt431 and InDel3668. In certain embodiments, the method comprises detecting a marker selected from the group consisting of InDel3155, InDel3255, InDel3304, InDel3437, InDel3575, InDel3586, Satt431, InDel3668, InDel3678, InDel3701, a T at Gm_30813568, a C at Gm16_31787658, a Tat Gm16_31837545, an A at Gm16_31899513, a C at Gm16_32017661, a C at Gm16_32200441, an A at Gm16_32340079, a C at Gm16_32665742, a G at Gm16_32876100, a C at Gm16_33210540, a C at Gm16_33360539, a G at Gm16_33457667, a G at Gm16_34645180, a G at Gm16_35148803, a T at Gm16_35218386, a T at Gm16_35643452, a T at Gm16_35700223, a G at Gm16_35738081, an A at Gm16_36013043, a C at Gm16_36217195, a C at Gm16_36732450, an A at Gm16_36983033, a G at Gm16_37078478, and a G at Gm16_37209075. In certain embodiments, the marker is detected by a primer comprising a nucleotide sequence of any one of SEQ ID NOs: 20-21 and 86-103. In certain embodiments, the marker is detected by a primer pair comprising a nucleotide sequences of SEQ ID NOs: 20 and 21, SEQ ID NOs: 86 and 87, SEQ ID NOs: 88 and 89, SEQ ID NOs: 90 and 91, SEQ ID NOs: 92 and 93, SEQ ID NOs: 94 and 95, SEQ ID NOs: 96 and 97, SEQ ID NOs: 98 and 99, SEQ ID NOs: 100 and 101, and SEQ ID NOs: 102 and 103.

In certain embodiments, the method comprises detecting a marker linked to or associated with Rps14. In certain embodiments, the method comprises detecting in germplasm of a soybean plant at least one allele of a marker locus within a chromosomal interval comprising and flanked by Satt631 and BARCSOY_03_0266. In certain embodiments, the method comprises detecting in germplasm of a soybean plant at least one allele of a marker locus within a chromosomal interval comprising and flanked by BARCSOY_03_0226 and BARCSOY_03_0266. In certain embodiments, the method comprises detecting a marker selected from the group consisting of Satt631, BARCSOY_03_0209, BARCSOY_03_0219, BARCSOY_03_0226, BARCSOYSSR_03_229, BARCSOY_03_0266, InDel3971, InDel4033, InDel4263, InDel4330, a T at Gm03_829023, an A at Gm03_1671384, a G at Gm03_1718435, an A at Gm03_3087237, a G at Gm03_3907697, a C at Gm03_4487138, an A at Gm03_4509101, a C at Gm03_4665923, a C at Gm03_4782127, an A at Gm03_5165511, and a C at Gm03_5217414. In certain embodiments, the marker is detected by a primer comprising a nucleotide sequence of any one of SEQ ID NOs: 104-123. In certain embodiments, the marker is detected by a primer pair comprising a nucleotide sequences of SEQ ID NOs: 104 and 105, SEQ ID NOs: 106 and 107, SEQ ID NOs: 108 and 109, SEQ ID NOs: 110 and 111, SEQ ID NOs: 112 and 113, SEQ ID NOs: 114 and 115, SEQ ID NOs: 116 and 117, SEQ ID NOs: 118 and 119, SEQ ID NOs: 120 and 121, and SEQ ID NOs: 122 and 123.

In certain embodiments, the method further comprises crossing the *Phytophthora* resistant plant detected by the methods described herein with a second plant to produce progeny seed. In certain embodiments, the second plant is susceptible to *Phytophthora*. In certain embodiments, the second plant lacks the Rps11, Rps2b, Rps15, or Rps14 gene.

In certain embodiments, the progeny seed comprises the nucleotide sequence detected using the primers and probes. In certain embodiments, the progeny seed comprises the molecular marker linked to or associated with Rps11, Rps2b, Rps15, or Rps14. In certain embodiments, the progeny seed comprises the at least one allele of a marker locus associated with Rps2b within a chromosomal interval comprising and flanked by BARCSOY_16_1288 and BARCSOY_16_1312. In certain embodiments, the progeny seed and plant produced thereby comprises the at least one allele of a marker locus associated with Rps15 within a chromosomal interval comprising and flanked by Satt431 and InDel3668. In certain embodiments, the progeny seed comprises the at least one allele of a marker locus associated with Rps14 within a chromosomal interval comprising and flanked by BARCSOY_03_0226 and BARCSOY_03_0266. In certain embodiments, the progeny seed and plant produced thereby comprises the Rps11, Rps2b, Rps15, or Rps14 gene.

Any suitable detection method known in the art can be used to detect the polynucleotide. In some examples, the presence of the polynucleotide is directly detected in unamplified genomic DNA by performing a Southern blot on a sample of genomic DNA using probes to the marker loci. In other examples, amplification-based techniques are employed. PCR, RT-PCR, and LCR are in particularly broad use as amplification and amplification-detection methods for amplifying nucleic acids of interest, thus facilitating detection of the polynucleotide. Procedures for performing Southern blotting, amplification (PCR, LCR, or the like), and many other nucleic acid detection methods are well established and are taught, e.g., in Sambrook et al., *Molecular Cloning—A Laboratory Manual* (3d ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., *Current Protocols, a joint venture between* Greene Publishing Associates, Inc. and John Wiley & Sons, Inc., (supplemented through 2002) ("Ausubel")) and *PCR Protocols A Guide to Methods and Applications* (Innis et al. eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

"Primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are oligonucleotides from 10 to 30 nucleic acids in length, but longer or shorter sequences can be employed. Primers may be provided in double-stranded form, though the single-stranded form is preferred. A primer can further contain a detectable label, for example a 5' end label.

"Probe" refers to an oligonucleotide (synthetic or occurring naturally) that is complementary (though not necessarily fully complementary) to a polynucleotide of interest and forms a duplexed structure by hybridization with at least one strand of the polynucleotide of interest. Typically, probes are oligonucleotides from 10 to 50 nucleic acids in length, but longer or shorter sequences can be employed. A probe can further contain a detectable label. The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin, or haptens), and the like. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

Chromosomal interval" designates a contiguous linear span of genomic DNA that resides in planta on a single chromosome. The genetic elements or genes located on a single chromosomal interval are physically linked. The size of a chromosomal interval is not particularly limited. In certain embodiments, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

The term "introgression" or "introgressing" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a quantitative trait loci (QTL), a transgene, or the like. In any case, offspring comprising the desired allele can be repeatedly backcrossed to a line having a desired genetic background and selected for the desired allele, to result in the allele becoming fixed in a selected genetic background. For example, the chromosome 3, 7, or 16 locus described herein may be introgressed into a recurrent parent that is susceptible to *Phytophthora*. The recurrent parent line with the introgressed gene or locus then has increased resistance to *Phytophthora*.

As used herein, the term "linkage" or "linked" is used to describe the degree with which one marker locus is associated with another marker locus or some other locus (for example, a *Phytophthora* locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM). In certain embodiments, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10 (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

"Locus" and "marker locus" are used interchangeably herein and mean a position on a chromosome where a gene and/or marker is located.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of soybean molecular markers are known in the art, and are published or available from various sources, such as the SoyBase internet resource.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus.

A "marker locus" is a specific chromosome location in the genome of a species when a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or a molecule that can be used to identify the presence of a marker locus, e.g., a nucleic acid probe that is complementary to a marker locus sequence. Alternatively, in certain embodiments, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a via a plant without the insertion. Thus, the marker need only indicate whether the indel region is present or absent. Any suitable marker detection technology may be used to identify such a hybridization marker, e.g., SNP technology is used in the examples provided herein.

The following are examples of specific embodiments of some aspects of the invention. The examples are offered for illustrative purposes only and are not intended to limit the scope of the invention in any way.

In accordance with embodiment 1, a soybean plant or soybean seed is provided comprising a targeted genetic modification increasing expression of a polynucleotide encoding a polypeptide comprising an amino acid sequence having at least 80% sequence identity to any one of SEQ ID NOs: 2 or 4 as compared to a control plant not comprising the targeted genetic modification.

In accordance with embodiment 2 the soybean plant or soybean seed of embodiment 1 is provided, wherein the soybean plant or a plant grown from the soybean seed comprising the targeted genetic modification has improved resistance to *Phytophthora* infection as compared to the control plant.

In accordance with embodiment 3 the soybean plant or soybean seed of embodiment 1 or 2 is provided, wherein the soybean plant or a plant grown from the soybean seed comprising the targeted genetic modification has improved resistance at least one race of *Phytophthora* selected from the group consisting of Race1, Race 2, Race3, Race4, Race5, Race6, Race7, Race8, Race9 Race13, Race17, Race25, Race31 as compared to the control plant.

In accordance with embodiment 4 the soybean plant or soybean seed of any one of embodiments 1-3 is provided, wherein the targeted genetic modification introduces a polynucleotide sequence having at least 80% sequence identity to any one of SEQ ID NOs: 1 or 3.

In accordance with embodiment 5 a plant produced by the soybean seed of any one of embodiments 1-4 is provided.

In accordance with embodiment 6 a method of plant breeding is provided comprising crossing the soybean plant of any one of embodiments 1-5 with a second soybean plant to produce a progeny seed.

In accordance with embodiment 7 the method of any one of embodiments 1-6 is provided, wherein the progeny seed comprises the targeted genetic modification and a plant produced from the seed has increased resistance to at least one race of *Phytophthora*.

In accordance with embodiment 8 the method of any one of embodiments 1-7 is provided, wherein the second soybean plant is susceptible to the at least one race of *Phytophthora*.

In accordance with embodiment 9 the method of any one of embodiments 1-9 is provided, wherein the plant, seed or plant produced from the seed has increased resistance to at least one race of *Phytophthora* selected from Race1, Race 2, Race3, Race4, Race5, Race6, Race7, Race8, Race9 Race13, Race17, Race25, or Race31.

In accordance with embodiment 10 a method for generating a *Phytophthora* resistant soybean plant is provided, the method comprising:

(a) introducing in a regenerable soybean plant cell a polynucleotide encoding a polypeptide comprising an amino acid sequence having at least 80% sequence identity to any one of SEQ ID NOs: 2 or 4, and (b) generating the plant wherein the plant expresses the polynucleotide and has increased resistance to *Phytophthora* as compared to a control plant not expressing the polynucleotide.

In accordance with embodiment 11 the method of embodiment 10 is provided, wherein the regenerable plant cell is isolated from a soybean plant susceptible to at least one race of *Phytophthora* and the plant generated has increased resistance to the at least one race of *Phytophthora*.

In accordance with embodiment 12 the method of embodiment 10 or 11 is provided, wherein the at least one race of *Phytophthora* is at least one of Race1, Race 2, Race3, Race4, Race5, Race6, Race7, Race8, Race9 Race13, Race17, Race25, Race31.

In accordance with embodiment 13 the method of any one of embodiments 10-12 is provided, wherein the polynucleotide is introduced in the regenerable soybean plant cell using a targeted genetic modification.

In accordance with embodiment 14 the method of embodiment 13 is provided, wherein the targeted genetic modification is introduced using a genome modification technique selected from the group consisting of polynucleotide-guided endonuclease, CRISPR-Cas endonucleases, based editing deaminases, a zinc finger nuclease, a transcription activator-like effector nuclease (TALEN), engineered site-specific meganucleases, or Argonaute.

In accordance with embodiment 15 the method of any one of embodiments 10-14 is provided, wherein the polynucleotide is introduced in the regenerable soybean plant cell by a recombinant DNA construct comprising the polynucleotide operably linked to at least one regulatory element.

In accordance with embodiment 16 the method of any one of embodiments 10-15 is provided, wherein the at least one regulatory element is a promoter.

In accordance with embodiment 17 the method of embodiment 17 is provided, wherein the promoter is a heterologous promoter.

In accordance with embodiment 18 a method for increasing resistance to *Phytophthora* infection in a soybean plant, the method comprising:

(a) introducing in a regenerable soybean plant cell a targeted genetic modification increasing the expression of a polynucleotide encoding a polypeptide comprising an amino acid sequence having at least 80% sequence identity to any one of SEQ ID NOs: 2 or 4, and (b) generating the plant wherein the plant has increased expression of the polynucleotide and increased resistance to *Phytophthora* infection as compared to a control plant not comprising the targeted genetic modification.

In accordance with embodiment 19 the method of embodiment 18 is provided, wherein the targeted genetic modification is introduced using a genome modification technique selected from the group consisting of polynucleotide-guided endonuclease, CRISPR-Cas endonucleases, based editing deaminases, a zinc finger nuclease, a transcription activator-like effector nuclease (TALEN), engineered site-specific meganucleases, or Argonaute.

In accordance with embodiment 20 the method of embodiment 18 or 19 is provided, wherein the method comprises:

(a) providing a guide RNA, at least one polynucleotide modification template, and at least one Cas endonuclease to a soybean plant cell, wherein the at least one Cas endonuclease introduces a double strand break at a locus in the soybean plant cell, and wherein the polynucleotide modification template inserts a polynucleotide encoding a polypeptide comprising an amino acid sequence that is at least 80% identical to any one of SEQ ID NOs: 2 or 4;

(b) obtaining a soybean plant from the soybean plant cell; and (c) generating a progeny plant that comprises the polynucleotide and has increased resistance to *Phytophthora* as compared to a control pant not comprising the targeted genetic modification.

In accordance with embodiment 21 the method of any one of embodiments 18-20 is provided, wherein the locus is an endogenous Rps locus.

In accordance with embodiment 22 the method of any one of embodiments 18-21, wherein the Cas endonuclease is Cas9.

In accordance with embodiment 23 the method of any one of embodiments 18-22 is provided, wherein the plant cell is isolated from a soybean plant susceptible to at least one race of *Phytophthora* and the progeny plant has increased resistance to the at least one race of *Phytophthora*.

In accordance with embodiment 24 the method of embodiment 23 is provided, wherein the at least one race of *Phytophthora* is at least one of Race1, Race 2, Race3, Race4, Race5, Race6, Race7, Race8, Race9 Race13, Race17, Race25, Race31.

In accordance with embodiment 25 a method for producing a soybean plant with increased resistance to *Phytophthora*, the method comprising:

(a) expressing in a regenerable plant cell a polynucleotide encoding a polypeptide comprising an amino acid sequence having at least 80% sequence identity to any one of SEQ ID NOs: 2 or 4, and (b) generating a plant wherein the plant expresses the polynucleotide and has increased resistance to *Phytophthora* infection as compared to a control plant.

In accordance with embodiment 26 the method of embodiment 25 is provided, wherein the method comprises:

(a) providing a guide RNA, at least one polynucleotide modification template, and at least one Cas endonuclease to a soybean plant cell, wherein the at least one Cas endonuclease introduces a double strand break in the genome of the soybean plant cell, and wherein the polynucleotide modification template inserts a polynucleotide encoding a polypeptide comprising an amino acid sequence that is at least 80% identical to any one of SEQ ID NOs: 2 or 4;

(b) obtaining a soybean plant from the soybean plant cell; and (c) generating a progeny plant that comprises the polynucleotide and has increased resistance to *Phytophthora* as compared to a control pant not comprising the targeted genetic modification.

In accordance with embodiment 27 the method of embodiment 18-26 is provided, wherein the double strand break is introduced at an endogenous Rps gene in the soybean plant cell.

In accordance with embodiment 28 the method of any one of embodiments 18-27 is provided, wherein the Cas endonuclease is Cas9.

In accordance with embodiment 29 the method of any one of embodiments 18-28 is provided, wherein the plant cell is isolated from a soybean plant susceptible to at least one race of *Phytophthora* and the progeny plant has increased resistance to the at least one race of *Phytophthora*.

In accordance with embodiment 30 the method of embodiment 29 is provided, wherein the at least one race of *Phytophthora* is at least one of Race1, Race 2, Race3, Race4, Race5, Race6, Race7, Race8, Race9 Race13, Race17, Race25, Race31.

In accordance with embodiment 31 a soybean plant or soybean seed comprising a recombinant DNA construct comprising a polynucleotide encoding a polypeptide comprising an amino acid sequence that is at least 80% identical to any one of SEQ ID NOs: 2 or 4, wherein the soybean seed or soybean plant has increased expression of the polynucleotide as compared to a control plant not comprising the polynucleotide.

In accordance with embodiment 32 the soybean plant or soybean seed of embodiment 31 is provided, wherein the polynucleotide is operably linked to the endogenous promoter.

In accordance with embodiment 33 the soybean plant or soybean seed of embodiment 31 or 32 is provided, wherein the soybean plant or a plant grown from the soybean seed comprising the recombinant DNA construct has improved *Phytophthora* resistance as compared to the control plant.

In accordance with embodiment 34 a plant produced by the soybean seed of any one of embodiments 31-33 is provided.

In accordance with embodiment 35 a method of plant breeding is provided comprising crossing the soybean plant of any one of embodiments 31-34 with a second soybean plant to produce a progeny seed.

In accordance with embodiment 36 the method of embodiment 35 is provided, wherein the second soybean plant is susceptible to at least one race of *Phytophthora* and a plant produced from the progeny seed is resistant or has increased resistance to the at least one race of *Phytophthora*.

In accordance with embodiment 37 a method for increasing resistance to *Phytophthora* infection in a soybean plant, the method comprising:

(a) expressing in a regenerable soybean plant cell a recombinant DNA construct comprising a polynucleotide encoding a polypeptide comprising an amino acid sequence having at least 80% sequence identity to any one of SEQ ID NOs: 2 or 4, and (b) generating the plant wherein the plant has increased expression of the polynucleotide and increased resistance to *Phytophthora* infection as compared to a control plant not comprising the recombinant DNA construct.

In accordance with embodiment 38 the method of embodiment 37 is provided, wherein the polynucleotide is operably linked to the endogenous promoter.

In accordance with embodiment 39 a method for identifying a soybean plant that displays increased resistance to *Phytophthora* is provided, the method comprising detecting in a soybean plant or seed thereof a polynucleotide sequence encoding a polypeptide comprising an amino acid sequence that is at least 80% identical to any one of SEQ ID NOs: 2 or 4.

In accordance with embodiment 40 the method of embodiment 39 is provided, wherein the polynucleotide sequence is detected using a primer comprising a nucleotide sequence of any one of SEQ ID NOs: 12-19.

In accordance with embodiment 41 The method of embodiment 39 or 40, further comprising:

a. obtaining a first soybean plant comprising the polynucleotide;

b. crossing the first soybean plant to a second soybean plant;

c. evaluating the progeny for the at least one allele; and d. selecting progeny plants that possess the at least one allele thereby selecting plants with increased *Phytophthora* resistance.

In accordance with embodiment 42 a method for identifying a soybean plant that displays increased resistance to *Phytophthora*, the method comprising detecting in a soybean plant or seed thereof at least one allele of a marker locus associated with Rps11, Rps2b, Rps15, or Rps14.

In accordance with embodiment 43 the method of embodiment 42 is provided, wherein:

e. the marker locus is located within a chromosomal interval comprising and flanked by SSR-07-286 and SSR-07-320;

f. the marker locus is located within a chromosomal interval comprising and flanked by InDel3437 and InDel3701;

g. the marker locus is located within a chromosomal interval comprising and flanked by Satt431 and BARCSOY_16_1322; and h. the marker locus is located within a chromosomal interval comprising and flanked by Satt631 and BARCSOY_03_0266.

In accordance with embodiment 44 the method of embodiment 42 or 43 is provided, further comprising:

i. obtaining a first soybean plant comprising the at least one allele of the marker locus;

j. crossing the first soybean plant to a second soybean plant;

k. evaluating the progeny for the at least one allele; and l. selecting progeny plants that possess the at least one allele thereby selecting plants with increased *Phytophthora* resistance.

Example 1

This example demonstrates the determination of the spectrum of resistance of Rps11 to *Phytophthora sojae*.

To explore the resistance spectrum of Rps11, a sub population derived from the Rps11 donor line (PI 594527) and Williams, including 14 lines with Rps11 and 14 lines without Rps11, were inoculated with 16 isolates of *P. sojae*.

The mapping populations were generated from an initial cross between PI 594527 and Williams. In 2015, 2640 F3 plants derived from heterozygous F2 individuals were screened for the identification of recombinants. In 2016 and 2017, two additional larger populations of 7680 and 6730 F4 plants, respectively, derived from heterozygous F3 individuals, were screened for additional recombinants.

About 30 seedlings from each recombinant were inoculated with various isolates of *Phytophthora sojae* using a protocol previously described (Dorrance et al. 2008; Lin et al. 2013). Recombinants, in which less than 25% of the progenies survived after inoculation, were classified as susceptible; recombinants, with more than 25% progeny survival, were classified as segregation. The evaluation was repeated twice for each recombinant. For the resistance spectrum test, lines in which less than 25% of the progenies survived after inoculation were classified as susceptible, lines in which 25% to 75% of the progenies survived after inoculation were classified as partially resistant, and lines in which more than 75% of the progenies survived after inoculation were classified as completely resistant.

As shown in Table 2 all the lines with Rps11 were resistant to all 15 isolates, while all lines without Rps11 were susceptible to 14 isolates except Race 31, suggesting that Rps11 was resistant to all 15 isolates and another gene in the donor line was specifically resistant to Race 31 (Table 2).

TABLE 2

Resistance Spectrum of Rps11

| Sample | Rps11[a] genotype | Race4[b] | Race7 | Race25 | Race3 | Race31 | OH001 |
|---|---|---|---|---|---|---|---|
| 1 | rps11 | S | S | S | S | S | S |
| 2 | rps11 | S | S | S | S | S | S |
| 3 | rps11 | S | S | S | S | H | S |
| 4 | rps11 | S | S | S | S | R | S |
| 5 | rps11 | S | S | S | S | H | S |
| 6 | rps11 | S | S | S | S | H | S |
| 7 | rps11 | S | S | S | S | S | S |
| 8 | rps11 | S | S | S | S | R | S |
| 9 | rps11 | S | S | S | S | H | S |
| 10 | rps11 | S | S | S | S | H | S |
| 11 | rps11 | S | S | S | S | R | S |
| 12 | rps11 | S | S | S | S | H | S |
| 13 | rps11 | S | S | S | S | S | S |
| 14 | rps11 | S | S | S | S | H | S |
| 15 | RPS11 | R | R | R | R | R | R |
| 16 | RPS11 | R | R | R | R | R | R |
| 17 | RPS11 | R | R | R | R | R | R |
| 18 | RPS11 | R | R | R | R | R | R |
| 19 | RPS11 | R | R | R | R | R | R |
| 20 | RPS11 | R | R | R | R | R | R |
| 21 | RPS11 | R | R | R | R | R | R |
| 22 | RPS11 | R | R | R | R | R | R |
| 23 | RPS11 | R | R | R | R | R | R |
| 24 | RPS11 | R | R | R | R | R | R |
| 25 | RPS11 | R | R | R | R | R | R |
| 26 | RPS11 | R | R | R | R | R | R |
| 27 | RPS11 | R | R | R | R | R | R |
| 28 | RPS11 | R | R | R | R | R | R |

| Sample | OHC2S1 | OH003 | MIN1 2004 Mar. 1 | MIN1 2004 Jan. 1 | MIN1 2002 Jan. 5 | MIN1 2002 May 1 | MIN1 2005 Jul. 2 | MIN1 2002 May 5 |
|---|---|---|---|---|---|---|---|---|
| 1 | S | S | S | S | S | S | S | S |
| 2 | S | S | S | S | S | S | S | S |
| 3 | S | S | S | S | S | S | S | S |
| 4 | S | S | S | S | S | S | S | S |
| 5 | S | S | S | S | S | S | S | S |
| 6 | S | S | S | S | S | S | S | S |
| 7 | S | S | S | S | S | S | S | S |
| 8 | S | S | S | S | S | S | S | S |
| 9 | S | S | S | S | S | S | S | S |
| 10 | S | S | S | S | S | S | S | S |
| 11 | S | S | S | S | S | S | S | S |
| 12 | S | S | S | S | S | S | S | S |
| 13 | S | S | S | S | S | S | S | S |
| 14 | S | S | S | S | S | S | S | S |
| 15 | R | R | R | R | R | R | R | R |
| 16 | R | R | R | R | R | R | R | R |
| 17 | R | R | R | R | R | R | R | R |
| 18 | R | R | R | R | R | R | R | R |
| 19 | R | R | R | R | R | R | R | R |
| 20 | R | R | R | R | R | R | R | R |
| 21 | R | R | R | R | R | R | R | R |
| 22 | R | R | R | R | R | R | R | R |
| 23 | R | R | R | R | R | R | R | R |
| 24 | R | R | R | R | R | R | R | R |
| 25 | R | R | R | R | R | R | R | R |
| 26 | R | R | R | R | R | R | R | R |
| 27 | R | R | R | R | R | R | R | R |
| 28 | R | R | R | R | R | R | R | R |

[a]RPS11 represents homozygous Rps11 genotype, rps11 means homozygous Williams genotype (No Rps11)
[b]S represents susceptible, R represents resistant, H represents heterozygous (segregation)

These results demonstrated that Rps11 has a broad resistance spectrum to *Phytophthora sojae*.

Example 2

This example demonstrates the identification of the Rps11 sequence.

Whole genome sequencing and assembly was performed to obtain an assembly of the Rps11 region in the donor line. The genome was built with 34 kb PacBio reads which assembled into 424 contigs with a contig N50 of 13.8 Mb. These contigs were polished with PacBio and Chromium 10× data. The contigs were scaffolded with 45 BioNano maps with a map N50 of 26.7 Mb into 43 hybrid scaffolds with a scaffold N50 of 26.4 Mb, essentially 1-2 scaffolds per chromosome. Gene annotation identified 510 NBS-LRR genes across the entire genome, and twelve NBS-LRR genes were annotated at the Rps11 region, designated as R1 to R12. However, only five (R1, R4, R6, R9 and R12) out of the twelve NBS-LRR genes at Rps11 region were expressed based on RNA-seq analysis (FIG. 1).

In order to fine map the gene underlying Rps11 locus, 17,050 progenies derived from heterozygous $F_2$ or $F_3$ individuals were screened using flanking markers. In total, 43 recombinants were identified, and seedlings derived from these recombinants were inoculated with Race 1 isolate. The combination of additional markers and phenotypic data mapped Rps11 to a 151 kb genome interval, defined by maker_176 kb and InDel_327 kb, harboring 4 intact NBS-LRR genes (R5, R6, R7 and R8), but only R6 was expressed during inoculation, indicating R6 was the best candidate gene responsible for the resistance of Rps11.

Expression of the NBS-LRR genes was further examined in 9 key recombinants that have different combinations of NBS-LRR genes. These studies determined that recombinants with R1 alone, a combination of R1 and R4, or a combination of R9 and R12 were susceptible, whereas the recombinants carrying R6 were resistant (FIG. 2).

These data indicate that R6, which encodes an NB S-LRR protein composed of 2,463 amino acids, is the gene underlying Rps11 locus.

Example 3

This example demonstrates expression of the Rps11 in plants to increase resistance to *Phytophthora sojae*.

Gene constructs of the Rps11 candidate gene, R6 were made using the coding sequence of R6 (SEQ ID NO: 1) from the Rps11 donor line (PI 594527) for overexpression in soybean plants using the Ochrobactrum-mediated soybean embryonic axis transformation as previously described (US20180216123A1; WO2020/005933A1; WO2020/092494A1). The R6 gene construct was transformed into a proprietary soybean line that did not carry the Rps11 gene. Single copy T0 transgenic events were selected based on the PCR analysis with primers specific to the cloning vector. T1 seed was harvested for phenotypic confirmation and expression of the Rps11 in plants. Since the T1 plants are expected to segregate for the transgene the screening for *Phytophthora sojae* races was used as an initial confirmation of the expression of the Rps11 candidate gene.

About 20 seedlings from three T1 families were inoculated with four isolates of *Phytophthora sojae*. Each of these isolates were previously tested on the soybean line used for the transformation to confirm that this line is not resistant to these isolates. For the resistance test, lines with less than 25% seedling survival after inoculation were classified as susceptible, lines with 25% to 75% seedling survival after inoculation were classified as heterozygous, and lines with more than 75% seedling survival after inoculation were classified as resistant.

As shown in Table 3 all the T1 families for the Rps11 candidate transgene construct were segregating or resistant to all the isolates, while the transformable line (TG) without Rps11 was susceptible and the Rps11 donor line, PI 594527 was resistant to all the isolates, suggesting that the candidate gene R6 confers increased resistance expression in the soybean plants that were otherwise susceptible to the *Phytophthora sojae* isolates and is therefore the Rps11 gene (Table 3).

For final confirmation of the Rps11 transgene expression in plants for resistance to *Phytophthora sojae*, T2 seed was generated by selfing the T1 plants. Homozygous, hemizygous and null T2 plants for the Rps11 candidate transgene were selected based on the PCR analysis. Phenotypic screening of the T2 plants was done using 3 different *Phytophthora sojae* isolates, 25, 31 and 06-03, using same method as was done for the T1 screening. As shown in Table 4, the phenotypic screening results showed significantly higher survival rate in homozygous plants as compared to the null plants with mean percent survival rate after inoculation with *Phytophthora sojae* isolate 31 ranging from 93.5% to 98.8% in homozygous plants and 0% to 11.33% in null plants. Similar level of *Phytophthora* disease resistance response was also observed when inoculated with isolates 31 and 06-03. Dosage effect of the R6 transgene was also observed with hemizygous plants showing intermediate level of resistance as compared to the homozygous and nulls (Table4). These results confirm that the expression of the Rps11 R6 gene provides increased resistance to *Phytophthora sojae*.

TABLE 3

Resistance response of T1 families to *Phytophthora sojae* isolates

| Genotype[a] | R31 | R25 | 06-03 | OH002 |
|---|---|---|---|---|
| T1-Fam1 | NE | NE | H | H |
| T1-Fam2 | H | S[b] | NE | NE |
| T1-Fam3 | R | R | R | H |
| TG | S | S | S | S |
| PI 594527 | R | R | R | R |

[a]T1-Fam represents segregating genotype for Rps11 event; TG- Soybean line used for transformation
[b]Single replication data for 6 plants only
[c] S represents susceptible, R represents resistant, H represents heterozygous (segregation)

TABLE 4

Resistance response in T2 families to *Phytophthora sojae* isolates

| Event | N | Race | Percent Survival Rate | | | p-value |
|---|---|---|---|---|---|---|
| | | | Homozygous | Hemizygous | Null | |
| Event 11 1 | | 31 | 93.5[A] (6) | 69.0[A] (2) | 11.33[B] (3) | 7.872e−06 |
| | | 25 | 93.33[A] | 82.0[A] | 40.33[B] | 5.02e−09 |
| | | 06-03 | 74.83[A] | 61.50[A] | 16.67[B] | 2.29e−04 |
| Event 13 2 | | 31 | 93.71[A] (7) | 56.67[B] (3) | 0.00[C] (3) | 1.395e−09 |
| | | 25 | 97.43[A] | 52.0[A] | 26.67[B] | 1.42e−07 |
| | | 06-03 | 85.0[A] | 25.0[B] | 2.33[B] | 6.73e−09 |
| Event 8 3 | | 31 | 98.8[A] (5) | NA | 8.33[B] (3) | 7.306e−07 |
| | | 25 | 92.2[A] | NA | 15.0[B] | 5.461e−05 |
| | | 06-03 | 84.6[A] | NA | 0.00[B] | 5.657e−06 |

N = total no. of T2 lines screened for each event. No. of lines in each genotypic class denoted in parenthesis for race 31. Same no. of lines in each genotypic class was screened for race 31 and 06-03.

Example 4

This example demonstrates the identification of the Rps2b sequence.

PI 594549 C is a soybean landrace identified as a potential source of novel resistance to *Phytophthora sojae* in soybean according to USDA Germplasm Information Network (GRIN).

To determine the resistance of PI 594549 C to various races of *Phytophthora sojae*, disease evaluation was performed using the standard hypocotyl method for all the inoculation experiments. Briefly, 7-day-old seedlings growing in a greenhouse (~25° C.) were tested by injecting 14-day-old *Phytophthora sojae* culture grown on ½ LBA into the hypocotyl of the seedling. In the first day of inoculation, trays holding injected soybean plants were covered by transparent plastic lids to maintain moisture for infection. Disease would further grow for another 5 to 7 days before scoring phenotypes.

For a single plant, if the plant continued to grow after inoculation, it was recorded as resistant, while susceptible would be counted for a dead brown hypocotyl seedling. For a single family, 12 to 36 seedlings were tested dependent on amounts of harvested seeds. If 75% or more seedlings in a family were resistant, then the family was classified as homozygous resistant (R), or homozygous susceptible (S) when less than 25% seedlings were resistant. The remaining families were counted as heterozygous resistant (Rs).

As shown in Table 5, the hypocotyl inoculation studies determined that PI 594594 C was resistant to all *Phytophthora sojae* isolates tested including race 1, race 3, race 4, race 7, race 13, race 17, race 25, four novel isolates from Minnesota (MIN12001.01.05, MIN12001.03.01, MIN12004.01.01 and MIN12005.07.02) and two novel isolates from Indiana (ISA19A-1, ISA71D-1).

TABLE 5

Responses of Soybean Landrace PI 5945493 to Different *P. sojae* Isolates

| P. sojae isolate | Virulence pathotype | No. of plants examined | No. of plants survived | Phenotype |
|---|---|---|---|---|
| Race 1 | 7 | 12 | 12 | Resistant |
| Race 3 | 1a, 7 | 9 | 10 | Resistant |
| Race 4 | 1a, 1c, 7 | 11 | 10 | Resistant |
| Race 7 | 1a, 2, 3a, 3c, 4, 5, 6, 7 | 10 | 10 | Resistant |
| Race 13 | 4, 6, 7 | 11 | 9 | Resistant |
| Race 17 | 1b, 1d, 2, 3a, 3b, 3c, 4, 5, 6, 7, 8 | 25 | 22 | Resistant |
| Race 25 | 1a, 1b, 1c, 1k, 7 | 10 | 9 | Resistant |
| ISA19A-1 | 1a, 1b, 1k, 4, 6, 7 | 10 | 10 | Resistant |
| ISA71D-1 | 1a, 1c, 1d, 7 | 11 | 10 | Resistant |
| MIN12001.01.05 | NA | 10 | 10 | Resistant |
| MIN12004.01.01 | NA | 10 | 10 | Resistant |
| MIN12004.03.01 | NA | 10 | 10 | Resistant |
| MIN12005.07.02 | NA | 11 | 11 | Resistant |

A single isolate ISA 124C-1 (race 1) was used to characterize the *P. sojae* resistance pattern found in PI 594549 C. By crossing PI 594549 C with the susceptible Williams cultivar, 173 $F_2$ individuals from self-pollination of $F_1$ were generated for a resistance test. For 59 $F_2$ individuals, 50 were resistant and 9 were susceptible, and the null hypothesis that resistance was carried by single dominant locus cannot be rejected ($\chi^2=2.89$, p=0.09) (Table 6). Single locus inheritance pattern was further confirmed by evaluating the 104 $F_{2:3}$ families against *P. sojae* race 1. The segregation of R (homozygous resistant): H (heterozygous resistant): S (homozygous susceptible) observed for resistance to race 1 was 26:48:30, which fits the expected 1:2:1 ratio ($\chi^2=0.92$, p=0.63) (Table 6). In all, these results indicate that the resistance for *P. sojae* race 1 in PI 594549C is carried by a single Rps locus.

TABLE 6

Segregation Ratios of Phenotypes in the Mapping Population

| Parental lines and mapping population | Observed numbers | | | Expected ratio | $\chi^2$ goodness of fit test | |
| | R | Rs | S | | $\chi^2$ | p |
|---|---|---|---|---|---|---|
| PI 594549C | 12 | — | 0 | | | |
| Williams | 0 | — | 12 | | | |
| (PI 594549C × Williams) $F_2$ plants | 50 | — | 9 | 3:1 | 2.89 | 0.09 |
| (PI 594549C × Williams) $F_{2:3}$ families | 26 | 48 | 30 | 1:2:1 | 1.47 | 0.63 |

R—homozygous resistant,
Rs—heterozygous resistant,
S—homozygous susceptible

To detect chromosomal segments linked to the resistance gene for *P. sojae* race 1 in PI 594549C, ten resistant $F_{2:3}$ families and ten susceptible $F_{2:3}$ families were selected for bulked segregant analysis (BSA). Resistant and susceptible bulks were formed by pooling DNA samples of 10 resistant families and 10 susceptible families separately. The pooled samples were genotyped by the SoySNP6K BeadChip comprising 6210 effective SNP markers together with two parental lines. A total of 2,420 SNPs distributed along the 20 chromosomes were polymorphic between both parents. According to the principle of BSA, in the susceptible bulks, the SNP makers closely linked with the rps locus would be homozygous nucleotides that are the same as shown in the susceptible parental line Williams; whereas in the resistant bulk, such SNPs would be heterozygous nucleotides from both parental lines. Meanwhile, there will be no differences between resistant and susceptible bulks by the SNP markers unlinked with the Rps/rps locus and heterozygous nucleotides would be shown in both bulks. After comparison of the genotypes of the two bulks, a roughly 2-Mb region spanning from about 35 Mb to the end of chromosome 16 (FIG. 3) was found. This region also harbors a previously identified Rps2 and RpsUN2, thus the gene was designated as Rps2b (Rps2 Corteva Agriscience).

According to initial mapping using the BSA method, six polymorphic SSR markers Satt431 (SEQ ID NOs: 20 and 21), BARCSOYSSR_16_1277 (SEQ ID NOs: 22 and 23), BARCSOYSSR_12_1281 (SEQ ID NOs: 24 and 25), BARCSOYSSR_12_1288 (SEQ ID NOs: 26 and 27), BARCSOYSSR_16_1312 (SEQ ID NOs: 32 and 33), BARCSOYSSR_16_1322 (SEQ ID NOs: 34 and 35) from a total of 36 SSR markers were selected for the construction of a linkage map. All markers were observed at the expected 1:2:1 segregation ratio (Table 7), and 18, 11, 10, 9, 8 and 12 recombinants between each of these six markers and the Rps2b locus were defined, respectively. Among these 6 markers, Rps2b is more tightly linked with BARCSOYSSR_16_1288 and BARCSOYSSR_16_1312 compared with the rest of the four markers. A linkage map was constructed with these 6 makers and all markers were consistent with their order annotated on the Williams 82 reference genome (FIG. 4). On the map, Rps2b was defined to a 4.3-cM region flanked by BACSOYSSR_16_1288 and BARCSOYSSR_16_1312, and the physical distance between the two markers is about 444.6 kb.

TABLE 7

Chi-Square ($\chi^2$) Goodness of Fit Test for the Markers in the F$_2$ Population Deduced Based on the F$_{2:3}$ Progenies Derived from PI 594549c × Williams

| Marker[a] | Observed number[b] | | | $\chi^2$ goodness of fit test | |
|---|---|---|---|---|---|
| | a | h | b | $\chi^{2\,1:2:1}$ | p |
| Satt431 | 30 | 46 | 28 | 1.50 | 0.48 |
| BARCSOYSSR_16_1288 | 26 | 47 | 31 | 1.44 | 0.49 |
| BARCSOYSSR_16_1294 | 26 | 47 | 31 | 1.44 | 0.49 |
| BARCSOYSSR_16_1297 | 23 | 51 | 30 | 4.39 | 0.11 |
| BARCSOYSSR_16_1312 | 26 | 49 | 28 | 0.98 | 0.61 |
| BARCSOYSSR_16_1322 | 26 | 50 | 28 | 0.23 | 0.89 |

[a]SSR markers were obtained from Song et al. (2010)
[b]a means homozygous for the marker allele from the resistant PI 594549C; b means homozygous for the marker allele from the susceptible Williams; h means heterozygous for the marker alleles from both parents In order to narrow the mapping region of Rps2b, an F$_3$ population consisting of 1212 individuals and an F$_4$ population containing about 12,000 individuals were developed. Polymorphic KASP markers between PI 594549C and the Williams cultivar were developed from the soybean reference genome Wm82.a1 and were used for genotyping recombinants. The whole genome sequence of PI 594549C was sequenced by PacBio single molecule sequencing platform. No contig harbors both BARCSOYSSR_16_1288 and BARCSOYSSR_16_1312 in the sequencing library. A contig (tig14) harboring BARCSOYSSR_16_1288, BARCSOY, BARCSOYSSR_16_1294, BARCSOYSSR_16_1297 and BARCSOYSSR_16_1302 was used as a reference sequence for finer mapping of the Rps2b gene since it includes all R-genes in the mapping region. The KASP markers which can be uniquely mapped to tig14 were kept for accurate genotyping. There are 25 recombinants defined by BARCSOYSSR_16_1288 and BARCSOYSSR_16_1302, including 3 from the F$_3$ population and 22 from heterozygous-susceptible recombinants of the F$_4$ population. Phenotypes of these recombinants were identified from their derived families by hypocotyl inoculation methods. 2 recombinants (664, 7855) defined Rps2b downstream of KASP marker Gm16_36745870, while 7 recombinants (2123, 3600, 5303, 131-4, 10675, 5643, 31-1) defined the Rps2b upstream of KASP maker Gm16_36789567. For the remaining 16 recombinants, 15 of them were consistent with the 9 key recombinants, while the remaining recombinant defined Rps2b downstream of KASP marker Gm16_36789567. The physical distance between Gm16_36745870 and Gm_36789567 is 32.6 kb on tig14 and 7 genes are located is this region including 4 NBS type R-genes. Rps2 was mapped physically downstream of RpsUN2. Using RpsUN2 as a reference, Rps2b is also a different gene compared with Rps2, but likely to be a new locus of RpsUN2.

By genotyping with two flanking markers, BARCSOYSSR_16_1288 and BARCSOYSSR_16_1312, eight homozygous resistance families were tested with eight homozygous susceptible families as control (Table 8). Rps2b had resistance to 11 of 13 P. sojae isolates, and was susceptible to race 7 and race 17. By comparing Rps2 and RpsUN2, which is also mapped to the end of chromosome 16, Rps2b showed broader resistance as Rps2 showed complete resistance to only 7 of the isolates and RpsUN2 showed resistance to only 6 of the isolates. The results further indicate that Rps2b is a novel Rps gene.

TABLE 8

Marker Assisted Resistance Spectrum Analysis of Rps2b to Isolates of P. sojae

| P. sojae | | F$_{2:3}$ families selected[a] | | Parental lines | | Rps genes on Chr16 | |
|---|---|---|---|---|---|---|---|
| Isolate | Race | Rps2b | Rps2b | PI594549C | Williams | Rps2 | RpsUN2 |
| 124C-1 | 1 | R[b] | S | R | S | R | R |
| 94-14-432(2) | 3 | R | S | R | S | R | R |
| 94-13p-197 | 4 | R | S | R | S | R | I |
| 95-11-117 (4) | 7 | S | S | R | S | S | S |
| pmg(13)-1 | 13 | R | S | R | S | S | I |
| pmg(17)-1 | 17 | S | S | R | S | S | S |
| pmg(25)-1 | 25 | R | S | R | S | R | R |
| ISA 19A-1 | N/A | R | S | R | S | I | I |
| ISA 71D-1 | N/A | R | S | R | S | I | I |
| MIN1 2001 Jan. 5 | N/A | R | S | R | S | R | R |
| MIN1 2004 Jan. 1 | N/A | R | S | R | S | I | R |
| MIN1 2004 Mar. 1 | N/A | R | S | R | S | R | R |
| MIN1 2005 Jul. 2 | N/A | R | S | R | S | R | S |

[a]BARCSOYSSR_16_1288 and BARCSOYSSR_16_1312 are two molecular markers used for selections. The resistance pattern of Rps2b against each P. sojae isolate was scored by the proportion of resistance progenies in 8 selected homozygous resistant F$_{2:3}$ families. The reaction of Rpscas was evaluated from 8 homozygous susceptible F$_{2:3}$ families.
[b]A family was recorded as resistant if >75% of seedlings survived after inoculation, susceptible if <25% of seedlings survived, and intermediate resistant if the proportion of resistant seedlings was between 25% and 75%.

The first of the 4 NBS type R-gene in the fine-mapping region on tig14 was completely shared by PI 594549C and Williams with 100% sequence identity, while the remaining 3 R-genes were not found in the mapping region of Williams 82 reference genome. In recombinants whose phenotypes are susceptible, expression of these 3 genes is not detected, while for recombinants whose genotypes are heterozygous resistant, all these three genes are expressed (FIGS. 5A-5C).

The gene-structure of these three NBS type R-genes were further analyzed and of the three genes only R-gene3 is a complete TIR-NBS-LRR type R-gene. For Rgene2, though the length of its transcript is 4410 bp and shares 99% sequence identity with *Glycine soja* TMV resistance gene in newly sequenced wild soybean W05 genome, it has a premature stop codon. As a result, the length of its potential longest open reading frame is only 1926 bp which encodes incomplete 641-amino acid R gene carrying only a TIR-NBS domain. For Rgene4, the length of its longest ORF is 1152 bp and also encodes 383-amino acid R gene with only a TIR-NBS domain.

Taken together these results indicate that Rgene3 is likely to be the candidate gene for Rps2b.

Example 5

This example demonstrates expression of Rps2b in plants to increase resistance to *Phytophthora sojae.*

A gene construct comprising the Rps2b candidate gene (Rgene3) was made using the CDS of Rgene3 from the Rps2b donor line (PI 594549 C). The Rps2b gene construct was transformed into the susceptible Williams soybean line and single copy TO transgenic events were selected based on the PCR analysis with primers specific to the cloning vector. Two independent transgenic lines were obtained for further testing.

T2 plants expressing the Rps2b gene, the soybean line $F_5$ RIL (positive control line), and the native Williams line (negative control) were inoculated with *P. sojae* Race 1 and Race 25. As shown in FIGS. 6A and 6B, transgenic lines expressing the Rps2b gene had similar levels of resistance to Race 1 (FIG. 6A) and Race 25 (FIG. 6B) as compared with the $F_5$ RIL line. The expression level of Rps2b in the T2 transgenic lines were similar to the expression level of Rps2b in the $F_5$ RIL line (FIG. 6C), suggesting that the resistance does not result from autoimmunity triggered by the over-expression of an NB S-LRR gene.

Taken together, these results indicate that Rgene3 is the Rps2b gene.\

Example 6

This example demonstrates the identification of the Rps15 sequence.

PI 594592 carries resistance to *P. sojae* races 1, 3, 7 and 25. Evaluation of *P. sojae* resistance/susceptibility to other *Phytophthora sojae* races was examined using a modified hypocotyl inoculation. 7-day-old soybean seedlings growing in a greenhouse (about 25° C.) were inoculated with mycelial slurry from 14-day-old isolates maintained on ½ LBA media. A small incision was made approximately 1 cm below the cotyledon for insertion of mycelium into the wound. After inoculation, each tray holding seedlings was covered with a transparent plastic lid for one day to create an environment with a high humidity level to promote infection. Before scoring phenotypes, disease growth was maintained for another 5-7 days after removal of the lid. For a single plant, if the seedling kept growing after inoculation, it was recorded as resistant, and if the seedlings died with necrosis in the hypocotyl it was marked as susceptible. 20 to 36 progeny was analyzed for phenotype scoring for each family. A family was classified as homozygous resistant (R) if no less than 75% progenies survived, segregating (Rs) if 25-75% of progenies survived, or heterozygous susceptible (S) if less than 25% of the seedlings were alive.

As shown in Table 9, resistance to *P. sojae* races 1, 3, 7 and 25 was confirmed and it was further determined that PI 594592 carries resistance to *P. sojae* races 4, 13, 17, and two newly found predominant isolates collected from soybean fields in Indiana (ISA19A-1, ISA17D-1) and four isolates collected from soybean fields in Minnesota (MIN12001.01.05, MIN12004.01.01, MIN12004.03.01 and MIN12005.07.02).

TABLE 9

Responses of Soybean Landrace PI 594592 to Different *P. sojae* Isolates

| *P. sojae* isolate | Virulence pathotype | No. of plants examined | No. of plants survived | Phenotype |
|---|---|---|---|---|
| Race 1 | 7 | 10 | 10 | Resistant |
| Race 3 | 1a, 7 | 11 | 11 | Resistant |
| Race 4 | 1a, 1c, 7 | 10 | 10 | Resistant |
| Race 7 | 1a, 2, 3a, 3c, 4, 5, 6, 7 | 12 | 11 | Resistant |
| Race 13 | 4, 6, 7 | 11 | 11 | Resistant |
| Race 17 | 1b, 1d, 2, 3a, 3b, 3c, 4, 5, 6, 7, 8 | 12 | 11 | Resistant |
| Race 25 | 1a, 1b, 1c, 1k, 7 | 10 | 10 | Resistant |
| ISA19A-1 | 1a, 1b, 1k, 4, 6, 7 | 11 | 11 | Resistant |
| ISA71D-1 | 1a, 1c, 1d, 7 | 11 | 11 | Resistant |
| MIN12001.01.05 | NA | 10 | 10 | Resistant |
| MIN12004.01.01 | NA | 10 | 10 | Resistant |
| MIN12004.03.01 | NA | 11 | 11 | Resistant |
| MIN12005.07.02 | NA | 10 | 10 | Resistant |

To determine the inheritance pattern of *P. sojae* resistance in PI 594592, 60 $F_2$ plants derived from a cross between PI 594592 and the Williams cultivar were tested using race 1. Of the 60 plants, 46 were resistant to race 1, while 14 were susceptible. This observation suggests that resistance to *P. sojae* race 1 is carried by a single locus in PI 594592 since the segregation fits a phenotypic ratio of $3:1(\chi^{2=0.09}, p=0.77)$ (Table 10). 200 $F_{2:3}$ families from $F_2$ plants were subsequently developed by self-pollination, and tested for resistance to race 1. Among these 200 families, 47 were homozygous resistant (R), 107 showed heterozygous resistance, and 50 were homozygous susceptible, which fit a phenotypic ratio of $1:2:1$ $((\chi^2=0.09, p=0.77)$. This observation further indicates the resistance to *P. sojae* race1 is conferred by a single locus.

TABLE 10

Segregation Ratios of Phenotypes in the Mapping Population

| | | | | | $\chi^2$ goodness of fit test | |
|---|---|---|---|---|---|---|
| Parental lines and mapping population | Observed numbers | | | Expected | | |
| | R | Rs | S | ratio | $\chi^2$ | p |
| PI 594592 | 12 | — | 0 | | | |
| Williams | 0 | — | 12 | | | |
| (PI 594592 × Williams) $F_2$ plants | 46 | — | 14 | 3:1 | 0.09 | 0.77 |
| (PI 594592 × Williams) $F_{2:3}$ families | 43 | 107 | 50 | 1:2:1 | 1.47 | 0.48 |

R—homozygous resistant,
Rs—heterozygous resistant,
S—homozygous susceptible 10 completely susceptible $F_{2:3}$ families and 10 completely resistant $F_{2:3}$ families were selected to make up susceptible and resistant bulks. The resistant and susceptible bulks, along with the two parental lines Williams and PI 594592, were genotyped with the SoySNP6K Infinium BeadChips consisting of 6000 SNP markers. In total, there are 2509 polymorphic SNPs distributed along all 20 chromosomes between the two parental lines. If there were differences detected between resistant and susceptible bulks, and the SNP markers detected homozygous nucleotides that are same as shown in the resistant parental line PI 594592, then the SNP markers are believed to closely linked to Rps locus. Based on this principle, a ~6.5 Mb genomic region on chromosome 16 showing homozygous SNP sites in resistant bulk and heterozygous SNP sites in susceptible bulk was identified, starting from −30.8 Mb to the end of chromosome16 according to soybean reference genome Wm82.al (Table 11 and FIG. 7).

within the defined ~6.5 Mb Rps15 region and were used for genotyping 200 $F_{2:3}$ families. Each of these markers revealed a 1:2:1 ratio for three possible genotypes (R, Rs, S) in the mapping population (Table 13). Combining all the genotypic and phenotypic data from the $F_{2:3}$ families, a linkage map comprising all the sixteen markers in the Rps15 locus (FIG. 8) was constructed. In the map, Rps15 is flanked by SSR marker Satt431 and InDel marker InDel3618, and the genetic distance to Rps15 were 3.6 and 1.4 cM, respectively. According to the soybean Williams82 reference genome, the 5 cM region corresponds to a roughly 462 kb region harboring 58 different genes (Table 14).

TABLE 11

Genotypic Comparison Between the Resistant and Susceptible Bulks at the SNP Sites Detected Between the Two Parental Lines at the End of Chromosome 16

| SNP ID | Chromo-some | Pos-ition(bp) | Williams | Sus-ceptible Bulk | Re-sistant Bulk | PI 594592 |
|---|---|---|---|---|---|---|
| SNP1912 | Gm16 | 28266706 | TT | TC | TC | CC |
| SNP1913 | Gm16 | 28407237 | AA | AC | AC | CC |
| SNP1914 | Gm16 | 28443553 | TT | TC | TC | CC |
| SNP1915 | Gm16 | 28613278 | CC | TC | TC | TT |
| SNP1916 | Gm16 | 28706800 | AA | AG | AG | GG |
| SNP1917 | Gm16 | 29985920 | AA | AG | AG | GG |
| SNP1918 | Gm16 | 30038668 | GC | TG | TG | TT |
| SNP1919 | Gm16 | 30108889 | CC | AC | AC | AA |
| SNP1920 | Gm16 | 30813568 | GG | TG | TT | TT |
| SNP1921 | Gm16 | 31454423 | GG | AG | AA | AA |
| SNP1922 | Gm16 | 31787658 | TT | TC | CC | CC |
| SNP1923 | Gm16 | 31837545 | CC | TC | TT | TT |
| SNP1924 | Gm16 | 31899513 | GG | AG | AA | AA |
| SNP1925 | Gm16 | 32017661 | AA | AC | CC | CC |
| SNP1926 | Gm16 | 32200441 | AA | AC | CC | CC |
| SNP1927 | Gm16 | 32340079 | GG | AG | AA | AA |
| SNP1928 | Gm16 | 32665742 | TT | TC | CC | CC |
| SNP1929 | Gm16 | 32876100 | AA | AG | GG | GG |
| SNP1930 | Gm16 | 33210540 | TT | TC | CC | CC |
| SNP1931 | Gm16 | 33360539 | TT | TC | CC | CC |
| SNP1932 | Gm16 | 33457667 | TT | TT | GG | GG |
| SNP1933 | Gm16 | 34645180 | AA | AG | GG | GG |
| SNP1934 | Gm16 | 35148803 | TT | TG | GG | GG |
| SNP1935 | Gm16 | 35218386 | GG | TG | TT | TT |
| SNP1936 | Gm16 | 35643452 | CC | TC | TT | TT |
| SNP1937 | Gm16 | 35700223 | GG | TG | TT | TT |
| SNP1938 | Gm16 | 35738081 | AA | AG | GG | GG |
| SNP1939 | Gm16 | 36013043 | AA | AC | AA | CC |
| SNP1940 | Gm16 | 36217195 | TT | TC | CC | CC |
| SNP1941 | Gm16 | 36732450 | TT | TT | CC | CC |
| SNP1942 | Gm16 | 36983033 | CC | CC | AA | AA |
| SNP1943 | Gm16 | 37078478 | AA | AA | GG | GG |
| SNP1944 | Gm16 | 37209075 | TT | TT | GG | GG |

In order to fine map the Rps gene, the re-sequencing data of the two parental lines combined with the reference genome was used in marker design. 10 InDel markers in the defined region were designed and confirmed for polymorphism between the two parental lines. 6 potential SSR markers that are closely linked with two previously identified Rps genes, Rps2 and RpsUN2 were also tested. These markers also showed polymorphism between the two parental lines (Table 12). These 16 markers are evenly distributed

TABLE 12

Polymorphic Insertion/Deletion (InDel) and SSR Markers Identified Between PI594592 and Williams

| SSR Marker | Chr | Forward primer | Reverse primer |
|---|---|---|---|
| InDel3155 | 16 | SEQ ID NO: 86 | SEQ ID NO: 87 |
| InDel3255 | 16 | SEQ ID NO: 88 | SEQ ID NO: 89 |
| InDel3304 | 16 | SEQ ID NO: 90 | SEQ ID NO: 91 |
| InDel3437 | 16 | SEQ ID NO: 92 | SEQ ID NO: 93 |
| InDel3575 | 16 | SEQ ID NO: 94 | SEQ ID NO: 95 |
| InDel3586 | 16 | SEQ ID NO: 96 | SEQ ID NO: 97 |
| InDel3668 | 16 | SEQ ID NO: 98 | SEQ ID NO: 99 |
| InDel3678 | 16 | SEQ ID NO: 100 | SEQ ID NO: 101 |
| InDel3701 | 16 | SEQ ID NO: 102 | SEQ ID NO: 103 |
| Satt431 | 16 | SEQ ID NO: 20 | SEQ ID NO: 21 |
| BARCSOYSSR_16_1288 | 16 | SEQ ID NO: 26 | SEQ ID NO: 27 |
| BARCSOYSSR_16_1294 | 16 | SEQ ID NO: 28 | SEQ ID NO: 29 |
| BARCSOYSSR_16_1297 | 16 | SEQ ID NO: 30 | SEQ ID NO: 31 |
| BARCSOYSSR_16_1312 | 16 | SEQ ID NO: 32 | SEQ ID NO: 33 |
| BARCSOYSSR_16_1322 | 16 | SEQ ID NO: 34 | SEQ ID NO: 35 |

TABLE 13

Chi-Square ($\chi^2$) Goodness of Fit Test for the Markers in the $F_2$ Population Deduced Based on the $F_{2:3}$ Progenies Derived From Pi 594592 × Williams

| Marker | Observed number[a] | | | $\chi^2$ goodness of fit test | |
|---|---|---|---|---|---|
| | a | h | b | $\chi^{2\,1:2:1}$ | p |
| | 43 | 107 | 50 | 1.47 | 0.48 |
| InDel3155 | 48 | 103 | 49 | 0.19 | 0.91 |
| InDel3255 | 50 | 98 | 52 | 0.12 | 0.94 |
| InDel3304 | 47 | 106 | 47 | 0.72 | 0.70 |
| InDel3437 | 48 | 105 | 47 | 0.51 | 0.77 |
| InDel3575 | 44 | 109 | 47 | 1.71 | 0.43 |
| InDel3586 | 44 | 109 | 47 | 1.71 | 0.43 |
| Satt431 | 47 | 104 | 49 | 0.36 | 0.84 |
| InDel3668 | 45 | 106 | 49 | 0.88 | 0.64 |
| InDel3678 | 45 | 109 | 46 | 1.63 | 0.44 |
| InDel3701 | 43 | 110 | 47 | 2.16 | 0.34 |
| BARCSOYSSR_16_1288 | 40 | 113 | 47 | 3.87 | 0.14 |
| BARCSOYSSR_16_1294 | 41 | 113 | 46 | 3.63 | 0.16 |
| BARCSOYSSR_16_1297 | 41 | 112 | 47 | 3.24 | 0.20 |
| BARCSOYSSR_16_1312 | 42 | 112 | 46 | 3.04 | 0.22 |
| BARCSOYSSR_16_1322 | 44 | 110 | 46 | 2.04 | 0.36 |

[a]a means homozygous for the marker allele from the resistant PI 594592; b means homozygous for the marker allele from the susceptible Williams; h means heterozygous for the marker alleles from both parents

TABLE 14

Gene Annotation in the Mapped Region According to the Soybean Reference Genome (Wm82.a2.v1)

| Genes | Annotation |
|---|---|
| Glyma.16g200900 | MEMBER OF 'GDXG' FAMILY OF LIPOLYTIC ENZYMES |
| Glyma.16g201000 | MEMBER OF 'GDXG' FAMILY OF LIPOLYTIC ENZYMES |

TABLE 14-continued

Gene Annotation in the Mapped Region According
to the Soybean Reference Genome (Wm82.a2.v1)

| Genes | Annotation |
|---|---|
| Glyma.16g201100 | Helix-loop-helix DNA-binding domain |
| Glyma.16g201200 | LEUCINE-RICH REPEAT RECEPTOR-LIKE PROTEIN KINASE |
| Glyma.16g201300 | Helix-loop-helix DNA-binding domain |
| Glyma.16g201400 | Helix-loop-helix DNA-binding domain |
| Glyma.16g201500 | LEUCINE-RICH REPEAT RECEPTOR-LIKE PROTEIN KINASE |
| Glyma.16g201600 | EXOSTOSIN (HEPARAN SULFATE GLYCOSYLTRANSFERASE)-RELATED |
| Glyma.16g201700 | PROPROTEIN CONVERTASE SUBTILISIN/KEXIN |
| Glyma.16g201800 | Transferase family |
| Glyma.16g201900 | cysteine-rich RLK (RECEPTOR-like protein kinase) 25 |
| Glyma.16g202000 | Embryo-specific protein 3 |
| Glyma.16g202100 | cysteine-rich RLK (RECEPTOR-like protein kinase) 25 |
| Glyma.16g202200 | LEUCINE-RICH REPEAT RECEPTOR-LIKE PROTEIN KINASE |
| Glyma.16g202300 | HXXXD-type acyl-transferase family protein |
| Glyma.16g202400 | LEUCINE-RICH REPEAT RECEPTOR-LIKE PROTEIN KINASE |
| Glyma.16g202500 | Embryo-specific protein 3 |
| Glyma.16g202600 | F-box family protein |
| Glyma.16g202700 | 40S RIBOSOMAL PROTEIN S14/30S RIBOSOMAL PROTEIN S11 |
| Glyma.16g202800 | F-box family protein |
| Glyma.16g202900 | F-box family protein |
| Glyma.16g203000 | F-box family protein |
| Glyma.16g203100 | Iron-binding zinc finger CDGSH type |
| Glyma.16g203200 | POTASSIUM/PROTON ANTIPORTER-RELATED |
| Glyma.16g203300 | LEUCINE-RICH REPEAT RECEPTOR-LIKE PROTEIN KINASE |
| Glyma.16g203400 | BOX C/D SNORNA PROTEIN 1 |
| Glyma.16g203500 | RING FINGER DOMAIN-CONTAINING |
| Glyma.16g203600 | 1-AMINOCYCLOPROPANE-1-CARBOXYLATE SYNTHASE |
| Glyma.16g203700 | GLUTAMATE DEHYDROGENASE/NADP-SPECIFIC GLUTAMATE DEHYDROGENASE 1-RELATED |
| Glyma.16g203800 | No functional annotations |
| Glyma.16g203900 | DNA REPAIR/RNA PROCESSING CPSF FAMILY/CLEAVAGE AND POLYADENYLATION SPECIFICITY FACTOR SUBUNIT 1 |
| Glyma.16g204000 | ATP-DEPENDENT CLP PROTEASE |
| Glyma.16g204100 | ATP-DEPENDENT CLP PROTEASE |
| Glyma.16g204200 | BED zinc finger/hAT family C-terminal dimerisation region |
| Glyma.16g204300 | PROTEIN REGULATOR OF CYTOKINESIS 1 PRC1-RELATED |
| Glyma.16g204400 | No functional annotations |
| Glyma.16g204500 | integral component of membrane |
| Glyma.16g204600 | Enolase, C-terminal TIM barrel domain/Enolase, N-terminal domain |
| Glyma.16g204700 | nucleic acid binding |
| Glyma.16g204800 | Tetratricopeptide repeat (TPR)-like superfamily protein |
| Glyma.16g204900 | SPFH domain/Band 7 family |
| Glyma.16g205000 | No functional annotation |
| Glyma.16g205100 | LEUCINE-RICH REPEAT RECEPTOR-LIKE PROTEIN KINASE |
| Glyma.16g205200 | CHLOROPHYLL A/B BINDING PROTEIN |
| Glyma.16g205300 | integral component of membrane |
| Glyma.16g205400 | No functional annotation |
| Glyma.16g205500 | APO PROTEIN 1, CHLOROPLASTIC |
| Glyma.16g205600 | No functional annotation |
| Glyma.16g205700 | AAA domain (Cdc48 subfamily)/C-terminal, D2-small domain, of ClpB protein |
| Glyma.16g205800 | No functional annotation |
| Glyma.16g205900 | No functional annotation |
| Glyma.16g206000 | Pentatricopeptide repeat (PPR) superfamily protein |
| Glyma.16g206100 | Trypsin and protease inhibitor |
| Glyma.16g206200 | Hsp20/alpha crystallin family |
| Glyma.16g206300 | Trypsin and protease inhibitor |
| Glyma.16g206400 | chloroplast relocation |
| Glyma.16g206500 | Ribosomal Proteins L2, C-terminal domain |
| Glyma.16g206600 | ATP binding; nucleic acid binding; helicases |

Previously, RpsUN2 was fine mapped downstream of BARCSOY_SSR_1288 and Rps15 is 7.7 cM upstream of the same marker. Meanwhile, Rps2 was mapped 12.2 cM downstream to Satt431, which means the genetic distance between Rps15 and Rps2 is about 8.6 cM. This result suggests that Rps15 is more likely to be a novel Rps gene rather than a new allele for Rps2 or RpsUN2.

Of the 13 isolates of *P. sojae* used, Rps15 conferred resistance to 12 isolates and only showed susceptibility to Race 7 (Table 15). Rps2 was resistant to 7 isolates, partially resistant to 4, and susceptible to 3 (Race7, Race 13 and Race 17). RpsUN2 was resistant to 6 isolates, with intermediate resistance to 4 and susceptibility to 4. (Race 7, Race 17 and MIN12005.07.02). These results indicated that Rps15 had a much broader resistance spectrum compared with Rps2 and RpsUN2.

TABLE 15

Marker Assisted Resistance Spectrum Analysis of Rps15 to Isolates of *P. sojae*

| *P. sojae* | | F$_{2-3}$ families selected[a] | | Parental lines | | Rps genes on Chr16 | |
|---|---|---|---|---|---|---|---|
| Isolate | Race | Rps15 | Rps15 | PI 594592 | Williams | Rps2 | RpsUN2 |
| 124C-1 | 1 | R[b] | S | R | S | R | R |
| 94-14-432(2) | 3 | R | Segregation | R | S | R | R |
| 94-13p-197 | 4 | R | S | R | S | R | I |
| 95-11-117 (4) | 7 | S | S | R | S | S | S |
| pmg(13)-1 | 13 | R | Segregation | R | S | S | I |
| pmg(17)-1 | 17 | R | Segregation | R | S | S | S |
| pmg(25)-1 | 25 | R | S | R | S | R | R |
| ISA 19A-1 | N/A | R | S | R | S | I | I |
| ISA 71D-1 | N/A | R | S | R | S | I | I |
| MIN1 2001 Jan. 5 | N/A | R | S | R | S | R | R |
| MIN1 2004 Jan. 1 | N/A | R | S | R | S | I | R |
| MIN1 2004 Mar. 1 | N/A | R | S | R | S | R | R |
| MIN1 2005 Jul. 2 | N/A | R | S | R | S | R | S |

[a]Satt431 and InDel3668 are two molecular markers used for selections. The resistance pattern of Rps15 against each *P. sojae* isolate was scored by the proportion of resistance progenies in 8 selected homozygous resistant F$_{2:3}$ families. The reaction of Rps15 was evaluated from 8 homozygous susceptible F$_{2:3}$ families.
[b]A family was recorded as resistant if >75% of seedlings survived after inoculation, susceptible if <25% of seedlings survived, and intermediate resistant if the proportion of resistant seedlings was between 25% and 75%.

To further determine the candidate gene for Rps15, NBS type R-genes, such as those provided in Table 14, will be identified in the Rps15 locus and analyzed. The Rps15 genomic interval will be further fine mapped using a large F$_3$ mapping population derived from a cross between PI 594592 and the susceptible parental Williams cultivar. The mapping population will be genotyped with molecular markers to identify recombinant lines. The recombinants will be phenotyped with *Phytophthora sojae* isolate Race 1. Based on the fine mapping, the Rps15 QTL region will be narrowed down to a smaller genomic interval comprising a few candidate genes for further confirmation. To identify candidate genes for Rps15, a whole genome sequence of PI 594592 will be generated using the PacBio sequencing platform. A contig harboring the flanking markers for the Rps15 genomic interval will be used as a reference sequence for comparing to the sequence data from the susceptible lines, characterizing the genes and identifying candidate genes based on the NBS type R-genes as candidates for Rps15. The NBS type R-genes will be further analyzed for their gene structure to determine if it is a complete NB S type gene or truncated. Gene expression analysis will also be done to determine the expression profile of the NBS type R-genes in the recombinants. Together, with these analyses candidate genes will be expected to be identified for Rps15. Constructs comprising the candidate genes will be generated and transformed into soybean lines that do not carry the Rps15 candidate gene to confirm the Rps15 candidate gene and determining if expression of Rps15 candidate gene in plants increases resistance to *Phytophthora sojae*.

Single copy TO transgenic events will be selected based on the PCR analysis with primers specific to the cloning vector. Final confirmation of the Rps15 gene expression in plants for resistance to *Phytophthora sojae* will be done in the homozygous T2 plants for the Rps15 candidate gene. T2 plants homozygous for the Rps15 candidate gene will be expected to increase resistance to *Phytophthora sojae* isolates as compared to plants not carrying the Rps15 gene. These results would confirm the Rps15 gene.

Example 7

This example demonstrates the identification of the Rps14 sequence.

PI 340029 carries broad resistance to *P. sojae*, including *P. sojae* races 1, 2, 3, 4, 5, 6, 7, 8, and 9. To determine if PI 340029 carries resistance to other races of *P. sojae* hypocotyl inoculation, as described above, was performed. As shown in Table 16, the hypocotyl inoculation studies determined PI 340029 also shows resistance to race 13, race 17, race 25, and two other isolates (ISA19A-1, ISA71D-1) from Indiana soybean fields and four isolates (MIN12001.01.05, MIN12004.01.01, MIN12004.03.01 and MIN12005.07.02) from Minnesota whose pathotypes that do not match any known *P. sojae* race designations. These findings demonstrate that PI 340029 can be a new source for broad *P. sojae* resistance.

TABLE 16

Responses of Soybean Landrace PI 340029 to Different *P. sojae* Isolates

| *P. sojae* Isolate | Virulence Patholotype | No. of plants examined | No. of plants survived | No. of plants killed | Proportion of resistant | Phenotype |
|---|---|---|---|---|---|---|
| Race1 | 7 | 12 | 12 | 0 | 1.00 | Resistant |
| Race17 | 1b, 1d, 2, 3a, 3b, 3c, 4, 5, 6, 7, 8 | 24 | 24 | 0 | 1.00 | Resistant |

TABLE 16-continued

Responses of Soybean Landrace PI 340029 to Different *P. sojae* Isolates

| *P. sojae* Isolate | Virulence Patholotype | No. of plants examined | No. of plants survived | No. of plants killed | Proportion of resistant | Phenotype |
|---|---|---|---|---|---|---|
| Race25 | 1a, 1b, 1c, 1k, 7 | 12 | 12 | 0 | 1.00 | Resistant |
| Race13 | 4, 6, 7 | 8 | 8 | 0 | 1.00 | Resistant |
| ISA 19A-1 | 1a, 1b, 1k, 4, 6, 7 | 10 | 10 | 0 | 1.00 | Resistant |
| ISA 71D-1 | 1a, 1c, 1d, 7 | 7 | 7 | 0 | 1.00 | Resistant |
| MIN1 2001 Jan. 5 | NA | 10 | 10 | 0 | 1.00 | Resistant |
| MIN1 2004 Jan. 1 | NA | 9 | 9 | 0 | 1.00 | Resistant |
| MIN1 2004 Mar. 1 | NA | 10 | 10 | 0 | 1.00 | Resistant |
| MIN1 2005 Jul. 2 | NA | 10 | 10 | 0 | 1.00 | Resistant |
| *Race2 | 1a, 7 | — | — | — | — | Resistant |
| *Race3 | 1a, 2, 3a, 3c, 4, 5, 6, 7 | — | — | — | — | Resistant |
| *Race4 | 1a, 1c, 5, 7 | | | | | Resistant |
| *Race5 | 1a, 1c, 2, 4, 6, 7 | | | | | Resistant |
| *Race6 | 1a, 1d, 3a, 6, 7 | | | | | Resistant |
| *Race7 | 1a, 2, 3a, 3c, 4, 5, 6, 7 | | | | | Resistant |
| *Race8 | 1a, 1d, 6, 7 | | | | | Resistant |
| *Race9 | 1a, 6, 7 | | | | | Resistant |

*P. sojae* isolates previously used to evaluate PI 340029

By crossing PI 340029 with the susceptible Williams cultivar, 167 $F_2$ individuals were produced from self-pollination of the $F_1$. 57 F2 plants were tested for resistance to *P. sojae* race 1, of the 57 F2 plants, 48 were identified as resistant and 9 were identified as susceptible (Table 17). The null hypothesis that resistance was carried by a single locus cannot be rejected ($\chi^2=2.58$, p=0.11). In order to get more accurate phenotypes, $F_{2:3}$ families were tested for resistance to *P. sojae* race 1, the isolate avirulent to most known Rps genes. After harvesting seeds from the remaining $F_2$ plants, 20 to 36 F3 seedlings were tested. Among 110 $F_{2:3}$ families, the segregation ratio of R (homozygous resistant): Rs (segregating): S (homozygous susceptible) observed for response to *P. sojae* race 1 was 28:48:34, which fits the expected ratio for 1:2:1 ($\chi^2=3.4$, p=0.30) (Table 17). This indicates that resistance for *P. sojae* race 1 in PI 340029 is carried by a single Rps locus.

TABLE 17

Segregation Ratios of Phenotypes in the Mapping Population

| Parental lines and mapping population | Observed numbers | | | Expected ratio | $\chi^2$ goodness of fit test | |
|---|---|---|---|---|---|---|
| | R* | Rs | S | ratio | $\chi^2$ | p |
| PI 340029 | 12 | — | 0 | | | |
| Williams | 0 | — | 12 | | | |
| (PI 340029 × Williams) $F_2$ plants | 48 | — | 9 | 3:1 | 2.58 | 0.11 |
| (PI 340029 × Williams) $F_{2:3}$ families | 28 | 48 | 34 | 1:2:1 | 3.4 | 0.30 |

*R—homozygous resistant,
Rs—heterozygous resistant,
S—homozygous susceptible

To detect the genetic region linked to the resistance gene in PI 340029, bulked segregant analysis was performed to initially map the Rps gene on a chromosomal segment. 10 completely susceptible $F_{2:3}$ families and 10 completely resistant $F_{2:3}$ families were selected to make up the susceptible and resistant bulks. SoySNP6K BeadChip consisting of 7039 SNPs was used to genotype both bulks and the two parental lines. There are 1983 SNPs markers in all 20 chromosomes showing polymorphisms between the two parental lines, which were effective and reliable for BSA analysis. After comparing the genotypes of the two bulks, a ~5.8 Mb region was found at the beginning of chromosome 3, on which homozygous nucleotides that are the same as the susceptible parental Williams cultivar were found, while these nucleotides were found heterozygous from both parental lines in the resistance bulk (Table 18). Since no other regions on other chromosomes were found to be different between the two bulks, the chromosomal segment on chromosome 3 is considered closely linked with the rps locus according to the principle of BSA (FIG. 9). Since the region overlaps with some of previously defined Rps1 alleles/genes, the gene on this region was designated Rps14.

TABLE 18

Illustration of Genotypic Comparison Between the Resistant and Susceptible Bulks at the SNP Sites Detected Between the Two Parental Lines at the Beginning of Chromosome 3

| SNP ID | Chromo-some | Pos-ition(bp) | PI 340029 | Re-sistant Bulk | Sus-ceptible Bulk | Williams |
|---|---|---|---|---|---|---|
| SNP178 | Gm03 | 829023 | TT | TG | GG | GG |
| SNP179 | Gm03 | 1671384 | AA | AC | CC | CC |
| SNP180 | Gm03 | 1718435 | GG | AG | AA | AA |
| SNP181 | Gm03 | 1758253 | CC | TC | TC | TT |
| SNP183 | Gm03 | 2818076 | CC | TC | TC | TT |
| SNP184 | Gm03 | 3087237 | AA | AG | GG | GG |
| SNP185 | Gm03 | 3907697 | GG | AG | AA | AA |
| SNP186 | Gm03 | 4487138 | CC | AC | AA | AA |
| SNP187 | Gm03 | 4509101 | AA | AG | GG | GG |

TABLE 18-continued

Illustration of Genotypic Comparison Between the Resistant
and Susceptible Bulks at the SNP Sites Detected Between
the Two Parental Lines at the Beginning of Chromosome 3

| SNP ID | Chromo- some | Pos- ition(bp) | PI 340029 | Re- sistant Bulk | Sus- ceptible Bulk | Williams |
|---|---|---|---|---|---|---|
| SNP188 | Gm03 | 4665923 | CC | TC | TT | TT |
| SNP189 | Gm03 | 4782127 | CC | TC | TT | TT |
| SNP190 | Gm03 | 4903317 | GG | AG | AG | AA |
| SNP191 | Gm03 | 5165511 | AA | AC | CC | CC |
| SNP192 | Gm03 | 5217414 | CC | TC | TT | TT |
| SNP193 | Gm03 | 5796468 | AA | AG | AG | GG |
| SNP194 | Gm03 | 6631189 | GG | AG | AG | AA |
| SNP195 | Gm03 | 6844115 | CC | AC | AC | AA |
| SNP196 | Gm03 | 8003327 | TT | TC | TC | CC |
| SNP197 | Gm03 | 8228940 | AA | AG | AG | GG |
| SNP198 | Gm03 | 9641204 | AA | AC | AC | CC |

Based on the initial mapping results, a series of potential SSR markers located on the region mapped by BSA were screened and 5 markers, Satt631, BARCSOYSSR_03_0209, BARCSOYSSR_03_0219, BARCSOYSSR_03_0226 and BARCSOYSSR_03_0226, which showed clear polymorphisms between the two parental lines were identified (Table 19). These 5 markers were chosen to genotype all 110 $F_{2:3}$ families. As expected, all markers observed a 1:2:1 segregation ratio, and 9, 4, 4, 2 and 6 recombinants between each of these five markers and the Rps14 locus were defined, respectively (Table 20). Among these 5 markers, Rps14 is more closely linked to BARCSOYSSR_03_0226 compared with the other four markers. A linkage map was constructed with these five markers and all the five markers were in good agreement with their order annotated on the Williams 82 reference genome (FIG. 10). The Rps14 locus was narrowed to a 4.5 cM region flanked by BARCSOYSSR_03_0226 and BARCSOYSSR_03_0266.

TABLE 19

Polymorphic Insertion/Deletion and SSR Markers
Identified Between PI340029 and Williams

| SSR Marker | Ch | Forward primer | Reverse primer |
|---|---|---|---|
| Satt631 | 03 | SEQ ID NO: 104 | SEQ ID NO: 105 |
| BARCSOYSSR_03_0209 | 03 | SEQ ID NO: 106 | SEQ ID NO: 107 |
| BARCSOYSSR_03_0219 | 03 | SEQ ID NO: 108 | SEQ ID NO: 109 |
| BARCSOYSSR_03_0226 | 03 | SEQ ID NO: 110 | SEQ ID NO: 111 |
| BARCSOYSSR_03_0229 | 03 | SEQ ID NO: 112 | SEQ ID NO: 113 |
| BARCSOYSSR_03_0266 | 03 | SEQ ID NO: 114 | SEQ ID NO: 115 |
| InDel3971 | 03 | SEQ ID NO: 116 | SEQ ID NO: 117 |
| InDel4033 | 03 | SEQ ID NO: 118 | SEQ ID NO: 119 |
| InDel4263 | 03 | SEQ ID NO: 120 | SEQ ID NO: 121 |
| InDel4330 | 03 | SEQ ID NO: 122 | SEQ ID NO: 123 |

TABLE 20

Chi-Square ($\chi^2$) Goodness of Fit Test for the
Markers in the $F_2$ Population Deduced Based on the
$F_{2:3}$ Progenies Derived From Pi 594592 × Williams

| Marker | Observed number[a] | | | $\chi^2$ goodness of fit test | |
|---|---|---|---|---|---|
| | a | h | b | $\chi^{2\,1:2:1}$ | p |
| Satt631 | 25 | 50 | 34 | 2.23 | 0.33 |
| BARCSOYSSR_03_0209 | 25 | 50 | 35 | 2.73 | 0.26 |
| BARCSOYSSR_03_0219 | 25 | 50 | 35 | 2.73 | 0.26 |

TABLE 20-continued

Chi-Square ($\chi^2$) Goodness of Fit Test for the
Markers in the $F_2$ Population Deduced Based on the
$F_{2:3}$ Progenies Derived From Pi 594592 × Williams

| Marker | Observed number[a] | | | $\chi^2$ goodness of fit test | |
|---|---|---|---|---|---|
| | a | h | b | $\chi^{2\,1:2:1}$ | p |
| BARCSOYSSR_03_0226 | 25 | 50 | 35 | 2.73 | 0.26 |
| BARCSOYSSR_03_0266 | 30 | 46 | 34 | 3.24 | 0.20 |

[a]a means homozygous for the marker allele from the resistant PI 594592; b means homozygous for the marker allele from the susceptible Williams; h means heterozygous for the marker alleles from both parents In order to narrow the mapping region of Rps14, two SSR markers, BARCSOYSSR_03_0219 and BARCSOYSSR_03_0266, were selected to genotype $F_3$ plants and 21 recombinants were identified. Subsequently, the $F_{3:4}$ families derived from these recombinants were tested with *P. sojae* race 1. One additional SSR polymorphism marker and four InDel markers developed from comparison between re-sequencing data of two parental lines to genotype these recombinants by pooling of $F_4$ seedlings from $F_{3:4}$ families was also used. Four recombinants (205-1, 83-3, 161-1, 174-2) defined the Rps14 locus to downstream of marker InDel4033, while 3 recombinants (59-8, 12-2, 152-5) defined the Rps14 locus to upstream of marker InDel4263. For the remaining 16 recombinants, genotypes and phenotypes were all consistent with the seven key recombinants. Therefore, the Rps14 was further mapped to the region flanked by InDel4033 and InDel4263, which defined a ~229 kb region based on the Williams 82 soybean reference genome.

Previously, RpsUN1 was fine mapped to a ~151 kb region defined by BARCSOYSSR_03_0233 and BARCSOYSSR_03_0246 (Li et al. 2016). The Rps14 region is ~137 kb overlapped with fine mapped RpsUN1 region based on Williams 82 reference genome. There are 7 genes in that region including three predicted R genes with NBS_LRR domains (Table 21).

TABLE 21

Gene Annotation in the Mapped Region According
to the Soybean Reference Genome (Wm82.a2.v1)

| Genes | Annotation |
|---|---|
| Glyma.03g034500 | NB-ARC domain-containing disease resistance protein |
| Glyma.03g034600 | AAA-type ATPase family protein |
| Glyma.03g034700 | zinc ion binding; nucleic acid binding |
| Glyma.03g034800 | NB-ARC domain-containing disease resistance protein |
| Glyma.03g034900 | LRR and NB-ARC domains-containing disease resistance protein |
| Glyma.03g035000 | Nucleic acid-binding, OB-fold-like protein |
| Glyma.03g035100 | PIF1-like helicase |

RNA-seq revealed that only three genes expressed in the *P. sojae* infection process in the resistance donor line PI 340029, namely Glyma.03g034500, Glyma.03g034800 and Glyma.03g034900 according to reference genome Wms82.v2. al. All these three genes were annotated to encode NBS_LRR proteins. In the susceptible donor line Williams, these three genes show no or extremely low levels of expression in the process of *P. sojae* infection. Therefore, these three genes are all candidate genes for Rps14.

Previously, Rps1 (Rps1a, Rps1b, Rps1c, Rps1d, Rps1k), RpsUN1, Rps7 and Rps9 were also mapped to short arm of chromosome 3 and may overlap or be adjacent to the Rps14 region. To determine whether the Rps14 loci is distinct from these Rps loci, 204 accessions showing resistance to *P. sojae* according to USDA germplasm collection, 9 ancestral lines for Rps genes on chromosome 3 and the Rps14 donor line PI 340029 were selected for haplotype analysis. SNP genotypic data on the 540 kb region defined by SSR marker BARCSOYSSR_03_0226 and BARCSOYSSR_03_0266 were extracted. The generation of SNP data was previously described (Li et al., 2016), and a total of 31 SNPs in the defined region were called from these 213 different soybean accessions. Based on the topology of the neighbor-joining tree, the donor line of Rps14, PI 340029, belongs to a distinct branch compared with ancestral lines for other known Rps genes on chromosome 3.

By genotyping with two flanking markers (InDel4033 and InDel4263), eight homozygous resistance families were tested with eight homozygous susceptible families as control. Rps14 was resistant to all 13 *P. sojae* isolates, with all homozygous susceptible families and Williams showing intolerance to the disease (Table 22).

PI 340029 will be generated using the PacBio sequencing platform. Contig harboring the flanking markers for the Rps14 genomic interval will be used as a reference sequence for comparing to the sequence data from the susceptible lines in order to characterize the genes and identify candidate genes based on the NBS type R-genes. The NBS type R-genes will be further analyzed for their gene structure to determine if it is a complete NB S type gene or truncated. Gene expression analysis will also be done to determine the expression profile of the NBS type R-genes in the recombinants. Together, with these analyses candidate genes will be expected to be identified for Rps14. Constructs comprising the candidate genes will be generated and transformed into soybean lines that do not carry the Rps14 candidate gene to confirm the Rps14 candidate gene and determining if expression of Rps14 candidate gene in plants increases resistance to *Phytophthora sojae*.

Single copy TO transgenic events will be selected based on the PCR analysis with primers specific to the cloning

TABLE 22

Marker Assisted Resistance Spectrum Analysis of Rps14 to Isolates of *P. sojae*

| *P. sojae* | $F_{3-4}$ families selected[a] | | Parental lines | | Rps genes on Chr03 | | | | | |
|---|---|---|---|---|---|---|---|---|---|---|
| Isolate | Rps14 | Rps14 | PI 340029 | Williams | 1-a | 1-b | 1-c | 1-d | 1-k | UN1[c] |
| Race1 | R[b] | S | R | S | R | R | R | R | R | R |
| Race3 | R | S | R | S | S | R | R | R | R | I |
| Race4 | R | S | R | S | S | R | S | S | R | S |
| Race7 | R | S | R | S | S | R | R | R | R | R |
| Race13 | R | S | R | S | R | R | R | I | R | R |
| Race17 | R | S | R | S | S | S | R | S | R | R |
| Race25 | R | S | R | S | S | S | S | R | S | S |
| ISA19A-1 | R | S | R | S | S | S | R | S | S | R |
| ISA71D-1 | R | S | R | S | S | I | S | S | S | S |
| MIN1 2001 Jan. 5 | R | S | R | S | R | R | S | S | R | — |
| MIN1 2004 Jan. 1 | R | S | R | S | S | S | S | I | S | — |
| MIN1 2004 Mar. 1 | R | S | R | S | S | S | S | S | S | — |
| MIN1 2005 Jul. 2 | R | S | R | S | S | S | R | S | S | — |

[a]InDel4033 and InDel4261 are two molecular markers used for selections. The resistance pattern of Rps14 against each *P. sojae* isolate was scored by the proportion of resistance progenies in 8 selected homozygous resistant $F_{2-3}$ families. The reaction of Rps14 was evaluated from 8 homozygous susceptible $F_{2-3}$ families.
[b]A family was recorded as resistant if >75% of seedlings survived after inoculation, susceptible if <25% of seedlings survived, and intermediate resistant if the proportion of resistant seedlings was between 25% and 75%.
[c]Phenotypes is based on Lin et al. 2013.

Rps14 was initially mapped to Rps1 region also harboring Rps1a, Rps1b, Rps1c, Rps1d, Rps1k and RpsUN1. However, none of these Rps1 genes showed similar resistance pattern as Rps14. The resistance pattern combined with the haplotype analysis demonstrate that Rps14 is likely a novel gene rather than a novel Rps1 allele.

Example 8

This example demonstrates expression of the Rps14 in plants to increase resistance to *Phytophthora sojae*.

The Rps14 genomic interval will be further fine mapped using a large $F_3$ mapping population derived from a cross between PI 340029 and the susceptible Williams cultivar. The mapping population will be genotyped with molecular markers to identify recombinant lines. The recombinants will be phenotyped with *Phytophthora sojae* isolate Race 1. Based on the fine mapping the Rps14 QTL region will be narrowed down to a smaller genomic interval comprising candidate genes for further confirmation. For identifying candidate genes for Rps14, the whole genome sequence of vector. Final confirmation of the Rps14 gene expression in plants for resistance to *Phytophthora sojae* will be done in the homozygous T2 plants for the Rps14 candidate gene. T2 plants homozygous for the Rps14 candidate gene will be expected to increase resistance to *Phytophthora sojae* isolates as compared to plants not carrying the Rps14 gene. These results would confirm the Rps14 gene.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

Terms used in the claims and specification are defined as set forth below unless otherwise specified. It must be noted that, as used in the specification and the appended claims, the singular forms "a," "an" and "the" include plural referents unless the context clearly dictates otherwise.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

What is claimed is:

1. A soybean plant or soybean seed comprising a targeted genetic modification that increases expression of a polynucleotide, relative to a control plant not comprising the targeted genetic modification, wherein said polynucleotide encodes a polypeptide comprising an amino acid sequence having at least 95% sequence identity to SEQ ID NO: 2, wherein the targeted genetic modification provides increased resistance to *Phytophthora* infection in the soybean plant or a plant grown from the soybean seed as compared to a control plant lacking the targeted genetic modification, and said modification comprises the introduction of said polynucleotide into the cells of said soybean plant or soybean seed by transfection or by introgression.

2. A soybean plant or soybean seed comprising a gene construct, said gene construct comprising a heterologous promoter operably linked to a polynucleotide sequence encoding a polypeptide having at least 95% sequence identity to SEQ ID NO: 2, wherein said gene construct provides increased resistance to *Phytophthora* infection as compared to a control plant lacking said gene construct.

3. A plant produced by the soybean seed of claim 1.

4. A method of plant breeding comprising crossing the soybean plant of claim 3 with a second soybean plant to produce a progeny seed, wherein the cells of said progeny seed comprise said polynucleotide sequence.

5. The method of claim 4, wherein a plant produced from said progeny seed has increased resistance to at least one race of *Phytophthora* relative to plants lacking said polynucleotide sequence.

6. The method of claim 5, wherein the second soybean plant is susceptible to the at least one race of *Phytophthora.*

7. The method of claim 5, wherein the at least one race of *Phytophthora* is at least one of Race1, Race 2, Race3, Race4, Race5, Race6, Race7, Race8, Race9, Race13, Race17, Race25, or Race 31.

8. A method of producing the soybean plant or soybean seed of claim 1 comprising the steps of (a) expressing in a regenerable plant cell an exogenous polynucleotide encoding a polypeptide comprising an amino acid sequence having at least 95% sequence identity to SEQ ID NO: 2, and (b) generating a plant wherein the plant expresses the polynucleotide and has increased resistance to *Phytophthora* infection as compared to a control plant lacking said exogenous polynucleotide.

9. The soybean plant or soybean seed of claim 1 wherein said polynucleotide encodes a polypeptide comprising an amino acid sequence of SEQ ID NO: 2.

\* \* \* \* \*